(12) United States Patent  (10) Patent No.: US 8,969,313 B2
Yu  (45) Date of Patent: Mar. 3, 2015

(54) METHODS AND COMPOUNDS FOR PREVENTING AND TREATING A TUMOUR

(75) Inventor: Qiang Yu, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 885 days.

(21) Appl. No.: 12/740,912

(22) PCT Filed: Nov. 3, 2008

(86) PCT No.: PCT/SG2008/000420
§ 371 (c)(1),
(2), (4) Date: Aug. 3, 2010

(87) PCT Pub. No.: WO2009/058102
PCT Pub. Date: May 7, 2009

(65) Prior Publication Data
US 2011/0053882 A1    Mar. 3, 2011

Related U.S. Application Data

(60) Provisional application No. 60/984,835, filed on Nov. 2, 2007, provisional application No. 61/059,482, filed on Jun. 6, 2008.

(51) Int. Cl.
*A61K 31/7064* (2006.01)
*A61P 35/00* (2006.01)
*G01N 33/53* (2006.01)
*A61K 31/519* (2006.01)
*A61K 31/52* (2006.01)
*G01N 33/50* (2006.01)

(52) U.S. Cl.
CPC .............. *A61K 31/519* (2013.01); *A61K 31/52* (2013.01); *G01N 33/5011* (2013.01); *G01N 2800/52* (2013.01)
USPC .............................. 514/43; 514/394; 514/645

(58) Field of Classification Search
USPC ............................................ 514/43, 394, 645
See application file for complete search history.

(56) References Cited

U.S. PATENT DOCUMENTS

| 4,816,575 | A | 3/1989 | Fukukawa et al. |
| 5,217,999 | A | 6/1993 | Levitzki et al. |
| 5,302,606 | A | 4/1994 | Spada et al. |
| 5,330,992 | A | 7/1994 | Eissenstat et al. |
| 2005/0191618 | A1 | 9/2005 | McSwiggen et al. |
| 2005/0244417 | A1 | 11/2005 | Ashkenazi et al. |
| 2005/0245559 | A1 | 11/2005 | Koul et al. |
| 2005/0266093 | A1 | 12/2005 | Mohapatra |
| 2006/0147456 | A1 | 7/2006 | Lebecque et al. |

FOREIGN PATENT DOCUMENTS

| EP | 0 383 531 | 8/1990 |
| EP | 0 566 226 | 10/1993 |
| WO | WO-91/15495 | 10/1991 |
| WO | WO-92/20642 | 11/1992 |
| WO | WO-92/21660 | 12/1992 |
| WO | WO-94/03427 | 2/1994 |

(Continued)

OTHER PUBLICATIONS

Katoh, "Identification and characterization of human DAPPER1 and DAPPER2 genes in silico", International Journal of Oncology, 2003, 22, pp. 907-913.*
Duerre et al., Biochem Cell Biol., 70(8):703-711 (1992).
Aguilera et al., Oncogene, 25:4116-4121 (2006).
Azuara et al., Nat Cell Biol, 8:532-538 (2006).
Barker et al., Nat Rev Drug Discov, 5:997-1014 (2006).
Baylin et al., Nat Rev Cancer, 6:107-116 (2006).
Bernstein et al., Cell, 125:315-326 (2006).
Beste et al., PNAS, 96:1898-1903 (1999).
Bikkavilli et al., Journal of Cell Science, 121(2):234-245 (2008).
Bilic et al., Science, 316:1619-1622 (2007).

(Continued)

*Primary Examiner* — Sreeni Padmanabhan
*Assistant Examiner* — Sahar Javanmard
(74) *Attorney, Agent, or Firm* — Blakely, Sokoloff, Taylor & Zafman LLP

(57) ABSTRACT

The invention relates to a method of preventing, inhibiting, arresting or reversing tumorigenesis in a cell as well as a method of inducing apoptosis in a tumor cell. The method includes increasing the amount and/or the activity of a DACT protein, or a functional fragment thereof, in the cell. Also provided is a pharmaceutical composition that comprises a compound of general formula (I), wherein A is CH or N, $R^1$, $R^4$ and $R^5$ are independent from each other H, an aliphatic group, an alicyclic group, an aromatic group, an arylaliphatic group, and an arylalicyclic group comprising 0-3 heteroatoms. The heteroatoms may be N, O, S, or Si. $R^4$ and $R^5$ may optionally be linked so as to define an aliphatic hydrocarbyl bridge. $R^2$ is H or a halogen such as F, Cl, Br or L. $R^3$ is H, F, Cl or an aliphatic or arylaliphatic group that includes 1-8 main chain carbon atoms and 0-3 heteroatoms. The pharmaceutical composition also comprises a histone deacetylase inhibitor.

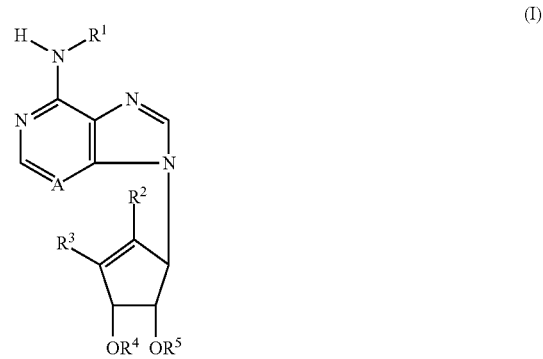

7 Claims, 41 Drawing Sheets

(56) References Cited

FOREIGN PATENT DOCUMENTS

| WO | WO-94/14808 | 7/1994 |
|---|---|---|
| WO | WO-96/23879 | 8/1996 |
| WO | WO-01/92655 | 12/2001 |
| WO | WO-02/32920 | 4/2002 |
| WO | WO-03/029462 | 4/2003 |
| WO | WO-2005/019254 | 3/2005 |
| WO | WO-2005/019255 | 3/2005 |
| WO | WO-2005/019256 | 3/2005 |
| WO | WO-2007/100304 | 9/2007 |
| WO | WO-2008/122440 | 10/2008 |

OTHER PUBLICATIONS

Brown et al., Trends in Molecular Medicine, 8(4 supp):S43-S48 (2002).
Brumbaugh et al., Epigenetics, 3(5):254-257 (2008).
Cadigan, Current Biology, 18(20):R943-R947 (2008).
Calviello et al., Carcinogenesis, 28(6):1202-1209 (2007).
Cheyette et al., Dev Cell, 2:449-461 (2002).
Costa, Gene, 357:83-94 (2005).
de Lau et al., Front Biosci, 12:471-491 (2007).
Endo et al., Analytica Chimica Acta, 614(2):182-189 (2008).
Filali et al., J Biol Chem, 277:33398-33410 (2002).
Fisher et al., Developmental Dynamics, 235:2620-2630 (2006).
Fodde et al., Curr Opin Cell Biol, 19: 150-158 (2007).
Fujii et al., Cancer Res, 67:573-579 (2007).
Gao et al., J Biol. Chem., available at http://www.jbc.org/cgi/doi/10.1074/jbc.M804088200.
Giles et al., Biochim Biophys Acta, 1653:1-24 (2003).
Gill et al., Current Opinion in Biotechnology, 17:653-658 (2006).
Gloy et al., Nat Cell Biol, 4:351-357 (2002).
Hamblet et al., Development, 129:5827-5838 (2002).
Haustein et al., Annu. Rev. Biophys. Biomol. Struct., 36:151-169 (2007).
He et al., Oncogene, 24:3054-3058 (2005).
He et al., Science, 281:1509-1512 (1998).
Hikasa et al., Development, 131:4725-4734 (2004).
Holt at al., Trends Biotechnol., 21(11):484-490 (2003).
Huang et al., Trends Mol. Med., 14(11):503-509 (2008).
Iacobuzio-Donahue, Annu. Rev. Pathol. Mech. Dis., 4:229-249 (2009).
Illiades et al., FEBS Lett., 409(3):437-441 (1997).
International Preliminary Report on Patentability dated Feb. 26, 2010 for PCT Application No. PCT/SG2008/000420.
International Search Report and the Written Opinion dated Jan. 19, 2009 for PCT Application No. PCT/SG2008/000420.
Iriyama et al., Biochem. Biophys. Res. Commun., 375:173-177 (2008).
Jiang et al., Cancer Cell., 13(6):529-541 (2008).
Kinzler et al., Cell, 87:159-170 (1996).
Kramer et al., Cancer Research, 50(13):3838-3842 (1990).
Kwon et al., J. Am. Chem. Soc., 129: 1508-1509 (2007).
Kwong et al., Oncogene, 21:8340-8346 (2002).
Lammi et al., Am J Hum Genet, 74:1043-1050 (2004).
Lee et al., Cellular Signalling, 20:443-452 (2008).
Lepourcelet et al., Cancer Cell, 5:91-102 (2004).
Li et al., Cancer Biol Ther, 1:621-625 (2002).
Lidke et al., Current Protocols in Cell Biology, 25.1.1-25.1.18, doi:10.1002/0471143030.cb2501s36 (2007).
Lin et al., Nature, 455:1119-1124 (2008).
Lin, Science, 316:397 (2007).
Liu et al., J. Am. Chem. Soc., 126: 4076-4077 (2004).
Liu et al., Nat Genet, 26:146-147 (2000).
Liu, Current Opinion in Cell Biology, 20:214-221 (2008).
Logan et al., Annu Rev Cell Dev Biol, 20:781-810 (2004).
Mahindroo et al., Bioorganic & Medicinal Chemistry Letters, 18:946-949 (2008).
Malanchi et al., Nature, 452:650-653 (2008).
Marson et al., Cell Stem Cell, 3:132-135 (2008).
Mikkelsen et al., Nature, 448:553-560 (2007).
Moon et al., Bioorg Med Chem Lett., 14(22):5641-5644 (2004).
Morin et al., Science, 275:1787-1790 (1997).
Mosavi et al., Protein Science, 13(6):1435-1448 (2004).
Ohm et al., Nat Genet, 39:237-242 (2007).
Ooi et al., Nature, 448:714-717 (2007).
Otto et al., Journal of Cell Science, 121:2939-2950 (2008).
Pan et al., Cell Stem Cell, 1:299-312 (2007).
Peifer et al., Science, 287:1606-1609 (2000).
Polakis, Curr Opin Genet Dev, 17:45-51 (2007).
Rice et al., Molecular Cancer Therapeutics, pp. 885-892 (2003).
Sato et al., Nature Medicine, 10(1):55-63 (2004).
Schlesinger et al., Nat Genet, 39:232-236 (2007).
Shyu et al., Trends Biotech., 26(11):622-630 (2008).
Silverman et al., Nature Biotechnology, 23:1556-1561 (2005).
Siu et al., Cancer Res, 59:63-66 (1999).
Skerra, J. Mol. Recognit., 13:167-187 (2000).
Smith et al., International Journal of Biochemistry & Cell Biology, doi:10.1016/j.bioce1.2008.09008 (2008).
Song et al., Nature Biotech., 23(6):709-717 (2005).
Stone et al., Journal of Immunological Methods, 318:88-94 (2007).
Su et al., FASEB J, 21:682-690 (2007).
Su et al., Science, 256:668-670 (1992).
Suzuki et al., Nat Genet, 31:141-149 (2002).
Suzuki et al., Nat Genet, 36:417-422 (2004).
Szyf, Annu. Rev. Pharmacol. Toxicol., 49:243-263 (2009).
Tan et al., Genes & Development, 21(9):1050-1063 (2007).
Tay et al., Nature, 455:1124-1129 (2008).
Tetsu et al, Nature, 398:422-426 (1999).
van de Wetering et al., Cell, 111:241-250 (2002).
van Dekken et al., Acta Histochemica, 109(4):266-272 (2007).
Wang et al., J. Biol. Chem., http://www.jbc.org/cgi/doi/10.1074/jbc.M804091200.
Weber et al., Nat Genet, 39:457-466 (2007).
Wei et al., Lung Cancer, available at doi:10.1016/j.lungcan.2008.06.018.
Weiss et al., Nature Chem. Biol., 3(12):739-744 (2007).
Widschwendter et al., Nat Genet, 39:157-158 (2007).
Wielenga et al., Am J Pathol, 154:515-523 (1999).
Wong et al., Molecular Cell, 12(5):1251-1260 (2003).
Xie et al., Annu. Rev. Biophys., 37:417-444 (2008).
Yau, Oncogene, 24:1607-1614 (2005).
Yoo et al., Nature Reviews Drug Discovery, 5(1):37-50 (2006).
Yoshikawa et al., Nat Genet, 28:29-35 (2001).
You et al., Mol Cancer Ther, 7(6):1633-1638 (2008).
Yu et al., Cancer Res, 67:10657-10663 (2007).
Zamore et al., Science, 309:1519-1524 (2005).
Zhang et al., J Biol Chem, 281(13)8607-8612 (2006).
Zhang et al., Science, 306:114-117 (2004).
Zhao et al., Cell Stem Cell, 3:286-298 (2007).
Zhao et al., PNAS, 102:16090-16095(2005).

\* cited by examiner (continued on next page)

(common knowledge in the art)

(common knowledge in the art)

(continued on next page)

(suggested mechanism underlying an embodiment of the invention)

Fig. 3A
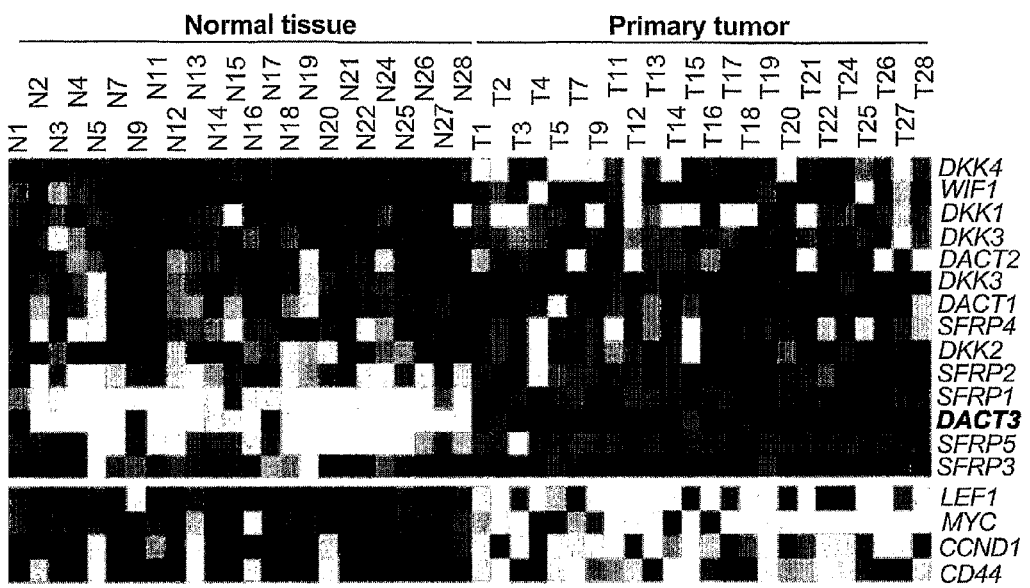
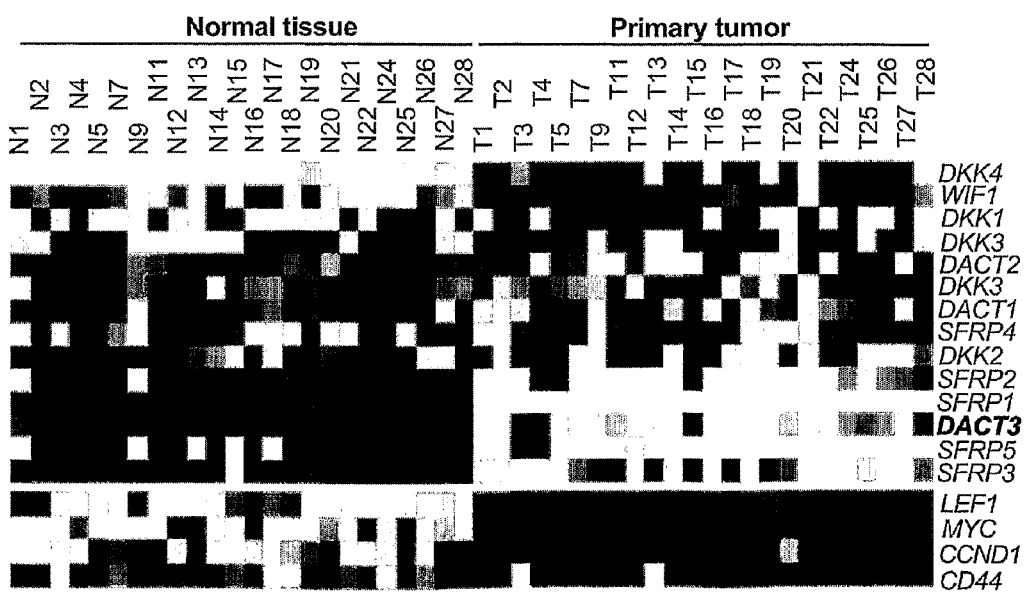

(cont. on next page)

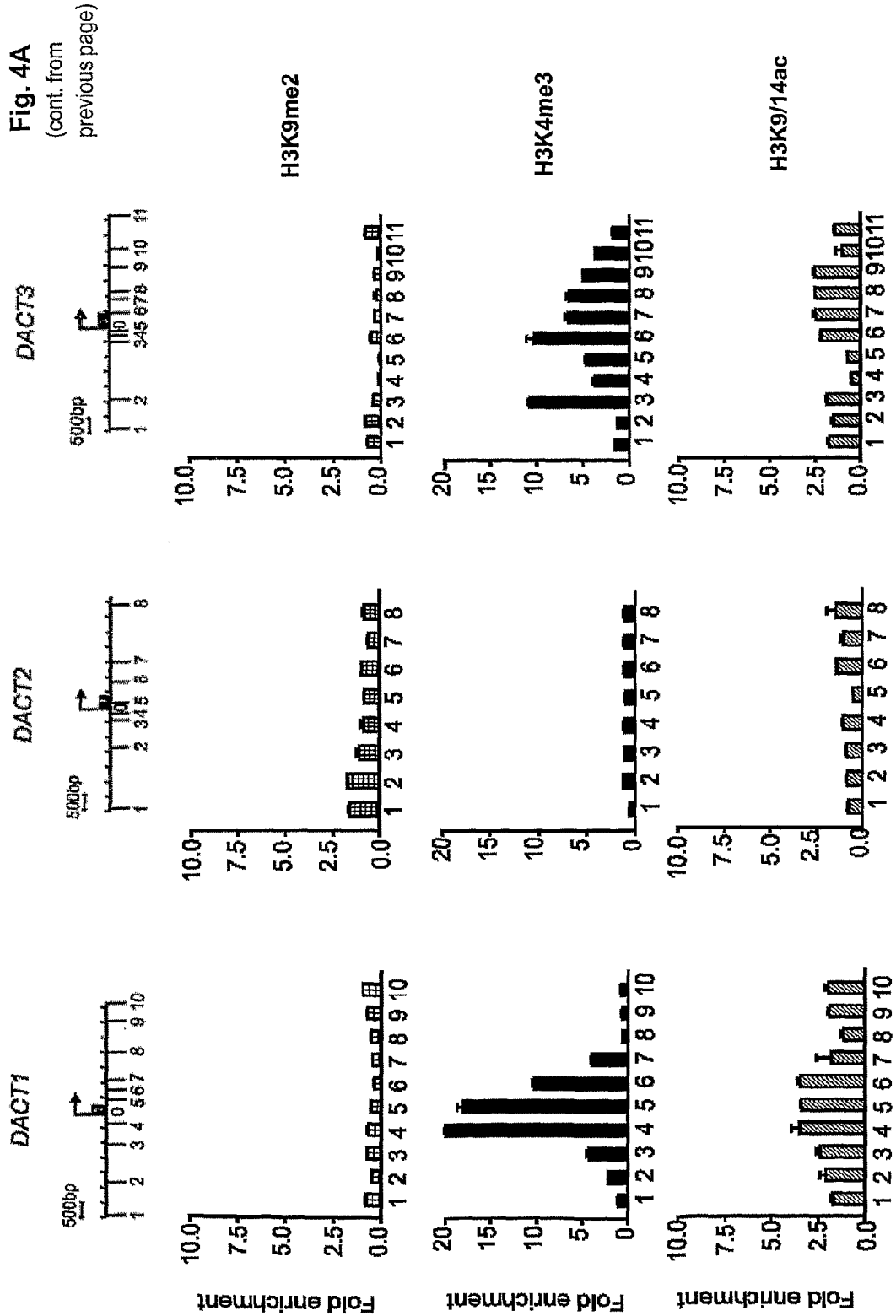
Fig. 4A (cont. from previous page)

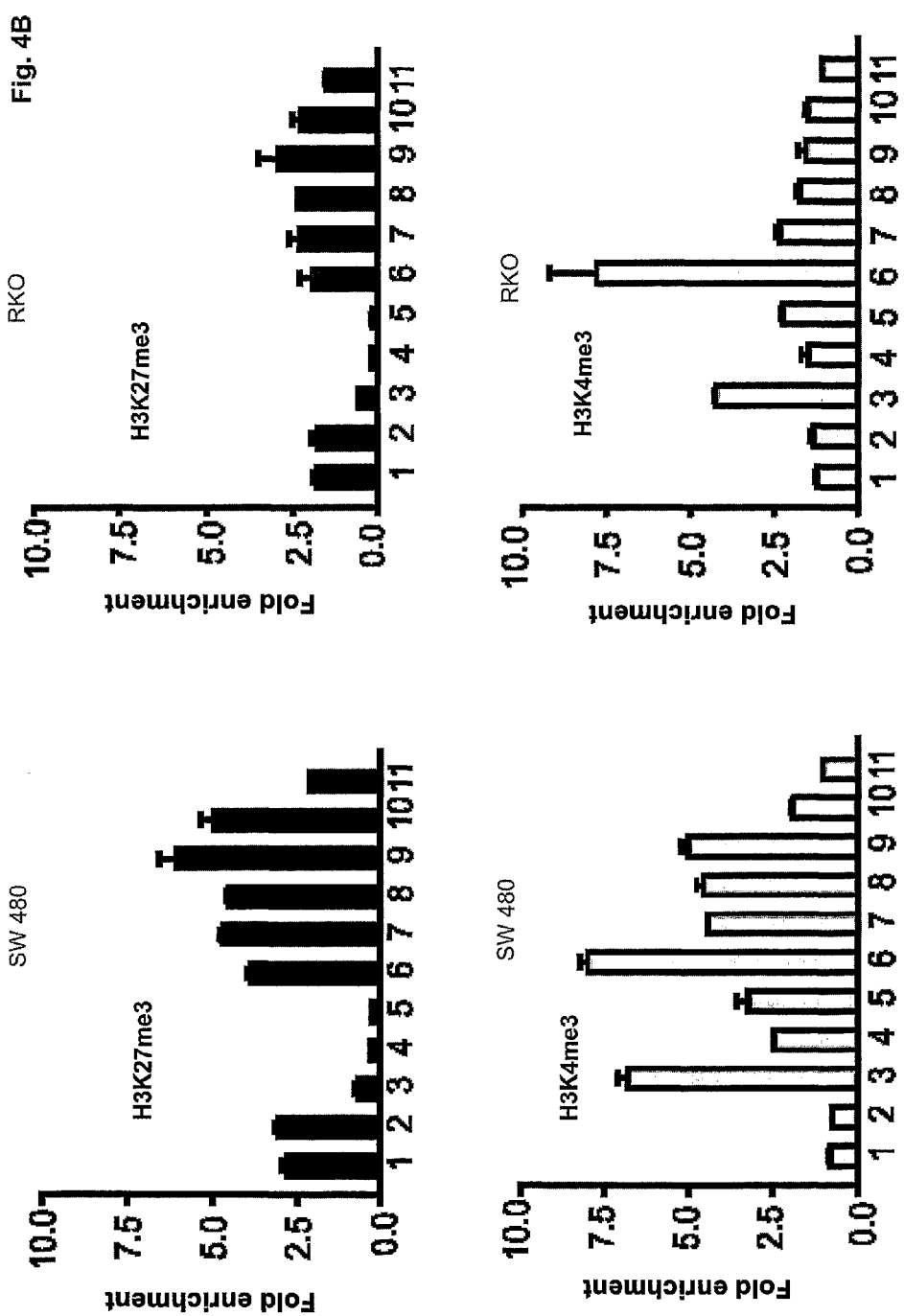

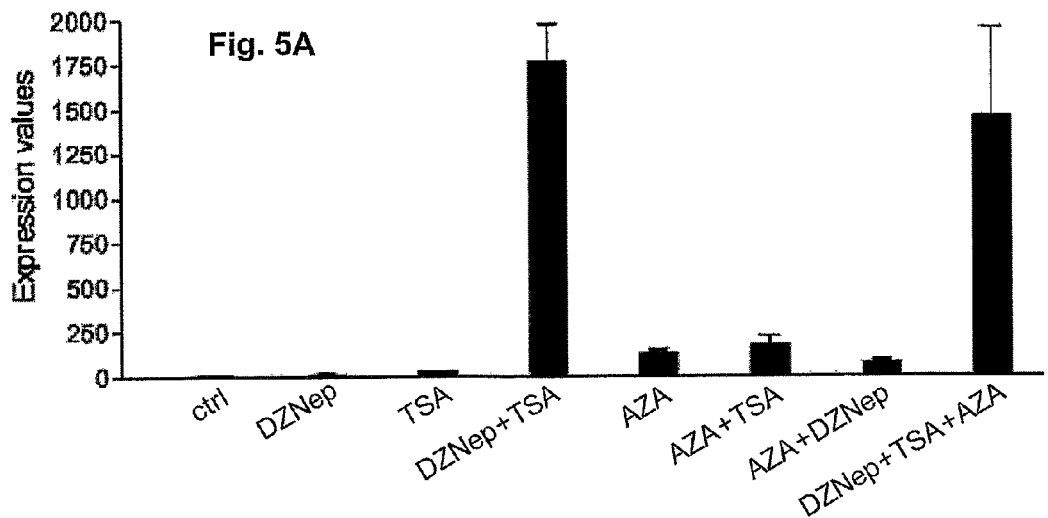
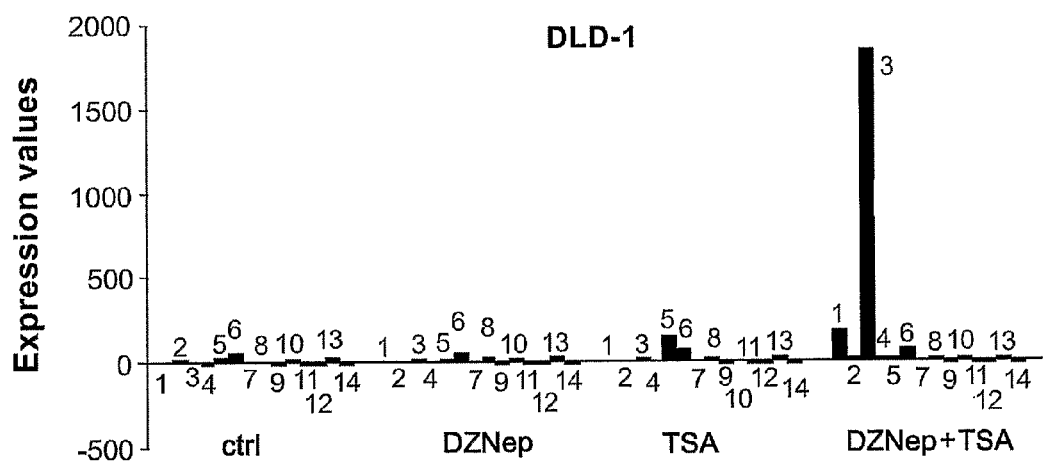
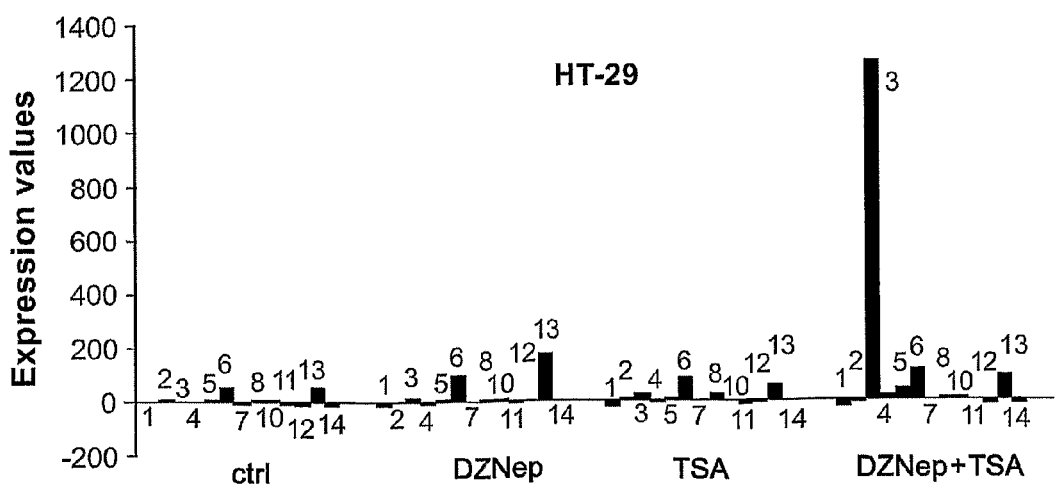

Fig. 6D

| | DLD1 | | | | SW480 | | | | HT29 | | | |
|---|---|---|---|---|---|---|---|---|---|---|---|---|
| | ctrl | DZNep | TSA | D+T | ctrl | DZNep | TSA | D+T | ctrl | DZNep | TSA | D+T |
| ASCL2 | 16586.2 | 14056.1 | 10574.1 | 805.2 | 8427.9 | 8504.1 | 7948 | 469.4 | 1377.8 | 1066.4 | 993.4 | 350.7 |
| AXIN2 | 14381.7 | 12891.8 | 24437.8 | 3055.5 | 20266 | 21347.4 | 17511.3 | 5716 | 3527.8 | 2118.8 | 2187.9 | 2989.6 |
| CCND1 | 18822.8 | 8070.2 | 25986.1 | 2282.3 | 44480.2 | 34890.5 | 44286.2 | 8130.8 | 9264.9 | 7183.9 | 6813,9 | 3756 |
| LEF1 | 3539.9 | 3412.6 | 2449.6 | 684.7 | 1388.2 | 1951.5 | 1482.2 | 465.1 | -4.7 | -4.3 | 3 | -10 |
| MYC | 6140.2 | 12065.4 | 5294.5 | 503.5 | 5414.5 | 11606.5 | 9214.6 | 4520.3 | 6401.6 | 4831 | 5529.3 | 2530.1 |
| RUNX1 | 93.1 | 110.4 | 102.2 | 22.8 | 692.6 | 490.7 | 607.6 | 96.3 | 310.3 | 218.8 | 266 | 146.9 |
| PPARG | 1551.1 | 886.9 | 1849 | 282 | 1020.2 | 289.5 | 694.4 | 118.8 | 9998.4 | 6440.7 | 8019.9 | 4355.2 |
| ATXN1 | 268.3 | 195.4 | 371.8 | 84.6 | 551.3 | 368.7 | 553 | 50.8 | 919.4 | 633.7 | 780.2 | 398.1 |
| CD44 | 1425.4 | 1051.7 | 1227.5 | 274.5 | 4331.2 | 4483.6 | 2548.7 | 263.4 | 18884 | 10692 | 12432 | 3398.5 |

Others

| | DLD1 | | | | SW480 | | | | HT29 | | | |
|---|---|---|---|---|---|---|---|---|---|---|---|---|
| | ctrl | DZNep | TSA | D+T | ctrl | DZNep | TSA | D+T | ctrl | DZNep | TSA | D+T |
| NKD1 | 342.1 | 195.5 | 273.2 | 481.3 | 2866.1 | 3101.5 | 3300.9 | 2474.3 | 11.7 | 14.6 | 5.3 | 14.6 |
| CTNNB1 | 760.8 | 1020.5 | 882.7 | 904.3 | 2028.4 | 2408.7 | 921.7 | 616.2 | 808.7 | 465 | 509 | 463.2 |
| DVL2 | 510.3 | 462.6 | 408 | 343.3 | 445 | 478 | 268.2 | 239.4 | 411.9 | 282.6 | 276.8 | 230.1 |

Fig. 6E
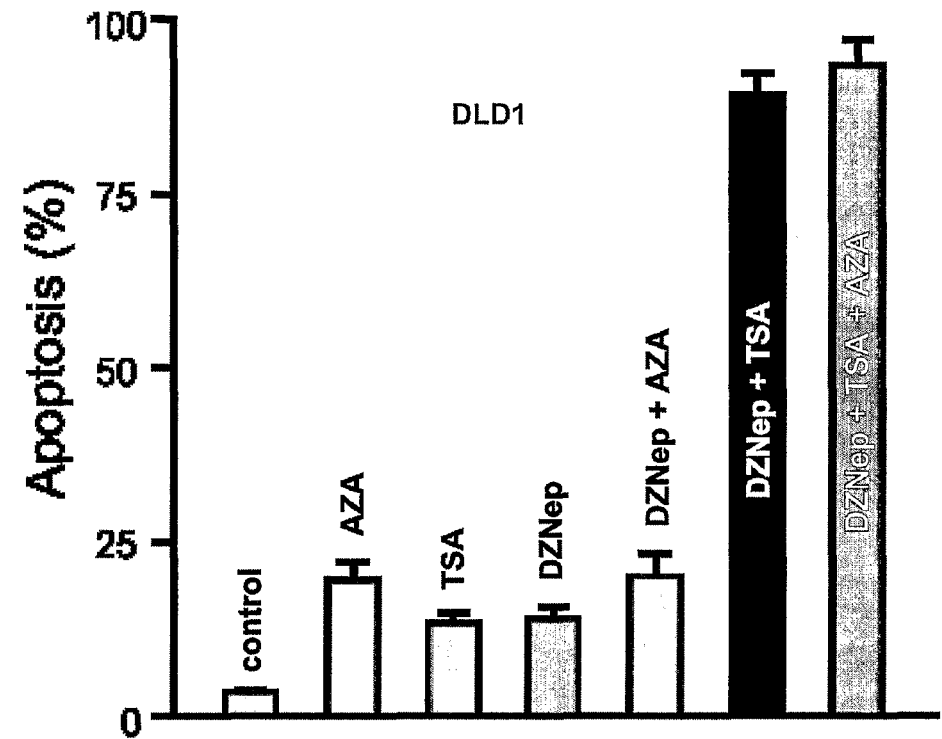
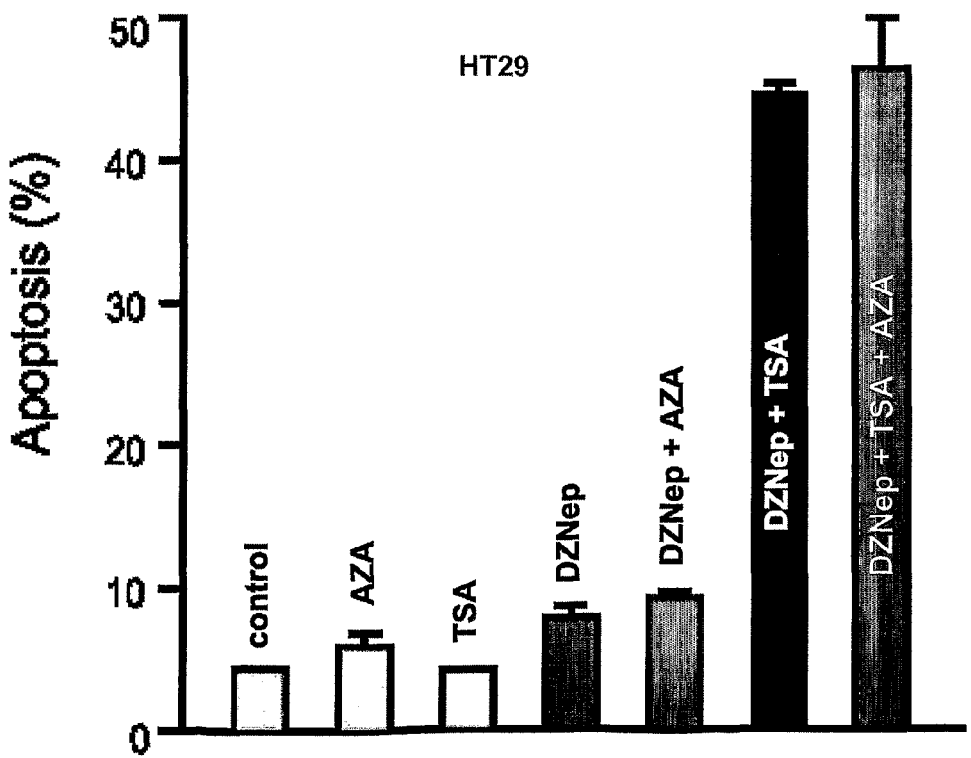

(cont. on next page)

(cont. on next page)

Fig. 8A
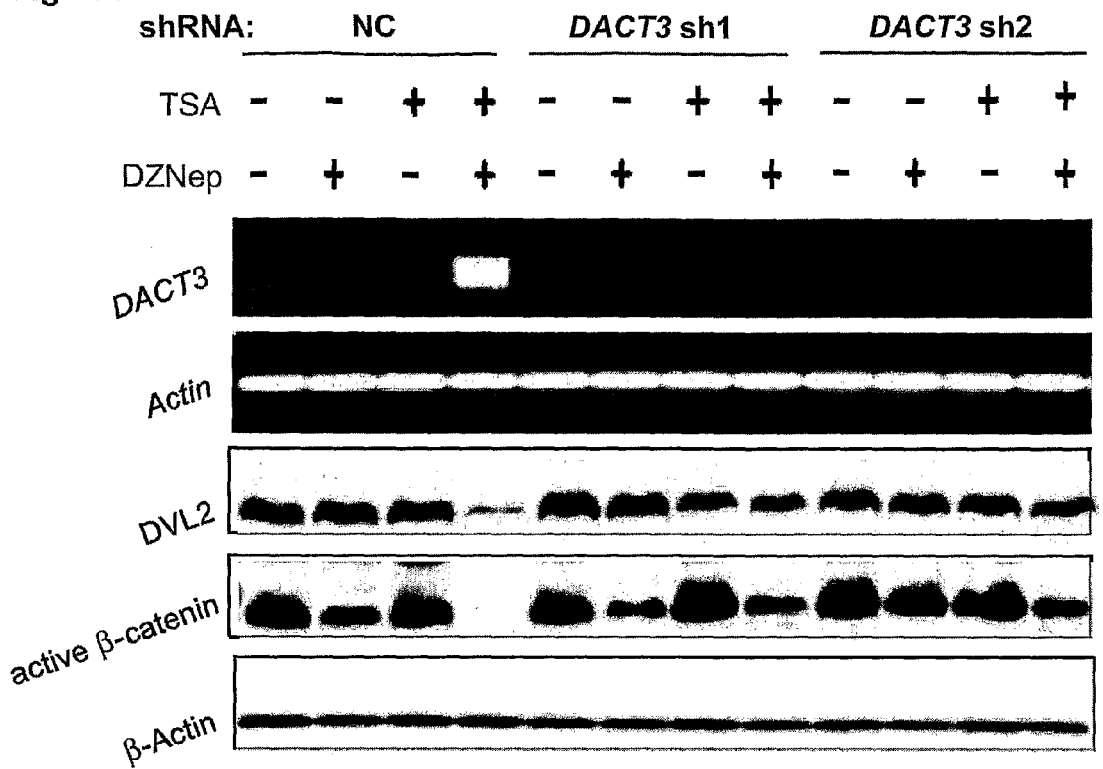
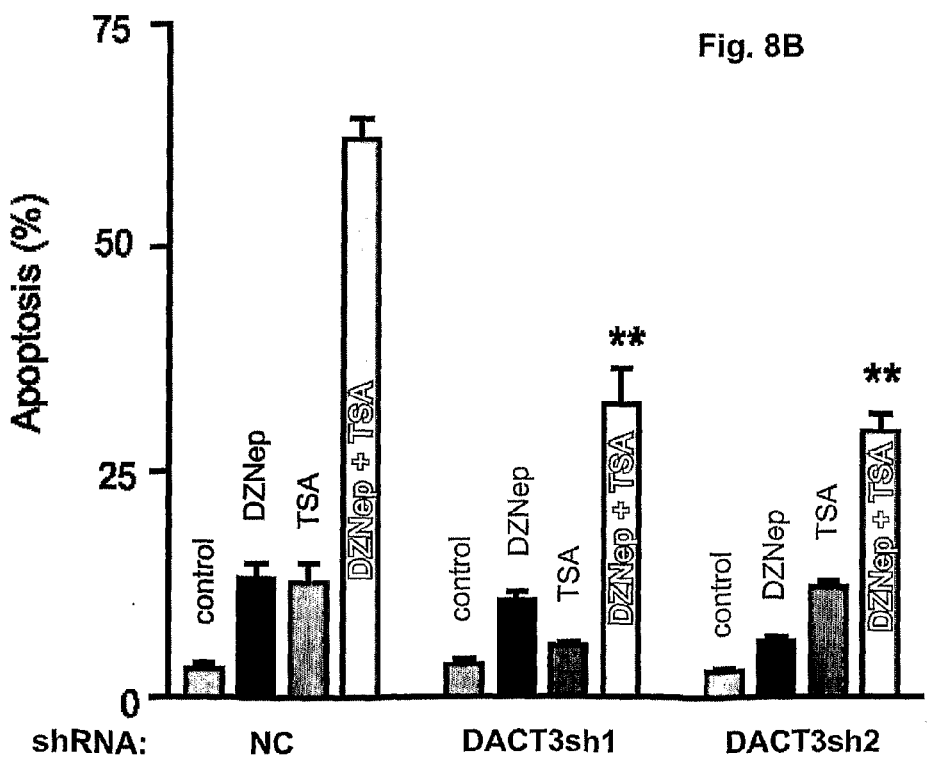
Fig. 8B

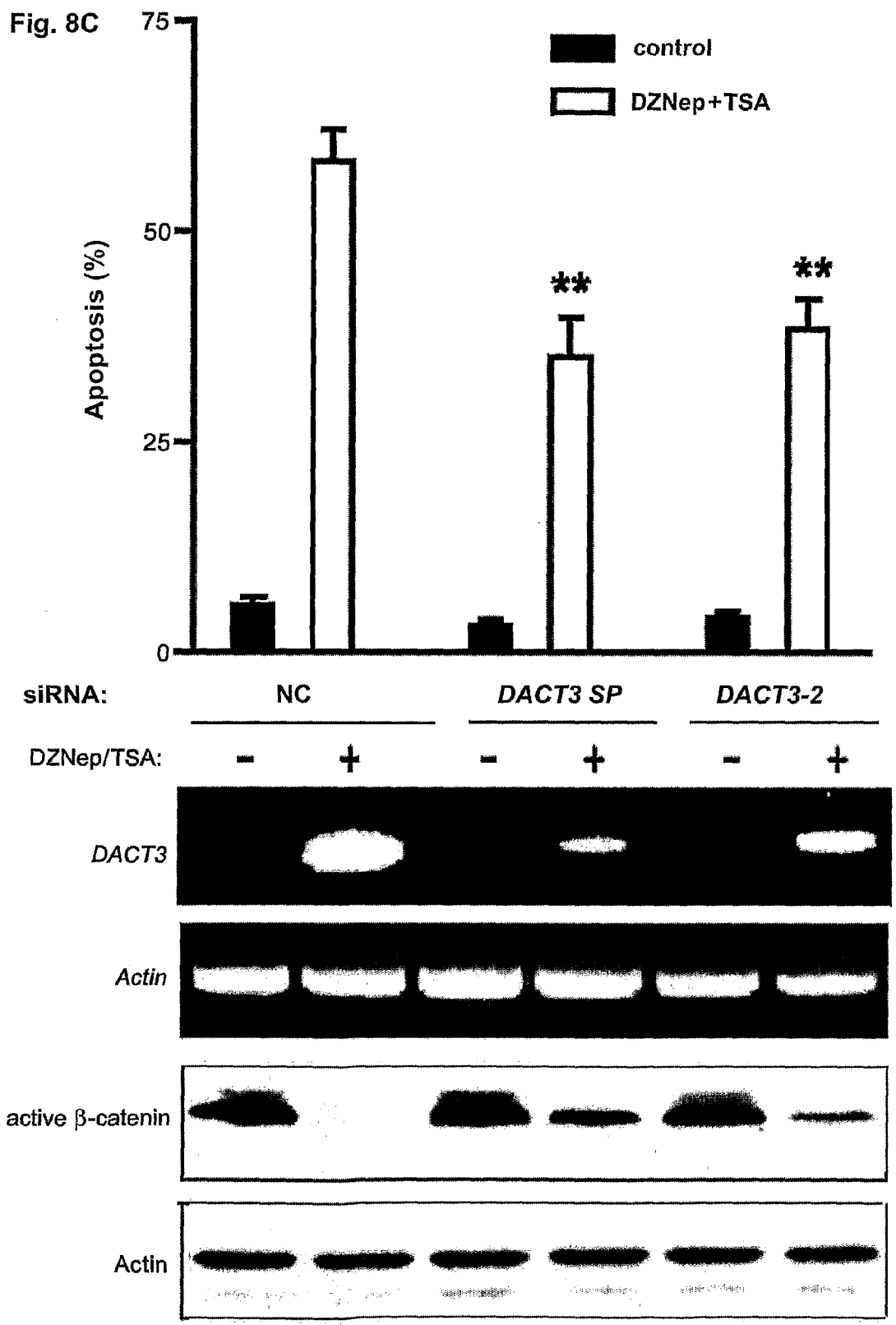

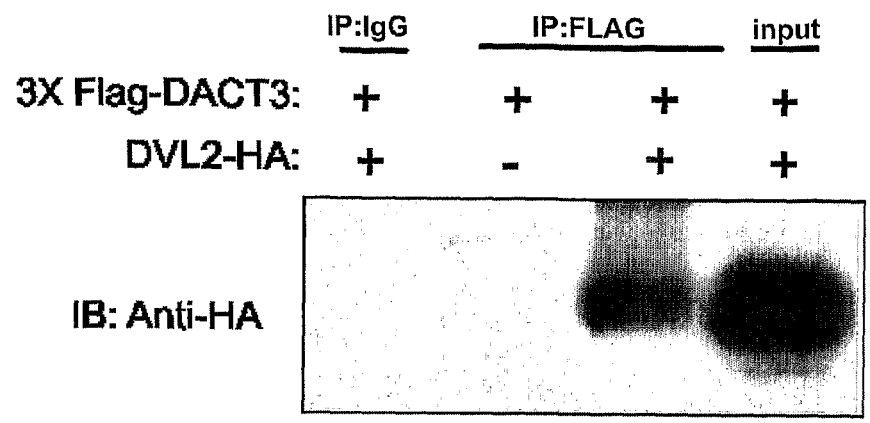
Fig. 9A
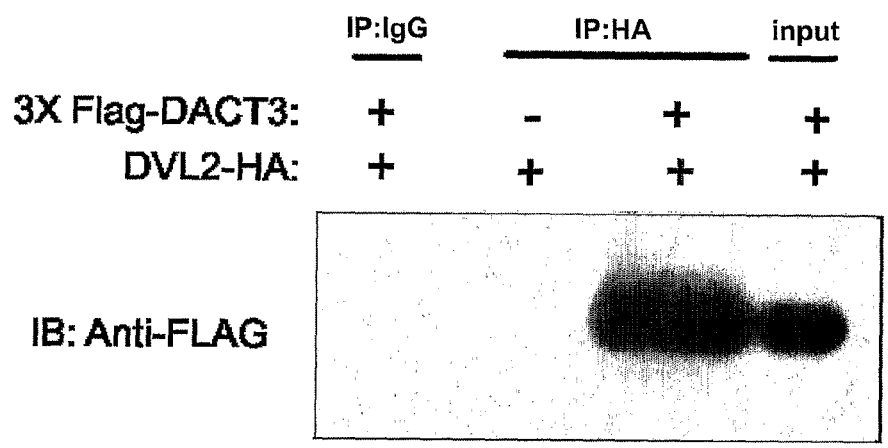
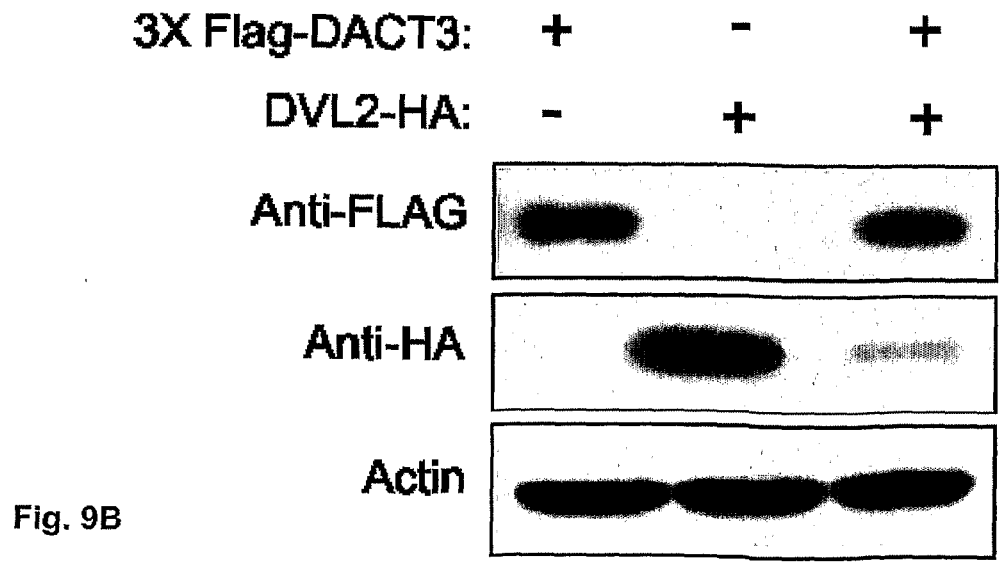
Fig. 9B

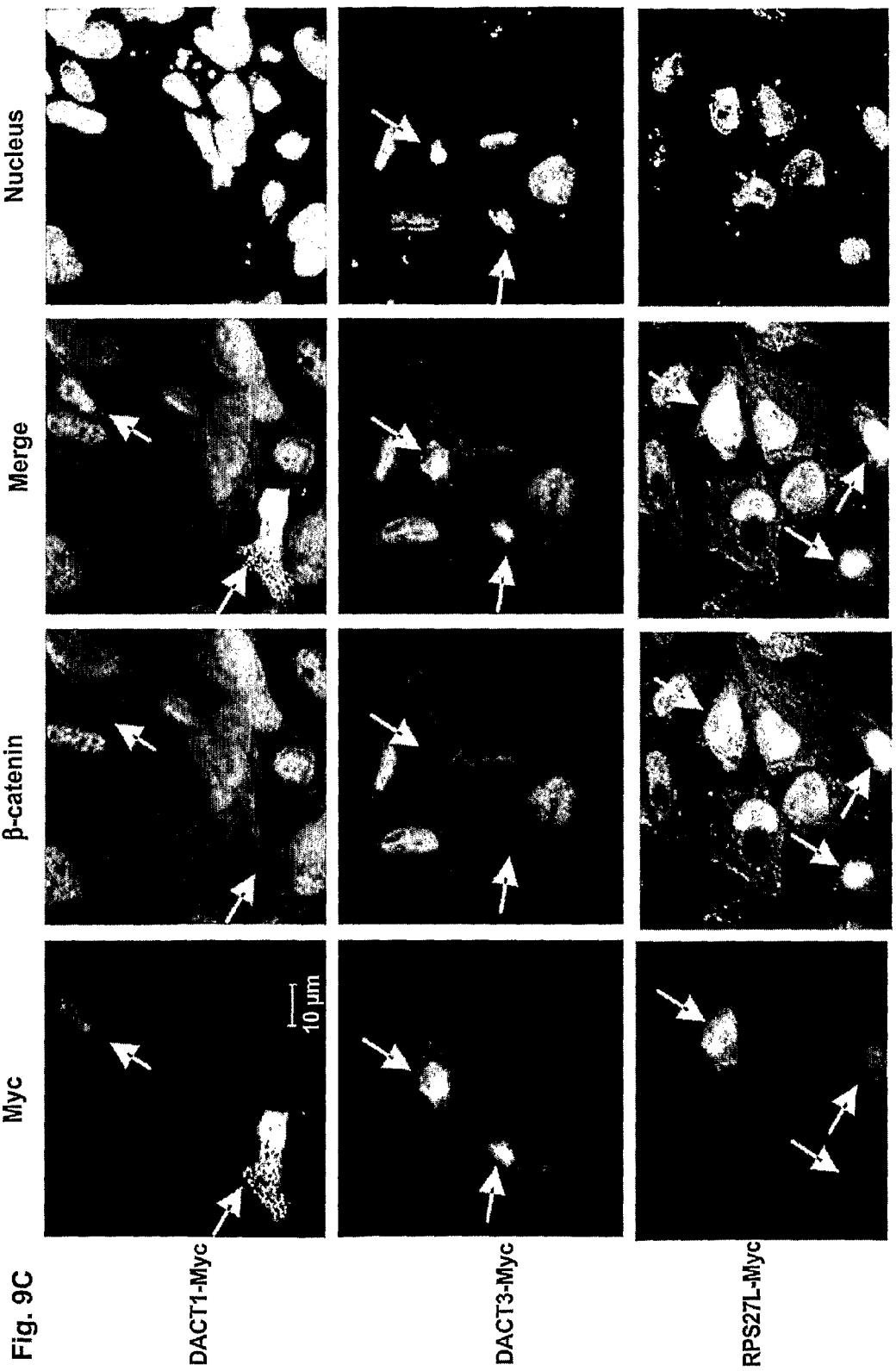

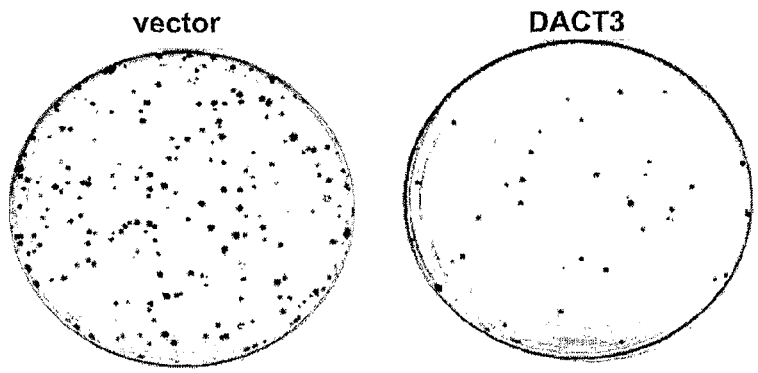
Fig. 9D
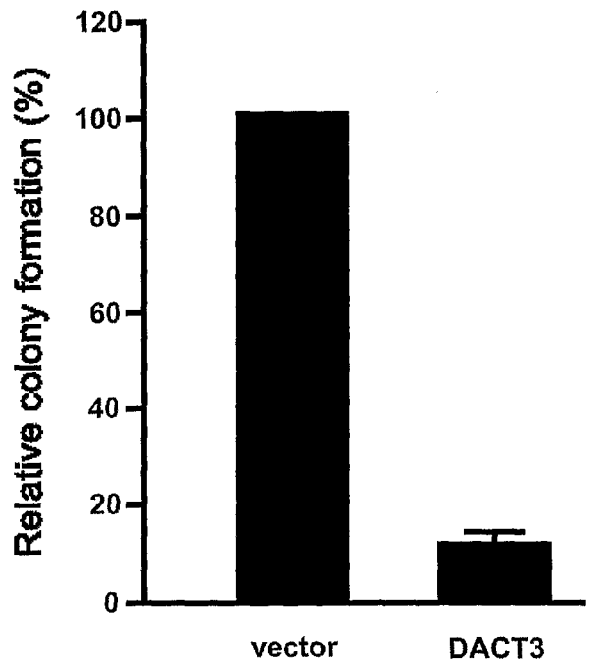
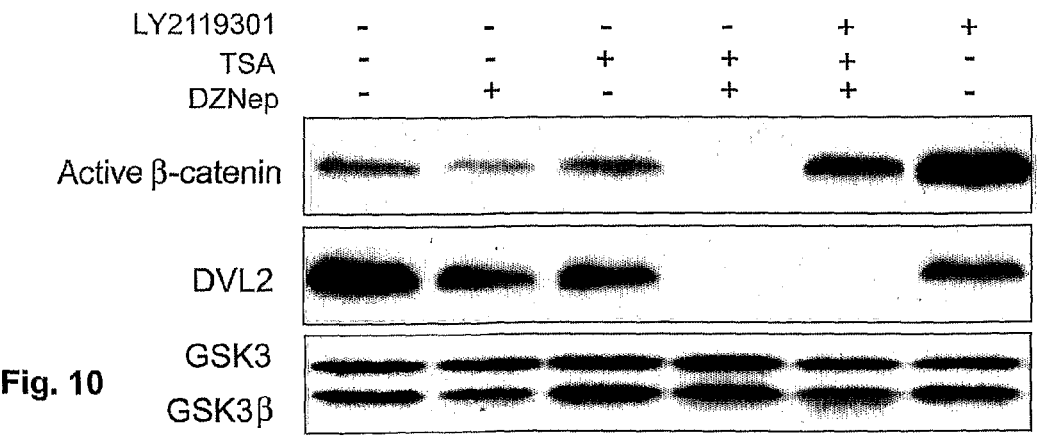
Fig. 10

Fig. 12

| | DLD1 control | DLD1 DZNep | DLD1 TSA | DLD1 DZNep+TSA | SW480 control | SW480 DZNep | SW480 TSA | SW480 DZNep+TSA | HT29 control | HT29 DZNep | HT29 TSA | HT29 DZNep+TSA |
|---|---|---|---|---|---|---|---|---|---|---|---|---|
| DACT3 | -3.7 | 20.6 | 18.2 | 1556.1 | 37.1 | 44 | 43.2 | 1444 | 0.8 | 22 | 16 | 1265 |
| CRYM | -7.7 | 4.5 | 123.8 | 315.9 | 1.3 | 71.3 | -5 | 84.1 | 52.9 | 45.4 | 35.5 | 291.3 |
| MMP9 | -12.6 | -13.9 | 51.7 | 266 | 32.1 | 371.3 | 97.2 | 227.9 | -19.1 | -10.1 | -16.3 | 147.8 |
| SCGB2A1 | 4.1 | 26 | 566 | 1054.6 | 48.4 | 346.4 | 14.7 | 403.2 | 7.1 | -0.6 | -7.3 | 586.6 |
| LOH11CR2A | -10.5 | -11.8 | 7.9 | 199.8 | -11.4 | -12.3 | -6.8 | 71.5 | 8.5 | -8.5 | -5.5 | 36.7 |
| MT3 | 2.6 | 10.6 | 343.3 | 420.9 | 174.8 | 874.8 | 60.9 | 600.8 | -5.1 | 5.5 | 11.6 | 139.9 |
| LDHD | 0.9 | -6.7 | 69 | 114.8 | -3.2 | 11.3 | -1.4 | 40.9 | -2.3 | -0.7 | -0.5 | 40 |
| PTGS1 | 1.4 | 95.4 | 34.9 | 92 | -10.7 | 322.9 | -11 | 452.5 | 812.5 | 689.5 | 622.6 | 3017.7 |
| THY1 | 0.4 | -1.6 | -2.1 | 65.7 | 3.8 | 6.2 | 38.3 | 606.7 | 2.7 | 2.4 | -4.4 | 165.5 |
| LILRB3 | -0.4 | 4.5 | 1.9 | 62.9 | -2.3 | 28.8 | 50.6 | 199.9 | -9.7 | -0.9 | -7.5 | 17.9 |
| SPP1 | -5.5 | 12.6 | 4 | 59.8 | -0.8 | 38.5 | 14.5 | 43.1 | 9.8 | 6.1 | 6.3 | 215.1 |
| COL1A1 | -5.5 | 7.3 | 8.3 | 59.2 | 11.8 | 22.3 | 23.2 | 43.8 | 20.7 | 33.4 | 19.8 | 153.6 |
| CLCNKA | 1.5 | 17.9 | 25.7 | 76.3 | 94.3 | 411.6 | 94.4 | 390.2 | 12.2 | 30.2 | 11.7 | 433.9 |
| NAT2 | 0.9 | 4.1 | 2.9 | 48.3 | 3.3 | 30.4 | 21.7 | 75.5 | -1.1 | 8.7 | -2.9 | 176.3 |
| HRC | -2.8 | 2.6 | 4.6 | 47.8 | -9.3 | 7 | -1.6 | 18 | 4.7 | -5.8 | 1.1 | 99 |
| IGFBP5 | 2.7 | 3.9 | 40.5 | 115.3 | 6 | 49.1 | 7.6 | 54.2 | -1.9 | -1.1 | -1.1 | 16.9 |
| KLK4 | -14.7 | -4.9 | 17 | 41.2 | 11.2 | 386.9 | 33.1 | 437.3 | 12.8 | 15 | 11.3 | 1186.8 |
| HLA-DRA | -6.7 | -3.1 | -7.4 | 40 | -4.6 | 61.2 | 5.6 | 61.1 | -11 | -5.9 | -7.6 | 32.2 |
| SERPINI1 | 36.8 | 129.8 | 175 | 1458.5 | 105.5 | 429 | 154 | 914.8 | 3.6 | 10.6 | 11.6 | 182.4 |
| GPR124 | -0.8 | 11.2 | 7.7 | 39 | 11.9 | 56.3 | 20.9 | 28.7 | -13.4 | 2.5 | 0.7 | 28.7 |
| GNG3 | -5.8 | 19.7 | 7.3 | 36.9 | 25.8 | 66.7 | 73 | 117.7 | 4.4 | 8 | 2.7 | 26.6 |
| TTLL6 | -4.7 | 3.7 | 19.9 | 32.5 | 16.1 | 73.3 | 10.7 | 42.4 | 2.5 | 5 | 13.9 | 45.4 |
| SHD | 16.3 | 46.2 | 39.8 | 496.1 | 30.6 | 184.2 | 27.2 | 581.8 | 35.1 | 34 | 39.4 | 134.3 |
| LDHD | -6.6 | 7.5 | 23.1 | 26.5 | 4 | 11.6 | 1.7 | 10.3 | 4.6 | 22.6 | -2 | 16.4 |
| KIR3DL2 | -13.4 | -9.6 | -6.2 | 22.3 | -1.7 | 10.1 | 1.8 | 37.6 | -9.9 | -7.7 | -12.3 | 12.4 |

Fig. 12 (continued)

| | DLD1 | | | | SW480 | | | | HT29 | | | |
|---|---|---|---|---|---|---|---|---|---|---|---|---|
| | control | DZNep | TSA | DZNep+TSA | control | DZNep | TSA | DZNep+TSA | control | DZNep | TSA | DZNep+TSA |
| HEY1 | 25.7 | 31 | 17.7 | 553.5 | 80.2 | 130.8 | 81.9 | 407 | 62.7 | 36.9 | 46.7 | 255.3 |
| STAT4 | 26.2 | 66.5 | 157 | 562.7 | -3.4 | 6.8 | -1.2 | 36.8 | 18.8 | 12.6 | 6.1 | 116.3 |
| DRD1IP | -4.1 | -9.8 | 1.6 | 19.6 | 1.7 | 184.2 | 5 | 77.2 | 18 | 7.7 | 13.8 | 47.8 |
| FAM46B | 37.3 | 55.2 | 145.1 | 718.3 | 329 | 165.6 | 468.7 | 2016 | -11.9 | -10 | 3.2 | 140.3 |
| MAP1A | 47.4 | 115.8 | 75.5 | 857.2 | 15.2 | 32 | 26.3 | 231.1 | 59.4 | 41.3 | 39.7 | 409.8 |
| SCNN1G | 2.3 | 6.1 | 7.8 | 38.1 | 4.3 | 11.1 | 9.4 | 132.5 | 6.2 | -7.8 | 4.2 | 20.5 |
| TAGLN3 | 2.9 | 0.8 | 5.9 | 46.4 | 8.6 | 16.1 | 23.9 | 47.1 | 4.4 | 3.5 | -7.2 | 36.7 |
| DENND2C | 118.2 | 211.6 | 102.1 | 1883.2 | 253.5 | 263.4 | 208.5 | 673.7 | 14 | 20.3 | 34.9 | 206.2 |
| DNALI1 | -7.1 | -9 | -8.1 | 14.9 | -11.9 | -13.5 | -9.4 | 8.7 | 37.9 | 138.3 | 31.6 | 105.6 |
| CSF1R | 3.5 | -7.2 | 17 | 51 | 2.3 | 14.2 | 4 | 30.6 | -7.2 | -1.9 | -10.7 | 45.1 |
| SCARF2 | 6.4 | 6.2 | 20.7 | 88.2 | 4.6 | -7.8 | -0.7 | 17.7 | -5.1 | 1.1 | 1.6 | 20.1 |
| TSPAN7 | 58.4 | 329.4 | 290.4 | 784.1 | 10.5 | 84.3 | 12.7 | 111.7 | -7.8 | -7 | 6.1 | 183.4 |
| HLA-DPA1 | -15.1 | -13.2 | -5.5 | 12.3 | -7.4 | 14.3 | 1.3 | 20.2 | -9.4 | -17.9 | -6.7 | 39.4 |
| SOCS1 | 15.2 | 36.5 | 30.9 | 155.7 | 10.9 | 18.3 | 49.5 | 56.5 | 6.5 | 6.8 | 12.5 | 39.8 |
| NRXN2 | 27.1 | 50.2 | 77.4 | 275.2 | 15.5 | 164 | 13.8 | 117.2 | 22.4 | 15.9 | 15.2 | 103.6 |
| ABAT | 20.7 | 20.3 | 33.3 | 197.6 | 39.4 | 57.3 | 167.9 | 113.5 | 8.1 | 6.7 | 6.7 | 40.4 |
| FLJ90650 | 21.8 | 96.5 | 16.9 | 204.6 | 12.2 | 25 | 41 | 152.5 | 6.9 | 10.9 | 6.8 | 30.1 |
| NRGN | 284.8 | 438.7 | 739 | 2528.3 | 166.3 | 562 | 213 | 962.7 | 526.8 | 425.7 | 393.2 | 3001.9 |
| FNDC1 | -6.8 | -3.9 | -0.7 | 8.7 | -0.7 | 9.5 | 2.1 | 4.9 | -10.3 | 12.5 | -5.9 | 7.4 |
| SLC39A3 | 241.5 | 874.2 | 146.3 | 1933.5 | 45.3 | 29.2 | 420 | 833.6 | 153.2 | 93.7 | 135.9 | 458 |
| SYT11 | 25.6 | 23.6 | 21.4 | 203.6 | 11.6 | 39.7 | 10.7 | 137.9 | 24.4 | 8.1 | 19.1 | 87.2 |
| PRG1 | 1.6 | 5.7 | -8.9 | 12.7 | -10.4 | 1.3 | 8.2 | 2.5 | 1.5 | -4.5 | 4.2 | 27.1 |
| RASSF5 | 30.6 | 266.3 | 36.5 | 232.2 | 24.9 | 27.2 | 187.5 | 147.6 | 8.6 | 17.6 | 17.1 | 102 |
| FLJ20701 | 30.6 | 55.1 | 10.6 | 229.5 | -7.6 | -6.2 | -4.4 | 6.6 | -15.2 | -6.4 | -13.2 | 0.5 |
| SMPD1 | 74.9 | 73.2 | 237.4 | 560.3 | 97.5 | 139.3 | 125.8 | 257.9 | 36.4 | 22.6 | 39.2 | 140.1 |
| FLJ10260 | -8.7 | 4.8 | -8.3 | 6.6 | 7.4 | 4.2 | 13.9 | 41.1 | -3.2 | 3 | -4.5 | 15.6 |

Fig. 12 (continued)

| | DLD1 | | | | SW480 | | | | HT29 | | | |
|---|---|---|---|---|---|---|---|---|---|---|---|---|
| | control | DZNep | TSA | DZNep+TSA | control | DZNep | TSA | DZNep+TSA | control | DZNep | TSA | DZNep+TSA |
| SPINK2 | 20.2 | 11.5 | 309.6 | 125 | 8.8 | 130 | 4 | 53.8 | -4.5 | 30.6 | 18.8 | 390.4 |
| SEPP1 | 488.6 | 686.8 | 947.3 | 3000.9 | 31.9 | 264.8 | 38.5 | 200.3 | 76.9 | 43.3 | 35.5 | 881.4 |
| COX7A1 | -0.2 | 4.6 | -0.2 | 6.1 | 4.1 | -1.5 | 8.5 | 8.9 | 0.7 | 1.8 | -0.7 | 8.4 |
| FBXL2 | 122.7 | 186.1 | 216.9 | 702.2 | 167.4 | 263.9 | 180.6 | 438.5 | -0.1 | 0.6 | 8.1 | 8.5 |
| SH2D3C | 21.6 | 28 | 25.9 | 118.9 | 16.1 | 23.4 | 13.9 | 91.5 | 26.7 | 8.7 | 23.5 | 74.4 |
| ISLR2 | -5.4 | -11.2 | -4.6 | 5.5 | -1.2 | 15.6 | 46.9 | 30.3 | -14.1 | -2.9 | -2.7 | 7.4 |
| CLC | 13.4 | 2.2 | 23.6 | 73.5 | 15.2 | 1095.3 | 101 | 552.9 | 4.4 | -0.8 | 9.1 | 23.8 |
| HIST1H2BD | 15.1 | 28.3 | 6 | 82.5 | 48.6 | 84.6 | 163.9 | 994.4 | 37.3 | 30.6 | 36.7 | 191 |
| GAL3ST4 | 31.9 | 49.6 | 35.7 | 164 | 55.3 | 93.2 | 31.5 | 123.5 | 48.6 | 30.7 | 35.5 | 145.4 |
| MAP4K1 | 117.2 | 209.6 | 318.6 | 593 | 120.9 | 469.3 | 175.7 | 552.7 | 19.4 | 39.6 | 30.4 | 835.8 |
| STARD5 | 155.5 | 169.8 | 64.9 | 755.9 | 78.1 | 86.2 | 146.5 | 422.2 | 29.6 | 34.9 | 24.1 | 90.4 |
| VAV1 | 4.9 | 15.8 | 6.7 | 23 | 7.7 | 15.1 | 11.9 | 30.1 | 5 | 37.2 | 11.3 | 43.3 |
| CCBP2 | 35.7 | 26.1 | 109.9 | 162.8 | 11.4 | 67.5 | 11.5 | 67.4 | -6.6 | 5.6 | -2.5 | 22.9 |
| ANKRD35 | 4.2 | -0.5 | 10.8 | 19 | 16.1 | 12.3 | 7.8 | 56.3 | 3.7 | 22.7 | 23.5 | 14.5 |
| CRI1 | 121.6 | 342.5 | 160.6 | 524.5 | 70.9 | 90.8 | 251.9 | 154.3 | 63.5 | 32.1 | 37.1 | 361.5 |
| SYP | 21 | 5.9 | 40.3 | 89.5 | 41.3 | 125.5 | 32 | 121.2 | 20.6 | 19.1 | 17.9 | 89.9 |
| CD163 | 12.3 | 31.5 | 36.7 | 51 | -4.7 | 5.1 | 1.5 | 36.1 | -0.8 | 5.2 | 19.4 | 21.2 |
| PML | 3.2 | -2.2 | 11.5 | 13.2 | 12.1 | 4.4 | 15.6 | -0.6 | 7.2 | 16.5 | 11.5 | 21.5 |
| FABP4 | 14.8 | 18 | 18.2 | 59.5 | 9.4 | 47 | 13.1 | 88.7 | 19.2 | 24.3 | 34.7 | 137 |
| CD33 | 4.3 | 18.7 | 5.2 | 17 | 19.1 | 61.1 | 86.9 | 48.7 | 14 | 15.8 | 3.3 | 83.1 |
| SGCA | 3.3 | 3.1 | 7.4 | 12.2 | 2.6 | 10.2 | 8 | 11.2 | 6.4 | 10.7 | 13 | 23.4 |

Fig. 12 (continued)

| | DLD1 | | | | SW480 | | | | HT29 | | | |
|---|---|---|---|---|---|---|---|---|---|---|---|---|
| | control | DZNep | TSA | DZNep+TSA | control | DZNep | TSA | DZNep+TSA | control | DZNep | TSA | DZNep+TSA |
| POU2F2 | 89 | 121.9 | 189.8 | 326.9 | 51 | 69.5 | 84.1 | 233.7 | 129 | 89.2 | 70.7 | 362.6 |
| ZNF491 | 4.8 | -1.9 | 17.3 | 17 | 25.6 | 101 | 74.1 | 114.9 | 12.1 | 7.7 | 16.8 | 46.5 |
| VWF | 39.6 | 126.7 | 380.1 | 138.7 | 103.2 | 382.1 | 295.7 | 271.9 | -2.7 | 0.2 | -3.9 | 89.3 |
| C20orf160 | 81.8 | 7.7 | 30.4 | 276.5 | 44 | 432.2 | 9.7 | 357.7 | -5.7 | -7.5 | -6.5 | 195.4 |
| SLC6A12 | 9 | 28.5 | 30.5 | 30.3 | 4.1 | 23.1 | 7.2 | 14.3 | 25.8 | 26.3 | 31.3 | 141.4 |
| HIST1H4H | 101.2 | 222.4 | 119.7 | 333.4 | 488.3 | 1934.4 | 1090.5 | 10720 | 43 | 48.5 | 40.2 | 624.8 |
| PLVAP | 9.5 | 15.7 | 6.8 | 31 | 7.4 | 6.4 | 3.8 | 17.8 | 10 | 14.3 | 8.2 | 28 |
| CLEC4A | 38.4 | 87.5 | 20.7 | 118.2 | 16.6 | 5 | 52.5 | 90.5 | 9 | 5.7 | 6.2 | 69.8 |
| KIAA0319 | 52.4 | 69.5 | 70.6 | 153.7 | 10.7 | 23.4 | -7.4 | 32.6 | 9.6 | 7.6 | 30.1 | 67.9 |

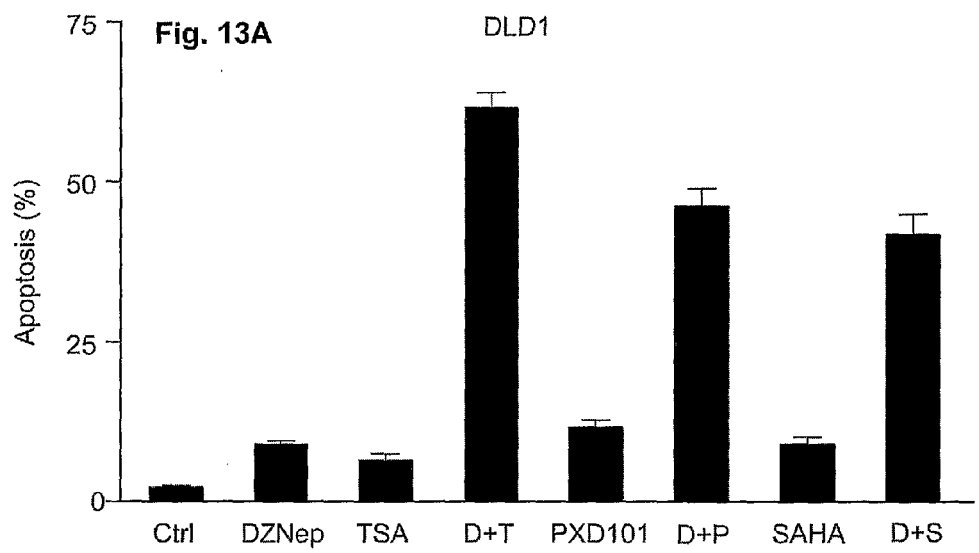
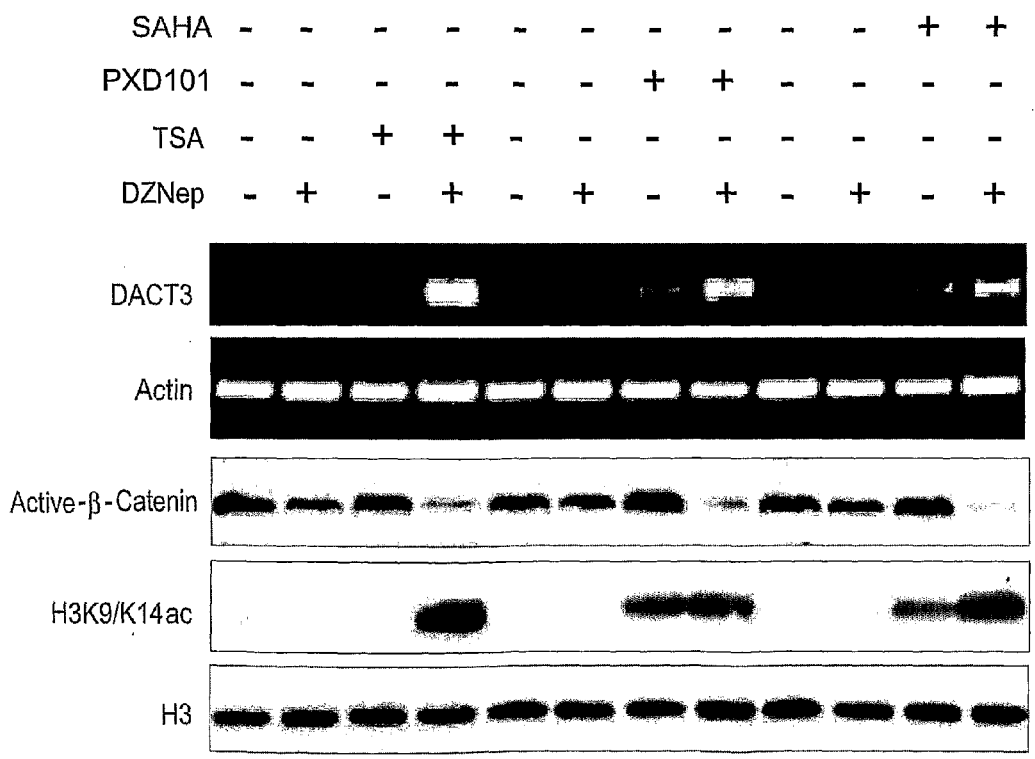

| Treatment | n | TRD | NTRD | TGI Day 3 A) on Mean B) on Median | TGI Day 7 A) on Mean B) on Median | TGI Day 10 A) on Mean B) on Median | TGI Day 14 A) on Mean B) on Median |
|---|---|---|---|---|---|---|---|
| Vehicle (Saline i.p. 3x/w+MC/ Tween q.d. p.o.) | 7 | 0 | 0 | - - | - - | - - | - - |
| SAHA (200 mg/kg q.d. p.o.) | 7 | 1 | 1 | 15% 28% | 23% 8% | 56% 41% | 55% 47% |
| DZNep (5 mg/kg i.p. 3x/w) | 7 | 0 | 0 | 5% 66% | 10% 53% | 6% 13% | 0% 0% |
| DZNep+SAHA (200 mg/kg q.d. p.o., 5 mg/kg i.p. 3x/w) | 7 | 0 | 0 | 77% 47% | 69% 65% | 85% 79% | 83% 75% |

Fig. 18

METHODS AND COMPOUNDS FOR PREVENTING AND TREATING A TUMOUR

CROSS-REFERENCE TO RELATED APPLICATIONS

This application makes reference to and claims the benefit of priority of an application for "Methods And Compounds For Preventing And Treating A Tumour" filed on Jun. 6, 2008 with the United States Patent and Trademark Office, and there duly assigned Ser. No. 61/059,482 as well as an application "DACT3 Is A Key Epigenetic Regulator Of Wnt/β-catenin Signaling In Colorectal Cancer And Is A Therapeutic Target Of Histone Modifications" filed on Nov. 2, 2007 with the United States Patent and Trademark Office, and there duly assigned Ser. No. 60/984,835. The contents of said two applications are incorporated herein by reference for all purposes, including an incorporation of any element or part of the description, claims or drawings not contained herein and referred to in Rule 20.5(a) of the PCT, pursuant to Rule 4.18 of the PCT.

SEQUENCE LISTING

The instant application contains a Sequence Listing which has been submitted in ASCII formate via EFS-Web and is hereby incorporated by reference in its entirety. Said ASCII copy, created Oct. 27, 2010, is named 33946265.txt and is 28,013 bytes in size.

FIELD OF THE INVENTION

The present invention provides methods and compounds for preventing and treating a tumor. Also provided are a method of inducing apoptosis in a tumour cell and a method of diagnosing the risk of developing a neoplasm in a subject.

BACKGROUND OF THE INVENTION

Cancer is a major cause of death worldwide, being the second-leading cause of death in developed countries and even the number one cause of death in e.g. Australia, Japan, Korea, Singapore and the male population of the UK and Spain. The number of people who develop cancer each year is increasing.

Currently, cancer therapy involves surgery or focuses on the functional or genetic changes associated with the transformation of cells into malignant cells. An ideal anti-cancer drug should selectively kill, or at least inhibit, rapidly proliferating cancerous cells, while leaving non-cancerous cells unaffected. Recent approaches include immunotherapy using antibodies directed to markers of selected types of cancer cells (e.g. US patent application 2005/0244417), the application of agonists to receptors that are expressed on certain types of cancer cells (US patent application 2006/0147456), the application of interferon-containing chitosan-lipid particles (US patent application 2005/0266093), as well as the application of a compound that acts as a cytotoxic agent for a certain type of prostate cancer cells by an unknown mechanism (US patent application 2005/0245559).

A further approach on which research efforts have recently been undertaken is the development of an epigenetic cancer therapy, since abnormal patterns of DNA methylation in cancer cells are known for more than 20 years (for an overview see e.g. Brown, R. and Strathdee, G., *Trends in Molecular Medicine* (2002) 8, 4 (Suppl.), S43-S48, or Yoo, C. B. and Jones, P. A., *Nature Reviews Drug Discovery* (2006) 5, 1, 37-50). Nevertheless only two DNA methyl-transferase inhibitors, 5-azacytidine (Vidaza®) and decitabine (Dacogen®) have made it to the market. They have been approved for the treatment of myelodysplastic syndrome, a haematological condition also known as "preleukemia". There is therefore still a need in the art for novel compounds and compositions for treating or preventing cancer or neoplastic disease that preferentially rapidly kill cancerous cells.

Accordingly it is an object of the present invention to provide a method, as well as compounds and compositions that are capable of preferentially killing a cancer cell without affecting a non-cancerous cell. It is a further object of the invention to provide a method of diagnosing the risk of tumourigenesis.

SUMMARY OF THE INVENTION

In a first aspect the present invention provides a method of preventing, inhibiting, arresting or reversing tumourigenesis in a cell. The method includes increasing the amount and/or the activity of a DACT ("dapper, antagonist of beta-catenin, homolog") protein, or a functional fragment thereof, in the cell.

In a second aspect the invention provides a method of inducing apoptosis in a tumour cell. The method includes increasing the amount and/or the activity of a DACT protein, or a functional fragment thereof, in the cell. Generally apoptosis is preferentially induced in a tumour cell, while non-tumour cells remain largely unaffected. In some embodiments apoptosis is selectively induced only in a tumour cell, while non-tumour cells remain unaffected.

In a third aspect the invention provides a pharmaceutical composition. The pharmaceutical composition includes a combination of the following two compounds: The first compound is a compound of the general formula (I)

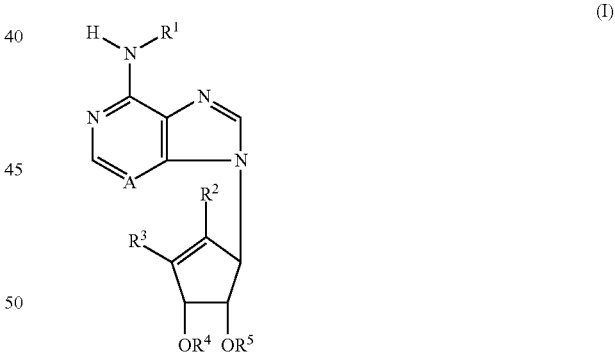

In formula (I) A is CH or N. $R^1$, $R^4$ and $R^5$ are independent from each other H, an aliphatic group, an alicyclic group, an aromatic group, an arylaliphatic group, and an arylalicyclic group, which may optionally include 0-3 heteroatoms. The heteroatoms may be N, O, S, or Si. $R^4$ and $R^5$ may optionally be linked so as to define an aliphatic hydrocarbyl bridge. $R^2$ is H or a halogen such as F, Cl, Br or I. $R^3$ is H, or an aliphatic or arylaliphatic group that includes 1-8 main chain carbon atoms and 0-3 heteroatoms. The heteroatoms may be N, O, S, Si, or a halogen, e.g. Cl, F, Br or I. In some embodiments, $R^2$ is F or Cl. In some embodiment, also $R^3$—independently or at the same time as $R^2$—can also be F or Cl. The second compound is a histone deacetylase inhibitor, such as e.g. a hyroxamic acid compound, a cyclic tetrapeptide, a benzamide, an electrophilic ketone, SAHA (Vorinostat®), PXD101 (Belinostat®), MS275, LAQ824/LBH589, CI994, MGCD0103 or a sirtuin inhibitor.

In a fourth aspect the invention provides the use of a compound of general formula (I) in the treatment of a bowel tumor, including a rectal tumor and a colon tumor. In this regard the invention also relates to the use of a compound of general formula (I) in the manufacture of a medicament for the treatment of a bowel tumor, e.g. bowel cancer.

In a fifth aspect the invention provides a method of diagnosing the risk of tumourigenesis in a cell. The method includes assessing one or more of (i) the amount of a DACT protein in the cell, (ii) the activity of the DACT protein in the cell, and (iii) the pattern of a posttranslational histone modification. This posttranslational histone modification is typically histone methylation and/or histone acetylation.

In a sixth aspect the invention relates to a method of predicting whether a neoplasm is sensitive to a combination of a compound of the general formula (I) and a histone deacetylase inhibitor. The method includes assessing one of (i) the amount of a DACT protein, (ii) the activity of a DACT protein, and (iii) the pattern of a posttranslational histone modification in the neoplasm. In assessing the amount of the DACT protein a reduced amount thereof is an indication that the neoplasm is sensitive to a combination of a compound of the general formula (I) and a histone deacetylase inhibitor. In assessing the activity of the DACT protein a reduced activity thereof is an indication that the neoplasm is sensitive to a combination of a compound of the general formula (I) and a histone deacetylase inhibitor. In assessing the pattern of a posttranslational histone modification, an alteration thereof an altered posttranslational histone modification is an indication that the neoplasm is sensitive to a combination of a compound of the general formula (I) and a histone deacetylase inhibitor. The pattern of a posttranslational histone modification may for example be modified at the gene locus of a DACT protein.

In a seventh aspect the invention relates to the use of a nucleic acid molecule and/or a low molecular weight organic molecule that increases the amount, i.e. the absolute quantity, of a DACT protein in a cell in the manufacture of a medicament for preventing or treating a tumour.

In a eighth aspect the invention provides a method of identifying a candidate compound that is capable of preventing tumourigenesis in a cell and/or of inducing apoptosis in a tumour cell. The method includes introducing the compound into a cell that is capable of expressing a DACT protein, or a functional fragment thereof. Further the method includes determining the expression of the DACT protein. An increased expression of the DACT protein is an indication that the compound is capable of preventing tumourigenesis in a cell and/or of inducing apoptosis in a tumour cell.

In a ninth aspect the invention provides an in-vitro method of identifying a compound capable of preventing tumourigenesis in a cell and/or of inducing apoptosis in a tumour cell. The method includes contacting the compound, a DACT protein, or a functional fragment thereof, and a dishevelled protein. An enhancement of the formation of a complex between the DACT protein and the dishevelled protein indicates that the compound is capable of preventing tumourigenesis in a cell and/or of inducing apoptosis in a tumour cell.

BRIEF DESCRIPTION OF THE DRAWINGS

The invention will be better understood with reference to the detailed description when considered in conjunction with the non-limiting examples and the accompanying drawings.

FIG. 9 illustrates the effects of heterologously overexpressing DACT3 on Dvl2 and β-catenin in colorectal cancer cells by means of Western blot (A, B) immunofluorescent imaging (C) and cell growth (D).

FIG. 10 shows the effect of GSK-3 inhibition (LY2119301) on β-catenin levels in presence and absence of DZNep/TSA.

FIG. 12 lists genes reactivated by DZNep/TSA treatment in cancer cells.

FIG. 13 illustrates synergistic effects of DZNep with further histone deacetylase inhibitors in inducing apoptosis (A), and inducing DACT3 and inhibiting β-catenin (B).

FIG. 18 is a table summarizing the tumor growth inhibition in vivo during treatment with DZNep and SAHA

DETAILED DESCRIPTION OF THE INVENTION

Figure 1A:
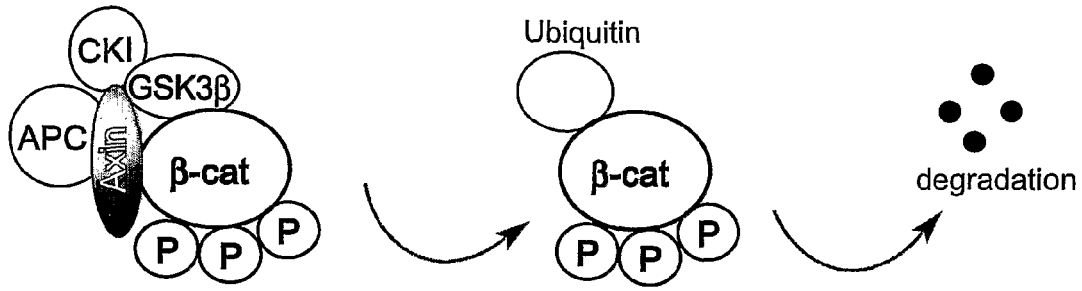
FIG. 1 is a simplified schematic of features of the Wnt/β-catenin pathway. Without a Wnt signal β-catenin is being degraded (A). Upon activation of Wnt/β-catenin signalling Dvl binds to the Frz receptor, whereby β-catenin is allowed to enter the nucleus and activate transcription (B). In embodiments of a method of the invention Dvl is expected to form a complex with a DACT protein, thereby reverting to the state of FIG. 1A (C).

The present invention is based on the finding that DACT proteins, and in particular DACT3, act as negative regulators of Wnt/β-catenin signaling. The family of DACT proteins, in various organisms also named Dapper (Dpr), Frodo, (Frd), THYEX3, HNG3, and MTNG3, is currently known to include 3 members, named DACT1 to DACT3 (Fisher, D. A., et al., *Developmental Dynamics* (2006) 235, 2620-2630). DACT3 includes for example the proteins of the UniProtKB/Swiss-Prot accession Nos Q96B18 (human), Q0PHV7 (mouse), the NCBI accession No AAH16161 (human), the UniProtKB/TrEMBL accession No A8IP73 (mouse) or a protein encoded by the nucleic acid molecules of NCBI accession Nos NW_001838496 (human), NM_145056 (human), NM_145056 (*Xenopus laevis*), XR_027789 (bovine), NW_001084763 (rat), NW_047556 (rat), NM_001081655 (mouse), NW_001030832 (mouse), DQ832319 (mouse), or NW_876270 (dog). DACT2 includes for example the proteins of the UniProtKB/Swiss-Prot accession Nos Q673G8 (zebrafish), Q5SW24 (human), or Q7TN08 (mouse), the UniProtKB/TrEMBL accession No Q4V9Q8 (zebrafish) or a protein encoded by the nucleic acid molecules of NCBI accession Nos BC111790 (human), BC111764 (human), BC092498 (human), NM_001077794 (zebrafish), NM_001107464 (rat), NW_001236578 (chimpanzee), XM_001145122 (chimpanzee), BV677538 (Rhesus macaque), AC_000039 (mouse), NM_172826 (mouse), NW_001030598 (mouse), NT_039649 (mouse) or BC058740 (mouse). Two alternatively spliced transcripts, termed α and β, of the HDPR1 gene, encoding human DACT1 have been identified (Yau, *Oncogene* (2005) 24, 1607-1614).

The terms "signalling" and "signal transduction pathway" refer to cellular mechanisms and to molecules that act on cellular components in response to a certain condition or change. Typically such mechanisms and molecules propagate an extracellular signal through the cell membrane to become an intracellular signal. This signal can then stimulate a cellular response. A "Wnt signaling pathway component" typically is a component that transduces a signal originating from an interaction between a Wnt protein and an Frz receptor and/or between a Wnt protein and an LRP protein (LDL-related receptor protein), e.g. LRP5 or LRP6. As the Wnt signaling pathway is complex, and involves extensive feedback regulation, there are numerous and likely not yet discovered members of the Wnt signaling pathway. Exemplary Wnt signaling pathway components include the (at least temporarily) membrane associated proteins Axin and Dishevelled, the extracellular Wnt interactive proteins sFRP, WIF-I, the LRP inactivating proteins Dkk and Krn, the cytoplasmic protein β-catenin, members of the β-catenin "degradation complex" APC, GSK3β, CKIα and PP2A, the nuclear transport proteins APC, pygopus and bcl9/legless, and the transcription factors TCF/LEF, Groucho and various histone acetylases such as CBP/p300 and Brg-1.

Members of the DACT (Dpr/Frodo) gene family have been shown to be involved in Wnt/β-catenin signaling by interacting with Dishevelled (Dvl) (Cheyette, B. N., et al., *Dev Cell* (2002) 2, 449-461), a cytosolic scaffold protein that is a central component of Wnt signaling (Bilic, J., et al., *Science* (2007) 316, 1619-1622; Logan, C. Y., & Nusse, R., *Annu Rev Cell Dev Biol* (2004) 20, 781-810). DACT 1 has been shown to form a complex with Dvl by binding to the Dvl PDZ domain via a conserved C-terminal PDZ-binding motif (Cheyette et al., 2002, supra; Wong, H.-C., et al., *Molecular Cell* (2003) 12, 5, 1251-1260). Published data suggest that a PDZ binding peptide of DACT1 can compete with the Frizzled receptor for the same site of Dvl-1 (Wong, et al., 2003, supra). An exact role of the DACT proteins has however so far not been established. Some data appear to indicate that DACT1 and DACT2 antagonize Wnt signaling in some biological contexts, while other data seem to indicate that they may activate Wnt signaling in other biological contexts, and that they may also play roles in TGF-β/Nodal signaling (Gloy, J., et al., *Nat Cell Biol* (2002) 4, 351-357; Hikasa, H., & Sokol, S. Y., *Development* (2004) 131, 4725-4734; Su, Y., et al., *FASEB J* (2007) 21, 682-690; Zhang, L., et al., *J Biol Chem* (2006) 281, 8607-8612; Zhang, L., et al., *Science* (2004) 306, 114-117; Bikkavilli, R. K., et al. *Journal of Cell Science* (2008), 121, 2, 234-245). After the priority date of the present application DACT1 has been reported, independently from the present invention, to control Wnt/β-catenin signaling by preventing the formation of a complex of β-catenin with the transcription factor lymphoid enhancer factor 1 (LEF1) and by enhancing the interaction between LEF1 and histone deacetylase 1 in the nucleus (Gao, X., et al., *J. Biol. Chem.* (2008) doi/10.1074/jbc. M804088200). In particular with regard to DACT3, the signaling function has so far not been known in any organism and nothing is known about any relevance to disease such as oncogenesis.

Wnt/β-catenin signaling (for a recent brief overview see e.g. Cadigan, K. M., *Current Biology* (2008) 18, 20, R943-R947) is an ancient and highly conserved signaling pathway involved in various physiological processes such as embryonic development, tissue regeneration including e.g. progenitor-cell formation and proliferation, specification and maintenance of precursor cell and stem cell lineages or stem cell self-renewal. Activation of the Wnt/β-catenin pathway enhances reprogramming of somatic cells into induced pluripotent stem cells (Marson, A., et al. *Cell Stem Cell* (2008) 3, 132-135). The pathway is also involved in a variety of conditions such as cardiovascular disease, bone malformation, aging, obesity, diabetes mellitus, neurodegeneration including schizophrenia or Alzheimer disease, acute renal failure and polycystic kidneys, and inflammation. It can also can also promote appendage regeneration and wound repair. Further, oxidative stress has been found to activate this signal transduction pathway. In this regard, in retinal pigment epithelium the pathway has been reported to be activated upon white light exposure, resulting in a loss of epithelial markers and a gain of mesenchymal markers (Iriyama, A., et al., *Biochem. Biophys. Res. Commun.* (2008) 375, 173-177).

Abnormal Wnt/β-catenin signaling is further known to be associated with cancer. Aberrant Wnt/β-catenin signalling has also been found in ulcerative colitis, where the pathway is activated in early stages of malignant progression (van Dekken, H., et al., *Acta Histochemica* (2007) 109, 4, 266/272). Aberrant activation of Wnt/β-catenin signaling is for example a major driving force in colon cancer (Kinzler, K. W., & Vogelstein, B., *Cell* (1996) 87, 159-170; Su, L. K., et al., *Science* (1992) 256, 668-670; van de Wetering, M., et al., *Cell* (2002) 111, 241-250). More than 90% of all colorectal cancers include an activating mutation of the Wnt/β-catenin pathway, making this cancer an attractive model for molecular intervention.

Mutations in Wnt/β-catenin pathway components including APC, Axin, and β-catenin itself are well-established causes of aberrant signaling activation leading to cancer (Lammi, L., et al., *Am J Hum Genet* (2004) 74, 1043-1050.; Liu, W., et al., *Nat Genet* (2000) 26, 146-147.; Morin, P. J., et al., *Science* (1997) 275, 1787-1790.; Su et al., 1992, supra). As an illustrative example, truncating mutations of both APC alleles, caused by frameshift, nonsense or splice-site mutations, lead to adenomatous polyposis, a type of human colon cancer. As a further example, the formation of cancer stem cells of the mammary gland and epidermis has been shown to be activated via the Wnt/β-catenin pathway. β-catenin signalling has also been shown to be involved in the maintenance of a population of cancer stem cells (Malanchi, I., et al., *Nature* (2008) 452, 7187, 650-653). Deletion of the β-catenin gene in DMBA-TPA or Ras-induced tumours has been shown to result in a complete regression of the tumours.

Genetic defects of components of the Wnt/β-catenin pathway that lead to cancer share in common that they result in the accumulation of β-catenin in the nucleus. In a non-cancerous cell the cytosolic level of β-catenin is kept low in the absence of the Wnt ligand due to phosphorylation by casein kinase 1 and glycogen synthase kinase 3. Phosphorylated β-catenin is ubiquitinylated and subsequent degraded (see FIG. 1A). Mutations can however lead to an accumulation of cytosolic β-catenin, thereby mimicking constitutive Wnt signaling. Mutations in components of the Wnt/β-catenin pathway, including the β-catenin gene, have been found in various cancer forms such as melanoma, esophageal cancer, thyroid cancer, adenocarcinoma of the small intestine, lung cancer, prostate cancer, liver cancer, gastric cancer, ovarian cancer, uterine cancer, hepatocellular cancer, breast cancer, hair matrix cell tumors (pilomatricomas), desmoid tumors, Wilm's tumor (kidney), medulloblastoma (the most frequent brain tumors in childhood), synovial sarcoma and endometrial cancer (for an overview see e.g. Giles, R H, et al., *Biochim Biophys Acta* (2003) 1653, 1-24). Wnt signaling has also been found to play a role in tumor progression and metastasis.

Figure 1B:
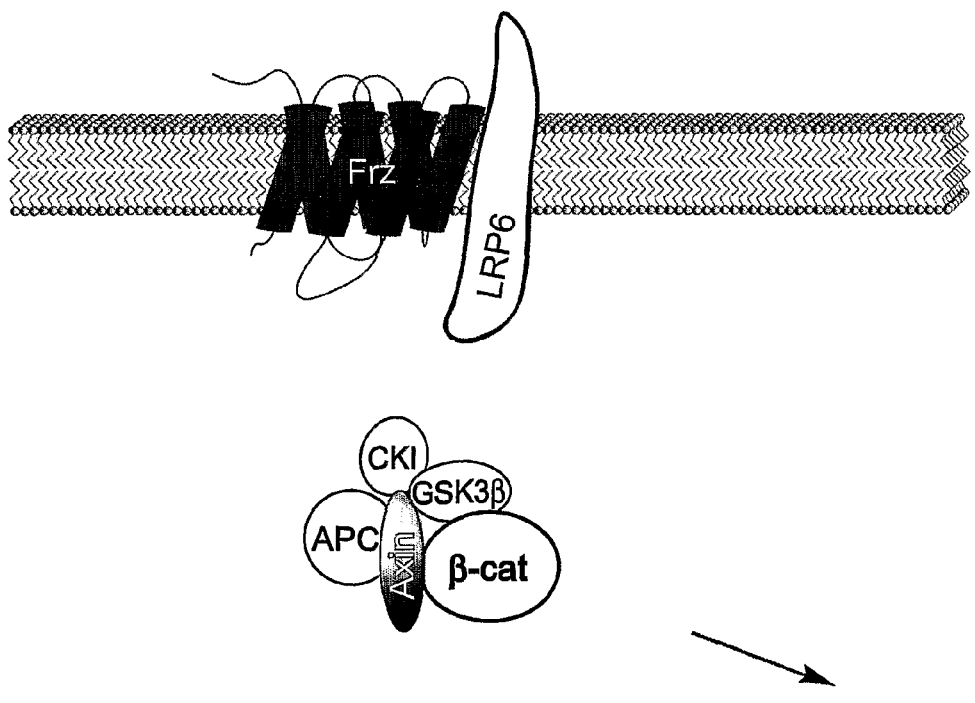
Figure 1B:
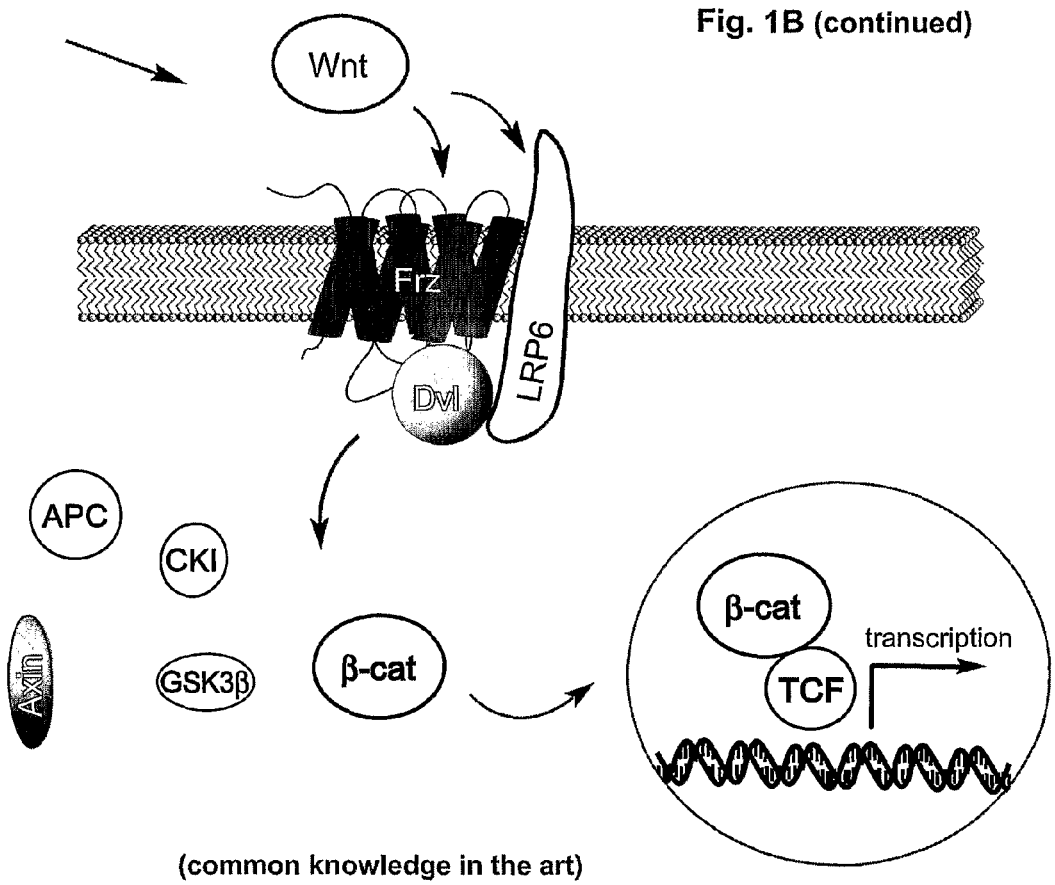
Figure 1C:
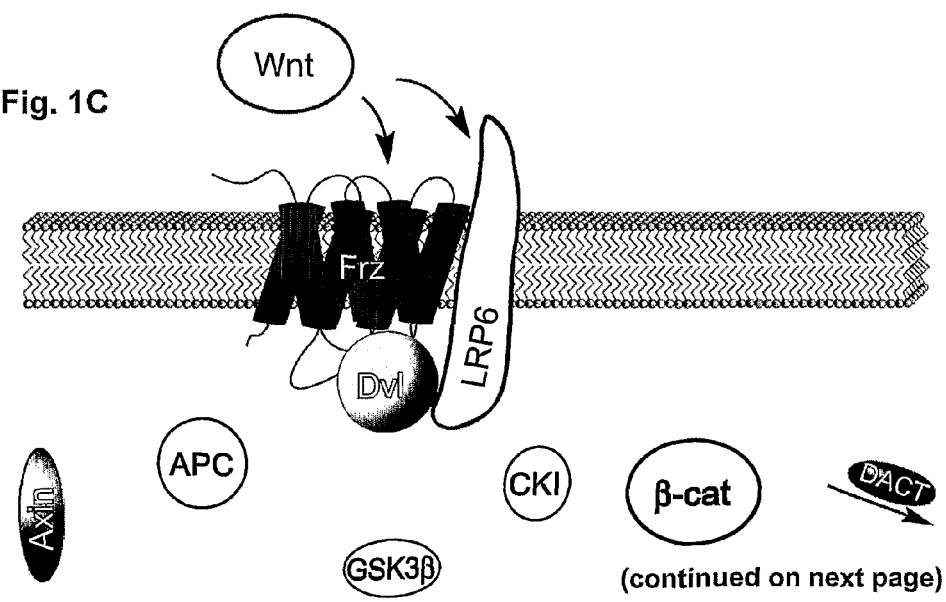
Figure 1C:
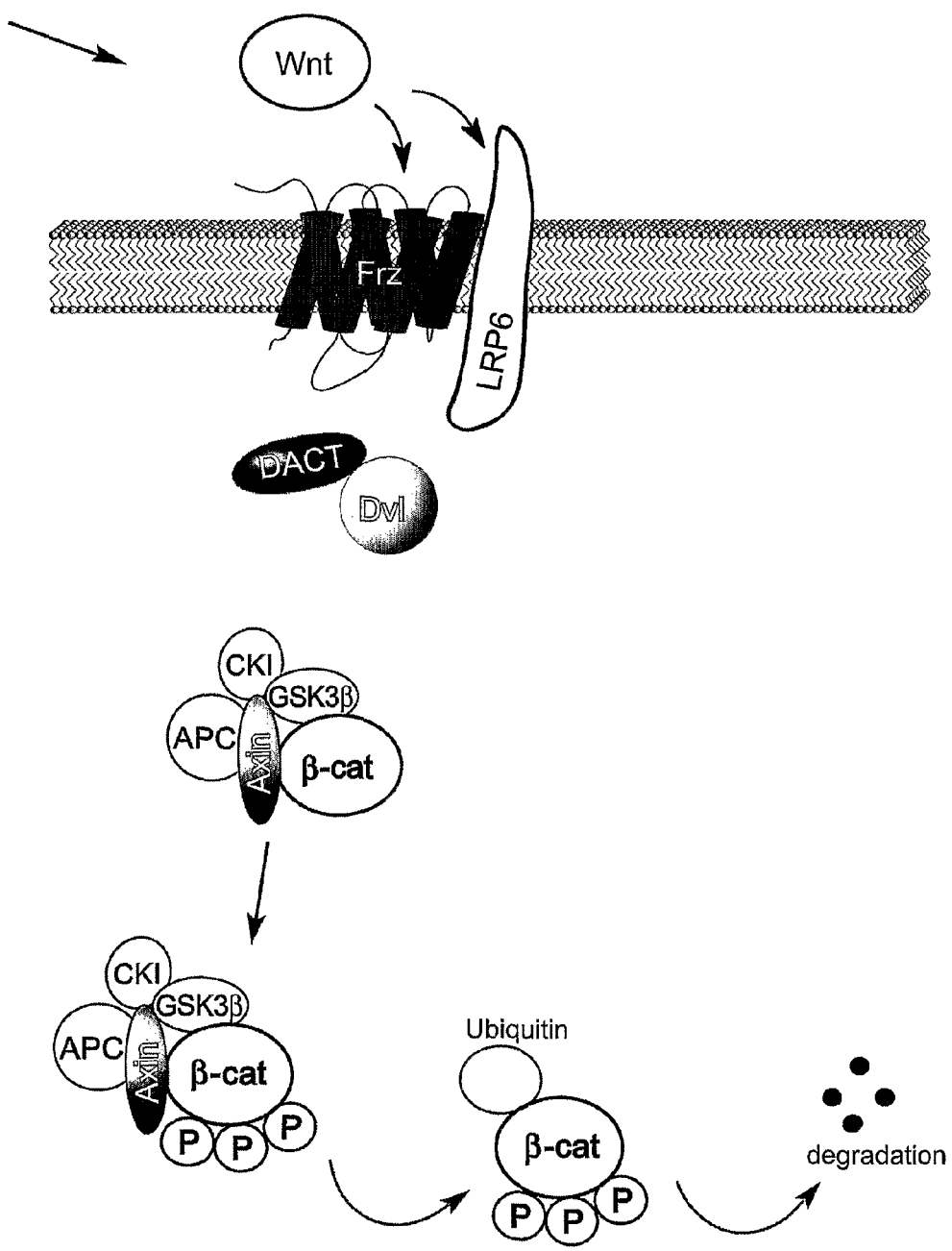

Non phosphorylated and thus stabilized β-catenin is thought to translocate into the nucleus (see FIG. 1B). Nuclear β-catenin interacts with members of the TCF/LEF transcription co-factor family to activate downstream target genes such as Cyclin D1 and Myc that can lead to cell transformation (He, T. C., et al., *Science* (1998) 281, 1509-1512; Morin et al., 1997, supra; Tetsu and McCormick, 1999, supra; van de Wetering et al., 2002, supra). The fact that blockade of Wnt/β-catenin signaling in colon cancer cells induces apoptosis or growth inhibition both in vitro and in vivo (Fujii, N., et al., *Cancer Res* (2007) 67, 573-579; He, B., et al., *Oncogene* (2005) 24, 3054-3058; Kwong, K. Y., et al., *Oncogene* (2002) 21, 8340-8346) has propelled intensive efforts to develop therapeutic strategies that target this pathway (Barker, N., & Clevers, H. *Nat Rev Drug Discov* (2006) 5, 997-1014; Lepourcelet, M., et al., *Cancer Cell* (2004) 5, 91-102; Li, H., et al., *Cancer Biol Ther* (2002) 1, 621-625).

As mentioned above, it has recently been found also by others that DACT1 can interact with β-catenin via its C-terminal domain (Gao et al., 2008, supra). DACT1 further has a nuclear localization signal as well as a nuclear export signal and translocates from the cytoplasm to the nucleus and vice versa (ibid.). It has been suggested that the region of β-catenin that is interacting with DACT1 corresponds to the region interacting with LEF/TCF and the formation of a complex between β-catenin and LEF1 has been shown to be disrupted by DACT1 (ibid.). Via this mechanism DACT1 is likely to antagonize Wnt/β-catenin signalling. DACT1 was further shown to be able to bind to histone deacetylase 1 via its C-terminal domain and to increase the interaction of histone deacetylase 1 with LEF1 (ibid.). This suggests that DACT1 is able to control the expression of targets of Wnt/β-catenin, e.g. c-MYC or cyclin D1, signalling by enhancing the action of co-repressor histone deacetylase 1.

The present inventors have observed that DACT proteins including DACT3 form a complex with a Dishevelled (DVL) protein. The term "complex" refers to an assembly of at least two molecules bound to one another. Dvl proteins are composed of an N-terminal DIX domain, a central PDZ domain and a C-terminal DEP domain. Of these three, the PDZ domain plays the most important role in Wnt signal transduction. Over 20 natural ligands have been reported to bind to the Dvl PDZ domain, most of which have been indicated to be biologically important for canonical or non-canonical Wnt signal pathways. Dvl is also central to Wnt signal transduction (Bilic et al., 2007, supra; Logan, C. Y., & Nusse, R. *Annu Rev Cell Dev Biol* (2004) 20, 781-810). Activation of the Wnt/β-catenin pathway in cancer cells and in other contexts is molecularly observable as an accumulation of unphosphorylated non-membrane associated β-catenin in the nucleus and cytoplasm (Peifer, M., & Polakis, P., *Science* (2000) 287, 1606-1609; Polakis, P., *Curr Opin Genet Dev* (2007) 17, 45-51). Over-expression of Dvl proteins has been observed in several types of cancers, such as non-small cell lung cancer and mesothelioma. Expression of Dvl proteins has been shown to be associated with poor differentiation of lung cancers, and Dvl proteins have been shown to contribute to the metastasis of lung cancer via Wnt/β-catenin signalling (Wei, Q., et al., *Lung Cancer* (2008) doi:10.1016/j.lungcan.2008.06.018).

As noted above it has previously been shown by means of the yeast two-hybrid system and immunoprecipitation that a complex between DACT 1 and Dvl, a key activator of the Wnt/β-catenin pathway, can be formed (Gloy, J., et al., *Nature Cell Biology* (2002) 4, 351-357, Cheyette et al., 2002, supra). Gloy et al. (supra) identified an interaction of the conserved C-terminal domain of DACT and the N-terminal DIX domain and the adjacent sequence (ibid.), which contains a PDZ domain, of Dvl. Based on structural data Cheyette et al (supra) identified interactions of the PDZ domain of Dvl1 and the C-terminal region of DACT in the complex formation. Using chemical-shift perturbation NMR spectroscopy and a yeast two-hybrid screen Wong et al. (2003, supra) identified the C-terminal domain of DACT as being a PDZ-binding motif and the central binding region of Dvl1 as being the PDZ domain of Dvl1. The PDZ domain has in the meantime been found to provide a docking site for a large number of proteins including the C-terminal region of the Frizzled receptor, as well as protein kinases, phosphatases and adaptor proteins, while the DIX domain has been found to allow dimerization of Dvl proteins with other members of the Dvl family as well as with Axin.

All three Dishevelled proteins have the same arrangement of domains including the PDZ domain and the DIX domain. All three proteins are also expressed in cell lines with Dvl2 being predominantly expressed (Lee, Y.-N., et al., *Cellular Signalling* (2008) 20, 443-452). While knock-out and depletion using siRNA suggest individual roles of the three proteins, their roles at least in Wnt/β-catenin signaling seem to depend on the presence of each other and to function cooperatively (ibid.).

Without wishing to be bound by theory it is speculated that one effect of increasing the amount and/or the activity of a DACT protein in a cell involves the formation of a complex between the DACT protein and a subsequent degradation of Dvl proteins. In this regard the inventors' findings are in line with previous observations (Zhang, L., et al., *Science* (2004) 306, 114-117) that one effect of increased DACT protein levels might be degradation of a Dishevelled (DVL) protein. In some embodiments the uses and methods of the invention are accordingly methods of effecting a reduction of a total amount of a Dvl protein, such as Dvl-1, Dvl-2 or Dvl-3, in a cell. The present inventors' findings also shed a new light on a previous report that expression of DACT1 was downregulated in human colorectal cancer (Yau, T.-O., et al., 2005, supra).

On a general basis the present invention also relates to methods and uses of diagnosing, preventing and/or treating a Wnt-mediated disorder, i.e. a physiological disorder, condition, or disease state characterized by aberrant Wnt signalling (see above for examples). In this regard the invention also provides a pharmaceutical composition, as well as a method of predicting the responsiveness of the Wnt-mediated disorder to such a composition. In a specific aspect, the aberrant Wnt signaling is a level of Wnt signaling in a cell or tissue suspected of being diseased that exceeds the level of Wnt signaling in a similar non-diseased cell or tissue. In some embodiments, a Wnt-mediated disorder includes a tumour, including cancer. In such embodiments methods, compounds and compositions according to the present invention can be used for diagnostic and/or therapeutic purposes relating to a tumour, including cancer. In some embodiments these methods, compounds and compositions can be used for diagnostic and/or therapeutic purposes relating to a physiological condition selected from e.g. a neurodegenerative condition, cardiovascular disease, acute renal failure and polycystic kidneys, bone malformation, aging, obesity, diabetes mellitus or inflammation. Further suitable uses include the regulation/control of maintaining the pluripotent state and/or self-renewing characteristics of a stem cell or a progenitor cell, of the formation of a progenitor cell, of the proliferation of a progenitor cell or of the reprogramming of a somatic cell into an induced pluripotent stem cell.

The term "cancer" refers to any cancer caused by the proliferation of malignant neoplastic cells, such as for instance a tumour, a neoplasm, carcinoma, sarcoma, leukemia, lymphoma. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, a bone tumor and a soft-tissue sarcoma, a common solid tumor of an adult such as head and neck cancer—such as oral, laryngeal, nasopharyngeal and esophageal; genito urinary cancer—such as prostate, bladder, renal, uterine, ovarian, testicular; lung cancer—such as small-cell and non small cell; breast cancer; pancreatic cancer; melanoma and other skin cancers; stomach cancer; a brain tumor; a tumour related to Gorlin's syndrome—such as medulloblastoma or meningioma; and liver cancer. Additional exemplary forms of cancer which may be addressed by a method of the invention include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Hence, in some embodiments the present invention relates to a method of preventing carcinogenesis in a cell. The term carcinogenesis (cancerogenesis) as used herein refers to the process by which a normal cell is transformed into cell with a proliferative disorder, in particular into a tumour cell. A respective cell may give rise to a benign tumour and/or a malignant tumor (cancer). A benign tumour does not spread to other parts of the body or invade other tissues. It can nevertheless become a threat to life where it compresses vital structures or is physiologically active (e.g. by producing a hormone). A malignant tumour can invade other organs, spread to distant locations (metastasise) and become life threatening. The respective method includes administering a compound of formula (I) and optionally a histone deacetylase inhibitor, as defined above. In other embodiments a therapy in an individual is being monitored, for example by determining the amount of a DACT protein in a cell of the individual, for instance in a tumor cell. In monitoring treatment or progression of a disease, samples may be obtained from an individual at different timepoints, such as before, during, and/or after a therapy for a disease, such as cancer. In particular embodiments, the amount of a DACT protein, levels of its activity from a sample of an individual and/or the presence of epigenetic alterations (see below) are compared to their respective counterparts obtained at a different timepoint. A difference in the amount or activity of the DACT protein and/or the presence of epigenetic alterations is correlated to success of the therapy and/or progression of the disease, for example.

In some methods and uses according to the invention the amount and/or the activity of a DACT protein, or a functional fragment thereof, is being increased in a cell. The cell may be any cell that is capable of expressing a Dact protein. It may for example be an individual cell or a cell of a cell population. In some embodiments the cell is a somatic cell. Examples of suitable somatic cells, include, but are not limited to a fibroblast, a myeloid cell, a B lymphocyte, a T lymphocyte, a bone cell, a bone marrow cell, a pericyte, a dendritic cell, a keratinocyte, an adipose cell, a mesenchymal cell, an epithelial cell, an epidermal cell, an endothelial cell, a chondrocyte, a cumulus cell, a neural cell, a glial cell, an astrocyte, a cardiac cell, an oesophageal cell, a muscle cell (e.g. a smooth muscle cell or a skeletal muscle cell), a pancreatic beta cell, a melanocyte, a hematopoietic cell, a myocyte, a macrophage, a monocyte, and a mononuclear cell. A somatic cell may be a cell of any tissue, such as for instance skin, kidney, spleen, adrenal, liver, lung, ovary, pancreas, uterus, stomach, colon, small intestine, spleen, bladder, prostate, testicular, thymus, muscle, connective tissue, bone, cartilage, vascular tissue, heart, eye or neural tissue.

In some embodiments the cell is obtained or derived from a host organism, which may be any organism. The cell may be directly taken, e.g. isolated, from a respective host organism in form of a sample such as e.g. a biopsy or a blood sample. It may also have been obtained, e.g. isolated, from a host organism and subsequently been cultured, grown, transformed or exposed to a selected treatment. In some embodiments the cell may be included in a host organism. It may for instance be present in the blood or in tissue, including in an organ, of the host organism. The host organism from which the cell is derived or obtained, including isolated, purified or enriched, or in which it is included, may be any organism such as a microorganism, an animal, such as a fish, an amphibian, a reptile, a bird, a mammal, including a rodent species, an invertebrate species, e.g. of the subclass *Lissamphibia* that includes e.g. frogs, toads, salamanders or newts, or a plant. Examples of mammals include, but are not limited to, a rat, a mouse, a rabbit, a guinea pig, a squirrel, a hamster, a vole, a platypus, a dog, a goat, a pig, a chicken, a macaque, a chimpanzee or a human.

In some embodiments the cell is a tumour cell, e.g. a cancer cell. A respective tumour cell may also be obtained from an organism, e.g. from a mammal. In other embodiments the tumour cell may be included in a mammal, such as for example a rat, a cow, a pig, and a human. A respective tumour cell may also be cultured. It may for instance be a cell of a cell line, such as, but not limited to, colorectal cancer cell lines SW480, HT29, RKO, LST-R1, Caco-2, WiDr, GP2d, HCT116, LoVo, LS174T, VACO5 HCA7, LS411, C70, LIM1863, SL-174T, SW1417, SW403, SW620, SW837 or VACO4A, melanoma cell lines A375, B16 (including B16-F10), BN1, K1735-M2, M14, OCM-1 or WM793, hepatoma cell lines FHCC-98, H4IIE Hep G2, Hep G2f, Huh-7, PLHC-1, SMMC-7721, SK-Hep1 or QGY, lung cancer cell lines A549, ABC-1, EBC-1, LC-1/sq, LCD, LCOK, LK-2, Lu135, MS-1, NCI-H69, NCI H157, NCI-N231, NL9980, PC1, PC3, PC7, PC9, PC10, PC14, QG56, RERF-LCMS, RERF-LCAI, RERF-LCKJ, SBC3 or SQ5, oesophageal cancer cell lines A549, EC109, EC9706 or HKESC-4, gastric cancer cell lines BGC823, KATO-III, MGC803, MKN-45, SGC7901 or ovarian cancer cell lines A2780, C13*, CAOV3, DOV-13, HO8910 (including HO-8910PM), OvCA 3, OvCA 420, OvCA 429, OvCA 432, OvCA 433, OvCar 3, OvCar 5, OvCA 420, OVHM or SKOV-3.

A cell used in a method of the present invention is typically capable of expressing a DACT protein in that it includes a nucleic acid sequence encoding a DACT protein such as DACT2 or DACT3, generally in the form of a functional gene of the DACT protein (whether endogenous or exogenous). In some embodiments the cell expresses the DACT protein. In some embodiments a respective, for instance endogenous, gene encoding a DACT protein is functionally active and expressing the DACT protein. In some embodiments an endogenous nucleic acid sequence encoding a DACT protein is functionally inactive. In some of these embodiments a DACT protein is nevertheless expressed—generally from an exogenous DACT gene. An exogenous gene encoding a DACT protein may be introduced by means of recombinant technology, for instance by means of a vector carrying a DACT protein gene (cf. also below). It may in this regard be advantageous to further use a vector that contains a promoter effective to initiate transcription in the respective host cell (whether of endogenous or exogenous origin).

The term "vector" relates to a single or double-stranded circular nucleic acid molecule that can be transfected into cells and replicated within or independently of a cell genome. A circular double-stranded nucleic acid molecule can be cut and thereby linearized upon treatment with restriction enzymes. An assortment of nucleic acid vectors, restriction enzymes, and the knowledge of the nucleotide sequences cut by restriction enzymes are readily available to those skilled in the art. A nucleic acid molecule encoding a DACT protein can be inserted into a vector by cutting the vector with restriction enzymes and ligating the two pieces together.

The term "promoter" as used herein, refers to a nucleic acid sequence needed for gene sequence expression. Promoter regions vary from organism to organism, but are well known to those skilled in the art for different organisms. For example, in prokaryotes, the promoter region contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like. Both constitutive and inducible promoters can be used in the present invention, in accordance with the needs of a particular embodiment. A large number of promoters recognized by a variety of potential host cells are well known. The selected promoter can be operably linked to cistron DNA encoding a polypeptide described herein by removing the promoter from the source DNA via restriction enzyme digestion and inserting the isolated promoter sequence into the vector of choice. Both the native promoter sequence and many heterologous promoters may be used to direct amplification and/or expression of a selected nucleic acid sequence.

The term "nucleic acid" as used herein refers to any nucleic acid molecule in any possible configuration, such as single stranded, double stranded or a combination thereof Nucleic acids include for instance DNA molecules, RNA molecules, analogues of the DNA or RNA generated using nucleotide analogues or using nucleic acid chemistry, locked nucleic acid molecules (LNA), peptide nucleic acids molecules (PNA) and tecto-RNA molecules (e.g. Liu, B., et al., *J. Am. Chem. Soc.* (2004) 126, 4076-4077). A PNA molecule is a nucleic acid molecule in which the backbone is a pseudopeptide rather than a sugar. Accordingly, PNA generally has a charge neutral backbone, in contrast to for example DNA or RNA. Nevertheless, PNA is capable of hybridising at least complementary and substantially complementary nucleic acid strands, just as e.g. DNA or RNA (to which PNA is considered a structural mimic). An LNA molecule has a modified RNA backbone with a methylene bridge between C4' and O2', which locks the furanose ring in a N-type configuration, providing the respective molecule with a higher duplex stability and nuclease resistance. Unlike a PNA molecule an LNA molecule has a charged backbone. DNA or RNA may be of genomic or synthetic origin and may be single or double stranded. A nucleic acid molecule is generally oligomeric or polymeric. An oligomeric nucleic acid molecule is understood to be a molecule that has roughly about 6 to about 15 monomeric units. Such nucleic acid can be e.g. mRNA, cRNA, synthetic RNA, genomic DNA, cDNA, synthetic DNA, a copolymer of DNA and RNA, an oligonucleotide, etc. A respective nucleic acid may furthermore contain non-natural nucleotide analogues and/or be linked to an affinity tag or a label.

Many nucleotide analogues are known and can be used in the method of the invention. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. Modifications at the base moiety include natural and synthetic modifications of A, C, G, and T/U, different purine or pyrimidine bases, such as uracil-5-yl, hypoxanthin-9-yl, and 2-aminoadenin-9-yl, as well as non-purine or non-pyrimidine nucleotide bases. Other nucleotide analogues serve as universal bases. Universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

The amount of a DACT protein in the cell may be increased by an increased expression, by a reduced degradation or by a combination thereof. An increased expression of a DACT protein may be established by stimulating the expression of an endogenous DACT protein in the cell. Accordingly, transcription and translation of a respective endogenous gene of the cell encoding the respective DACT protein may be stimulated or a state of inhibition thereof may be reduced or terminated.

An increased expression of a DACT protein may also be achieved by expressing an exogenous DACT protein in the cell (supra). As an illustrative example, a nucleic acid molecule that includes a sequence encoding the respective. DACT protein, for example in the form of a vector, may be introduced into the respective cell.

In some embodiments increasing the activity of the DACT protein in the cell includes forming a complex between the DACT protein and a compound, such as an organic low molecular weight compound, an inorganic compound, a peptide or a protein.

As noted above, in some embodiments the cell is not expressing the DACT protein. In such embodiments the method of the invention may include activating an endogenous gene encoding a DACT protein. In some embodiments the method of the invention includes introducing into the cell a nucleic acid molecule, typically a heterologous nucleic acid molecule (supra), encoding a DACT protein capable of allowing expression of the same in the cell. The method in such embodiments further includes expressing the exogenous DACT protein.

The methods and uses according to the present invention may further include assessing the amount or the activity of the DACT protein, or of the corresponding functional fragment of the DACT protein in the cell.

The amount of a DACT protein in a cell may for example be assessed by means of an antibody such as an immunoglobulin, which may be conjugated to a label. In case of the cell being an isolated cell or a microorganism, an intracellular immunoglobulin may be introduced into the cell, for instance following permeabilisation of the cell membrane. The detection may then be carried out in vivo or ex vivo. In some embodiments the detection may be carried out in vitro, for example on a cell extract or cell lysate. Such a technique may include electrophoresis, HPLC, flow cytometry, fluorescence correlation spectroscopy or a modified form or a combination of these techniques.

The term "antibody" generally refers to an immunoglobulin, a fragment thereof or a proteinaceous binding molecule with immunoglobulin-like functions. Examples of (recombinent) immunoglobulin fragments are Fab fragments, Fv fragments, single-chain Fv fragments (scFv), diabodies, triabodies (Iliades, P., et al., *FEBS Lett* (1997) 409, 437-441), decabodies (Stone, E., et al., *Journal of Immunological Methods* (2007) 318, 88-94) and other domain antibodies (Holt, L. J., et al., *Trends Biotechnol*. (2003), 21, 11, 484-490). An example of a proteinaceous binding molecule with immunoglobulin-like functions is a mutein based on a polypeptide of the lipocalin family (WO 2003/029462; WO 2005/019254; WO 2005/019255; WO 2005/019256; Beste et al., *Proc. Natl. Acad. Sci. USA* (1999) 96, 1898-1903). Lipocalins, such as the bilin binding protein, the human neutrophil gelatinase-associated lipocalin, human Apolipoprotein D, human tear lipocalin, or glycodelin, posses natural ligand-binding sites that can be modified so that they bind to selected small protein regions known as haptens. Other non-limiting examples of further proteinaceous binding molecules so-called glubodies (see WO 96/23879), proteins based on the ankyrin scaffold (Mosavi, L. K., et al., Protein Science (2004) 13, 6, 1435-1448) or the crystalline scaffold (WO 2001/04144), the proteins described by Skerra (*J. Mol. Recognit*. (2000) 13, 167-187), AdNectins, tetranectins, avimers and peptoids. Avimers contain so called A-domains that occur as strings of multiple domains in several cell surface receptors (Silverman, J, et al., *Nature Biotechnology* (2005) 23, 1556-1561). Adnectins, derived from a domain of human fibronectin, contain three loops that can be engineered for immunoglobulin-like binding to targets (Gill, D. S. & Damle, N. K., *Current Opinion in Biotechnology* (2006) 17, 653-658). Tetranectins, derived from the respective human homo-trimeric protein, likewise contain loop regions in a C-type lectin domain that can be engineered for desired binding (ibid.). Peptoids, which can act as protein ligands, are oligo(N-alkyl)glycines that differ from peptides in that the side chain is connected to the amide nitrogen rather than the a, carbon atom. Peptoids are typically resistant to proteases and other modifying enzymes and can have a much higher cell permeability than peptides (see e.g. Kwon, Y.-U., and Kodadek, T., *J. Am. Chem. Soc*. (2007) 129, 1508-1509). Where desired, a modifying agent may be used that further increases the affinity of the respective moiety for any or a certain form, class etc. of target matter.

Assessing the activity of a DACT protein may include a measurement of the binding of the protein to a Dvl protein. Such measurements may for instance rely on spectroscopic, photochemical, photometric, fluorometric, radiological, enzymatic or thermodynamic means both in vivo and in vitro. An example for a spectroscopic detection method is fluorescence correlation spectroscopy (see e.g. Haustein, E., & Schwille, P., *Annu. Rev. Biophys. Biomol. Struct*. (2007) 151-169). A photochemical method is for instance photochemical cross-linking. The use of photoactive, fluorescent, radioactive or enzymatic labels, respectively, are illustrative examples for photometric, fluorometric, radiological and enzymatic detection methods. As an illustrative example, as fluorophores also quantum dots may be employed, including in in-vivo measurements (see e.g. Lidke, D. S., et al., *Current Protocols in Cell Biology* (2007) 25.1.1-25.1.18, doi:10.1002/0471143030.cb2501s36). A further illustrative example of the use of fluorescence in vivo is employing a suitable protein, e.g. the enhanced yellow fluorescent protein (EYFP), the green fluorescent protein (GFP), the "superfolder GFP" (sfGFP) or the enhanced cyan fluorescent protein (ECFP), in the bimolecular fluorescence complementation method (for an overview see e.g. Shyu, Y. J., & Hu C.-D., *Trends Biotech*. (2008) 26, 11, 622-630). A general overview on the use of fluorescent probes has been given by Xie et al. (*Annu. Rev. Biophys*. (2008) 37, 417-44). Detection may for instance be based on fluorescence resonance energy transfer or spectroscopically. An example of a thermodynamic detection method is isothermal titration calorimetry. Yet another example of a suitable method of measuring the binding of a DACT protein to a Dvl protein is a surface plasmon resonance technique such as localized surface plasmon resonance (e.g. Endo, T., et al., *Analytica Chimica Acta* (2008) 614, 2, 182-189). Some of these methods may include additional separation techniques such as electrophoresis or HPLC. In detail, examples for the use of a label comprise a compound as a probe or an immunoglobulin with an attached enzyme, the reaction catalysed by which leads to a detectable signal. An example of a method using a radioactive label and a separation by electrophoresis is an electrophoretic mobility shift assay.

Assessing the amount of a DACT protein in a cell may also include assessing the amount of a nucleic acid, e.g. RNA, in a cell encoding the respective DACT protein. A nucleic acid probe may be used to probe a sample by any common hybridization method to detect the amount of nucleic acid molecules of the DACT protein. In order to obtain nucleic acid probes chemical synthesis can be carried out. The synthesized nucleic acid probes may be first used as primers in a polymerase chain reaction (PCR) carried out in accordance with recognized PCR techniques, essentially according to standard PCR Protocols utilizing the appropriate template, in order to obtain the probes of the present invention. One skilled in the art will readily be able to design such probes based on the sequences available for DACT proteins. The hybridization probes can be labeled by standard labeling techniques such as with a radiolabel, enzyme label, fluorescent label, biotin-avidin label, chemiluminescence, a nanoparticle and the like. After hybridization, the probes may be visualized using a standard technique. Albeit the skilled artisan is well aware of this fact, it is noted as a safeguard that in most embodiments an assessment of the amount of a nucleic acid in a cell is not sufficient to assess the amount of a protein in a cell, since the half-life of a respective protein in the cell cannot be assessed based alone on the encoding nucleic acid. Nevertheless, this technique may be used in certain embodiments or in combination with the use of a protein binding agent, for instance for verification purposes.

As noted above, in some embodiments the amount of a DACT protein in the cell is increased by increasing the expression of an endogenous nucleic acid sequence, typically a gene, in the cell that encodes the DACT protein. This increase of expression can be achieved by effecting epigenetic alterations. Accordingly, in some embodiments a method according to the present invention is an epigenetic method. Enhancing the expression of a DACT protein may for instance be carried out by effecting an alteration of the pattern of one or more posttranslational histone modifications. It may for instance be carried out by effecting an alteration of histone methylation. It may also be carried out by effecting an alteration of the pattern of histone acetylation (see also below). In some embodiments both the pattern of histone methylation and histone acetylation are altered. In one embodiment the pattern of histone methylation and/or histone acetylation is altered at the gene locus of a DACT protein, such as a gene locus of DACT3. As an example, a gene of NCBI GeneID 629378, encoding a DACT3 protein, is located in the mouse genome on chromosome 7 at location 7 A2. A corresponding gene with NCBI GeneID 539209, encoding a DACT3 protein, is located in the bovine genome on chromosome 18 at location LOC539209. Corresponding genes are found in the chimpanzee genome at location LOC745677 on chromosome 19 and in the human genome at location 19q13.32 on chromosome 19. A gene of NCBI GeneID 240025, encoding a DACT2 protein, is located in the mouse genome on chromosome 17 at location 17 A2. Corresponding genes are found in the chimpanzee genome (NCBI GeneID 742130) at location between LOC741906 and LOC742320 on chromosome 6, in the rhesus monkey genome on chromosome 4 at location LOC694467, in the human genome (NCBI GeneID 168002) at location 6q27 on chromosome 6, in the rat genome at location 1q12 on chromosome 1, in the zebrafish genome between locations LOC799123 and LOC100000099 on chromosome 6, and in the chicken genome (NCBI GeneID 421561) on chromosome 3 at a location in proximity to LOC395933. In some embodiments one or more, or any, of the above named epigenetic alterations are being detected (see also below). In some embodiments one or more epigenetic alterations are monitored over a selected period of time. Monitoring such alterations may for example serve monitoring a therapy, predicting a response to therapy or determining a diagnosis. The monitoring of the epigenetic alterations, as well as monitoring the level or the activity of a DACT protein, may be further defined as determining resistance to a cancer therapy of the individual, in particular as determining resistance to a combination of a compound of formula (I) and a histone deacetylase inhibitor. When the individual has resistance to such a cancer therapy, an alternative cancer therapy may be administered to the individual.

Epigenetic alterations, which are known to the skilled artisan as reversible alterations (for a general introduction see e.g. Iacobuzio-Donahue, C. A., *Annu. Rev. Pathol. Mech. Dis.* (2009) 4, 229-249), may be detected using conventional methods established in the art. As an example, methylation specific PCR, a bisulphite conversion based technique of the polymerase chain reaction. For this purpose one pair of primers is employed that is specific for unmethylated DNA (U), and one pair of primers that is specific for methylated DNA (M) (cf. also the examples below). At least one primer of each pair has a sequence with one or more CpG sites. As four further examples, bisulphite genomic sequencing, bisulphite pyrosequencing, methylation-sensitive single nucleotide primer extension (MS-SnuPE) and methylation-sensitive single-strand conformation analysis (MS-SSCA) may be used to determine any methylation of cytosine residues of a DNA molecule. In these methods the DNA is treated with bisulphite, causing cytosine residues to be deaminated to uracil, while 5-methylcytosine residues are left largely intact. As two further examples, methylation-specific restriction analysis and methylated DNA immunoprecipitation (MeDIP) may be used to assess DNA methylation.

Epigenetic alterations are generally accompanied by alternative gene expression patterns. Such alterations include for example one or more covalent modification of DNA such as cytosine methylation, one or more covalent modifications of one or more chromosomal proteins, in particular of histones, and the formation of populations of extrachromosomal regulatory small RNA and non-coding RNA molecules. In this regard, the macroscopically visible chromatin is made up of DNA and the histone proteins, around which the DNA is wrapped. Histones are assembled into an octamer made up of two copies of histone 2A, histone 2B, histone 3 and histone 4.

Data available so far not only in vitro, but also in vivo, indicate that epigenetic alterations are more than a reflection of gene expression and rather direct the expression of genes or prime genes in this regard. Certain of these alterations cause transcriptional silencing while others activate transcription. Hence, in each cell there exists a pattern of posttranslational epigenetic modifications. Altering a single of these modifications, e.g. changing the methylation of one base in the genome, thus results in an alteration of the cell's pattern of a posttranslational epigenetic modification and may give rise to altered gene activity states. Accordingly, a single genotype can adopt multiple epigenotypes that confer different phenotypes. Similar to the existence of alleles, there thus also exist epialleles. Epigenetic alterations, for example global DNA hypomethylation or promoter hypermethylation have been found in a variety of cancers (cf. Iacobuzio-Donahue, 2009, supra).

Epigenetic modifications of histones are thus posttranslational modifications. A number of posttranslational modifications of histones are known and more may still be undiscovered. Any such histone modification may be altered, e.g. added, removed, or be prevented from being altered, in the course of a method of the present invention. Acetylation, phosphorylation and ubiquitinylation of histones have so far been observed to increase transcription, while sumoylation has been found to decerase transcription. Histone methylation has in some cases been found to increase, in other cases to decrease transcription. Alterations of these modifications are effected by specific enzymes such as histone acetyltransferases, histone deacetylases, histone methyltransferases or certain transcription factors, such as activating transcription factor 2 (ATF2) or CLOCK, which possess histone acetyltransferase activity. Histone methylation is particularly complex and can exist in mono-, di-(me2) or tri-methylated (me3) states. Each of these states can recruit unique coregulators and exert distinct effects on transcriptional activity. Furthermore, methylation of each lysine residue of a histone has distinct, and often opposite, effects on transcription.

Histone modifications such as monomethylation, dimethylation, trimethylation, acetylation or phosphorylation—in particular of the highly conserved core histones H2A, H2B, H3, and H4—may for instance be detected by chromatin immunoprecipitation (ChIP). The histones are typically crosslinked to the DNA, typically with a crosslinking molecule such as formaldehyde or dimethyl-3,3"-dithiobispropionimidate. Following cell lysis and fragmentation of the DNA, the presence of altered or unaltered histones can then be detected using specific antibodies. A further example of techniques suitable for the detection of histone modifications is mass spectrometric techniques (see e.g. Brumbaugh, J., et al., *Epigenetics* (2008) 3, 5; available at http://www.landesbioscience.com/journals/epigenetics/article/7005). The position of any modification of a histone can for instance be determined by tandem MS methods. As a first step, histone fragments may be generated by proteolytic digestion. Thereafter sequencing via collision activated dissociation (CAD) MS/MS can for example be performed. As a further such method, bisulphite-conversions may be performed as described above. Thereafter a DNA molecule or a fragment of interest thereof may for example be transcribed into RNA in vitro, then be base-specifically cleaved using RNase A, and the cleaved fragments be analyzed by MALDI-TOF.

As explained above, epigenetic events are known to induce alterations in gene expression in the absence of DNA mutation. In this regard methods of the invention also relate to identifying epigenetic patterns that are associated with an altered expression of a DACT protein. The two main epigenetic mechanisms of gene regulation that are exploited by tumour cells and in particular cancer cells to mediate inappropriate gene expression are DNA methylation and histone modification, typically at lysine or arginine side chains. Hypermethylation of CpG-rich areas in the promoter regions of genes induces transcriptional silencing by blocking the access of transcription factors or by enhancing the binding of transcriptional repressors, and is believed to play an important role in cancer by causing a decrease in the expression of tumour suppressor genes. Aberrant histone modifications, such as hypoacetylation, have likewise been associated with malignancy through the transcriptional silencing of tumour suppressor genes. Histones bind to DNA and regulate chromatin structure, and histone deacetylation mediates transcriptional repression by virtue of the fact that the removal of acetyl groups from histones allows them to interact more tightly with DNA, thereby limiting the accessibility of DNA for transcription. Histone acetylation is regulated by the opposing activities of histone acetyl transferase and histone deacetylase (HDAC) enzymes.

It has previously been known that epigenetic events can contribute to abnormal activation of the Wnt/β-catenin signaling pathway, including in cancer cells. Promoter methylation leading to transcriptional silencing of extracellular Wnt inhibitors, such as Secreted Frizzled-Related Proteins (SFRPs), Wnt Inhibitory Factor-1 (WIF-1), and DICKKOPF-1 (DKK-1), have been reported in human colorectal cancer cells (Aguilera, O., et al., *Oncogene* (2006) 25, 4116-4121; He et al., 2005, supra; Morin et al., 1997, supra; Suzuki, H., et al., *Nat Genet* (2002) 31, 141-149). Conversely, restoration of Wnt inhibitor expression such as SFRP1/2 results in inhibition of Wnt/β-catenin signaling and apoptosis of colorectal cancer cells even in the presence of downstream APC or β-catenin mutations (Baylin, S. B., & Ohm, J. E., *Nat Rev Cancer* (2006) 6, 107-116; Suzuki, H., et al., *Nat Genet* (2004) 36, 417-422). In contrast to the methods and uses of the present invention, efforts in the area of epigenetic silencing have however so far focused on direct interference with TCF/β-catenin-mediated transcriptional activation in cancer cells (Barker & Clevers, 2006, supra; Lepourcelet et al., 2004, supra).

Some embodiments of a method according to the present invention include effecting or preventing an alteration of the pattern of a posttranslational histone modification, such as histone methylation and/or histone acetylation. Effecting an alteration of a pattern of a posttranslational histone modification may include effecting the removal of one or more posttranslational histone modification at one or more amino acid positions. Such a modification may for instance be a transcriptionally repressing modification. Effecting an alteration of a pattern of a posttranslational histone modification may include effecting the addition of one or more posttranslational histone modification at one or more amino acid positions. The term "addition" in this regard refers to the formation of a covalent bond to the corresponding amino acid, for instance the covalent attachment of a methyl or acetyl group. Such a modification may for instance be a transcriptionally activating modification. Effecting an alteration of a pattern of a posttranslational histone modification may also include inhibiting or preventing the removal of one or more posttranslational histone modification at one or more amino acid positions. In some embodiments the alteration of a pattern of a posttranslational histone modification includes the alteration of the posttranslational histone modification at two amino acid positions. In some embodiments a combination of an activating posttranslational histone modification and a deactivating (repressing) posttranslational histone modification may be effected. In some embodiments the combination of the removal of one or more transcriptionally repressing posttranslational histone modifications and of the addition of one or more transcriptionally activating posttranslational histone modifications may be effected.

As also exemplified in the examples below, the present inventors have identified histone methylation patterns at the DACT3 promoter that include the concurrent presence of both repressive and activating histone methylation events. In some embodiments methods of prognosis and diagnosis according to the present invention include detecting the presence of such histone methylation patterns. Correspondingly, some embodiments of a method of preventing, arresting or reversing tumourigenesis in a cell include reducing or removing a combination of an activating histone modification, e.g. a methylation and a deactivating histone modification, e.g. a methylation, or preventing the formation of such a combination. Some methods according to the present invention include detecting the presence of such a combination of an activating histone methylation and a deactivating histone methylation. Some methods according to the invention further include the detection of other epigenetic modifications, such as DNA methylation. Such other epigenetic modifications may in some embodiments of methods according to the invention also be altered or prevented from being altered.

In some embodiments of a method according to the invention, which includes effecting an alteration of a pattern of a posttranslational histone modification, the removal of a transcriptionally repressive posttranslational histone modification at one or more histone amino acid positions is effected. In some embodiments of a method according to the invention, which includes effecting an alteration of a pattern of a posttranslational histone modification, the attachment of a transcriptionally activating posttranslational histone modification at one or more histone amino acid positions is effected. In some embodiments of preventing an alteration of a pattern of a posttranslational histone modification inhibition or blockade of the attachment of a transcriptionally repressive posttranslational histone modification at a histone amino acid position is effected. In some embodiments of preventing an alteration of a pattern of a posttranslational histone modification inhibition or blockade of the removal of a transcriptionally activating posttranslational histone modification at a histone amino acid position is effected.

In some embodiments of such a method a combination of the removal of a transcriptionally repressive posttranslational histone modification and the attachment of a transcriptionally activating posttranslational histone modification is effected. Examples of a suitable activating posttranslational histone modification include, but are not limited to, the methylation of lysine 4 on histone 3, the acetylation of lysine 9 on histone 3, and the acetylation of lysine 14 on histone 3. Examples of a suitable repressive posttranslational histone modification include, but are not limited to, the methylation of lysine 9 on histone 3, the methylation of lysine 27 on histone 3, and the methylation of lysine 20 on histone 4.

An alteration of the pattern of histone methylation and/or histone acetylation is in some embodiments of certain methods and uses according to the present invention effected by applying, e.g. administering a compound or a combination of compounds. Such a compound may be identified using a method of identifying a compound that is effective in this regard, as explained below. A further example of a suitable compound is a compound of general formula (I) (supra, see also below). An illustrative example of a combination of compounds is a combination of compound of general formula (I) and a histone deacetylase inhibitor.

Instead of or in addition to altering the pattern of methylation and/or acetylation of endogenous histones of a respective cell, heterologous histones may be used. Such heterologous histones may for example be formed in the cell by expressing a heterologous nucleic acid molecule encoding a histone by means of conventional recombinant technology. Such a histone may have mutations/alterations when compared to the endogenous histones of the cell that mimic histones with certain methylation/acetylation patterns or that cannot be methylated and/or acetylated at positions of interest. Where an in vitro method is carried out, one or more isolated histones may also be subjected to a chemical modification. Histones may also be formed in vitro using one or more amino acid derivatives, e.g. one or more methylated lysine analogs.

Some methods and uses according to the invention include or aim at inducing apoptosis in one or more cells involved in a cell proliferative disorder such as hyperplasia, dysplasia and a pre-cancerous lesion. In some embodiments these methods include or aim at inducing apoptosis in a tumour cell. Apoptosis is a programmed cell death and typically a mechanism in a multicellular organism to remove undesired cells. Where a cell's capability to undergo or initiate apoptosis is impaired or abolished, a damaged cell is able to proliferate in an unchecked manner, thereby developing into a cancer cell. An apoptotic cell shows a characteristic morphology, by which it can be identified under a microscope. By inducing apoptosis in a tumour cell, a corresponding method may also be used as a therapy for the treatment or prevention of cancer.

In some embodiments apoptosis in a tumor cell, including a cancer cell, is induced by altering, e.g. increasing, the phosphorylation status of the protein β-catenin. The phosphorylation status of the protein β-catenin is in such embodiments typically altered, e.g. increased, by altering the amount and/or the activity of a DACT protein in the tumor cell. As an illustrative example, the amount of a DACT protein may be increased in the tumor cell, thereby reducing the amount of a dishevelled protein in the tumor cell. The amount of the dishevelled protein in the tumor cell may be reduced by means of degradation, for instance once a complex between the dishevelled protein and the DACT protein has formed. As a result the protein glycogen synthase kinase 3 may be activated, thereby increasing, the phosphorylation status of the protein β-catenin.

Where desired, the progress of apoptosis in a tumour cell may be monitored, for example by propodium iodide staining, Annexin V-FITC staining, flow cytometry analysis, or combinations thereof, as well as mitochondrial dysfunction or caspase 3 activation. Typically the method of the invention triggers an apoptotic cell death response involving mitochondria disruption and caspase activation. Non-cancerous cells however show only a marginal cell death response, if any at all. Besides determining apoptosis in a respective cell in some embodiments a method according to the present invention may include determining cell viability in a respective cell. Respective methods are well established in the art.

As noted above, in some embodiments of a method of the invention the amount of a dishevelled protein and/or of a DACT protein is reduced in a respective cell. This may be carried out by introducing a heterologous molecule into the cell, such as a nucleic acid molecule. As an example, a non-coding nucleic acid molecule may be used, such as for example an aptamer or a Spiegelmer® (described in WO 01/92655). A non-coding nucleic acid molecule may also be an nc-RNA molecule (see e.g. Costa, F F, Gene (2005), 357, 83-94 for an introduction on natural nc-RNA molecules). Examples of nc-RNA molecules include, but are not limited to, an anti-sense-RNA molecule, an L-RNA Spiegelmer®, a silencer-RNA molecule (such as the double-stranded Neuron Restrictive Silencer Element), a micro RNA (miRNA) molecule, a short hairpin RNA (shRNA) molecule, a small interfering RNA (siRNA) molecule, a repeat-associated small interfering RNA (rasiRNA) molecule or an RNA that interacts with Piwi proteins (piRNA) (for a brief review see e.g. Lin, H., Science (2007) 316, 397). Such non-coding nucleic acid molecules can for instance be employed to direct mRNA degradation or disrupt mRNA translation.

The use of small interfering RNAs has become a tool to "knock down" specific genes. An overview on the differences between the use of synthetic small organic compounds and RNAi has been given by Weiss et al. (Nature Chem. Biol. (2007) 3, 12, 739-744). Small interfering RNA makes use of gene silencing or gene suppression through RNA interference (RNAi), which occurs at the posttranscriptional level and involves mRNA degradation. RNA interference represents a cellular mechanism that protects the genome. SiRNA molecules mediate the degradation of their complementary RNA by association of the siRNA with a multiple enzyme complex to form what is called the RNA-induced silencing Complex (RISC). The siRNA becomes part of RISC and is targeted to the complementary RNA species which is then cleaved. This leads to the loss of expression of the respective gene (for a brief overview see Zamore, P D, & Haley, B, Science (2005) 309, 1519-1524). This technique has for example been applied to silencing parasitic DNA sequences, such as the cleavage of HIV RNA, as disclosed in US patent application 2005/0191618.

While a siRNA molecule is formed from exogenous double stranded RNA, a miRNA molecule is a RNA molecule transcribed from the genome, although it is structurally similar to siRNA molecules. Principally a miRNA molecule can operate in the same way as a siRNA molecule (for an overview see e.g. Liu, J., Current Opinion in Cell Biology (2008) 20, 214-221). While initially only miRNA was known that acted on the 3'-untranslated regions of transcripts, meanwhile miRNA has been described that can simultaneously target several sites in the coding sequence of a single mRNA molecule or the CDSs of different mRNA molecules (Tay, Y., et al., *Nature* (2008) doi:10.1038/nature07299). It was also suggested that short interfering RNA molecules can modulate gene expression through sites within the coding sequence with only partial complementarity to the siRNA (ibid.). These findings open the possibility of directing degradation or disrupting translation of selected isoforms, splice variants or mutants of a protein.

A typical embodiment of a siRNA or miRNA for the current invention includes an in vitro or in vivo synthesized molecule of about 10 to 35 nucleotides, in some embodiments about 15 to 25 nucleotides. A respective siRNA or miRNA molecule may be directly synthesized within a cell of interest, including a cell that is part of a microorganism and an animal. It may also be introduced into a respective cell and/or delivered thereto. An illustrative example of delivering a siRNA molecule into selected cells in vivo is its non-covalent binding to a fusion protein of a heavy-chain antibody fragment (Fab) and the nucleic acid binding protein protamin (Song, E. et al., *Nature Biotech.* (2005) 23, 6, 709-717). In an embodiment of the present invention siRNA and/or miRNA molecules are used to induce a degradation of mRNA molecules encoding one or more DACT proteins or dishevelled proteins of interest.

As noted above, activation of the Wnt/β-catenin pathway plays a role in the formation of cancer stem cells (Malanchi et al., 2008, supra). There is also evidence that Wnt/β-catenin signaling plays a central role in the maintenance of epithelial stem cells and of early progenitors (de Lau, W., et al., *Front Biosci* (2007) 12, 471-491; Fodde, R., & Brabletz, T., *Curr Opin Cell Biol* (2007) 19, 150-158). The GSK-3 inhibitor 6-bromoindirubin-3'-oxime, which activates the Wnt/β-catenin pathway, has been shown to maintain the undifferentiated state of pluripotent human and mouse embryonic stem cells (Sato, N., et al., *Nature Medicine* (2004) 10, 1, 55-63). Proliferation of satellite cells, the stem cell population of adult skeletal muscle, has been shown to effected via activation of the Wnt/β-catenin pathway (Otto, A., et al., *Journal of Cell Science* (2008) 121, 2939-2950). Inhibition of Wnt/β-Catenin signaling has been shown to reduce pluripotency and proliferation capacity of rabbit embryonic stem cells and to result in their enhanced differentiation (Wang, S., et al., *J. Biol. Chem.* (2008) doi/10.1074/jbc.M804091200). It has also been shown that maintenance and self-renewal of multipotent intestinal stem cells of *Drosophila* is dependent on the pathway corresponding to Wnt/β-catenin signalling, which is the Wingless (Wg) pathway (Lin, G., et al., *Nature* (2008) 455, 1119-1124). Likewise, the reprogramming of somatic cells to induced stem cells has been shown to be enhanced by an activation of the Wnt/β-catenin pathway (Marson et al., 2008, supra). In this regard there is also data suggesting that the initial epigenetic event(s) that upregulate(s) Wnt/β-catenin signaling may occur in colorectal adenomas before they acquire fully-transforming APC mutations (Siu, I. M., et al., *Cancer Res* (1999) 59, 63-66; Suzuki et al., 2004, supra). Bivalent histone modification at DACT3 could be one such epigenetic event. The combined pharmacologic approach of the invention, which targets in some embodiments an epigenetic signature characteristic of inter alia colorectal cancer cells and which is capable of abrogating Wnt/β-catenin signaling, may have the potential to target cancer stem cells that rely on this mechanism of gene silencing and that require high levels of Wnt/β-catenin signaling activity for their self-renewal and survival.

Accordingly, a method according to the present invention may also be used to control, including prevent and terminate, the maintenance and/or the proliferation of a stem cell. Such a stem cell may in some embodiments be a cancer stem cell, for instance a colon cancer stem cell. Colon cancer stem cells, also called colon cancer tumor-initiating cells, are typically found in primary colon cancer (e.g. Huang, E. H., & Wicha, M. S., *Trends Mol. Med.* (2008) 14, 11, 503-509). A method of the invention may also be used to control, including prevent or terminate, the reprogramming of an at least partially differentiated cell such as a somatic cell into a pluripotent cell, in particular into a stem cell. In typical embodiments of the latter case the method is a method of controlling, including preventing and terminating, dedifferentiation of an at least partially differentiated cell. In some embodiments such a method is a method of preventing the formation of a cancer cell.

In some embodiments a method according to the present invention may be a method of or a use in the treatment and/or prevention of a cardiovascular disease or disorder such as myocardial infarct. As disclosed in international patent application WO 2008/122440, the depletion of β-catenin has a protective effect on the heart. In this disclosure downregulation of β-catenin was shown to initiate adaptive cardiomyocyte hypertrophy in the adult heart and to restore signaling pathways required for protective hypertrophy after angiotensin II-induced stress. The methods of the present invention lead to a reduction of levels of activated β-catenin (cf. e.g. FIG. 6A) and of the expression of TCF/β-catenin target genes (cf. e.g. FIG. 6C and FIG. 6D). Such an effect has been shown to result in adaptive cardiac hypertrophy, which has a heart-protective function (WO/2008/122440). Those skilled in the art will appreciate that, contrary to previous methods (ibid.), some embodiments of the methods of the present invention can achieve this effect without the requirement of inserting foreign DNA into target cells.

In some embodiments a method or a use according to the invention includes the use of a compound of the following general formula (I)

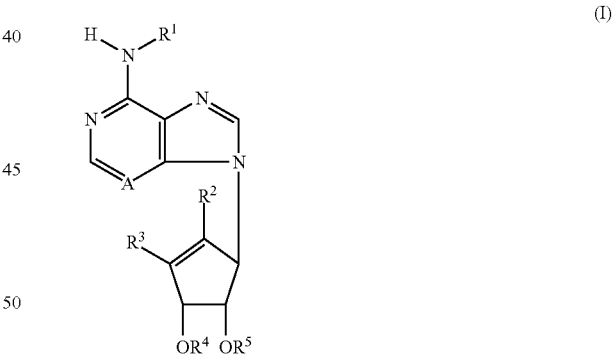

In this general formula (I), A represents CH or N. $R^1$, $R^4$ and $R^5$ may be H or independently selected aliphatic, alicyclic, aromatic, arylaliphatic, and arylalicyclic groups, which may optionally include 0-6, in some embodiments 0-4, and in some embodiments 0-3 heteroatoms. The heteroatoms may be N, O, P, S, Se or Si. In some embodiments $R^4$ and $R^5$ may be identical. In some embodiments $R^4$ and $R^5$ may be linked so as to define an aliphatic bridge, e.g. a hydrocarbyl bridge. A respective bridge may for example include 1-12, in some embodiments 2-10, and in some embodiments 2-8 main chain carbon atoms and contain 1-5, in some embodiments 1-4, and in some embodiments 1-3 heteroatoms selected from the group N, O, P, S, Se, and Si. $R^2$ may be H or a halogen atom, such as F, Cl, Br or I. In some embodiments $R^2$ is F or Cl. $R^3$ may be H, a halogen atom such as F or Cl, or an aliphatic, alicyclic, aromatic, arylaliphatic or arylalicyclic hydrocarbyl group. This hydrocarbyl group may include 1-12, in some embodiments 1-8, and in some embodiments 1-4, main chain carbon atoms and 0-4, such as 0-3 or 0-2 heteroatoms selected from the group N, O, P, S, Se or Si. The hydrocarbyl group may further be bonded to any substituent or substituents (see below), including one or more functional groups, such as halogen. e.g. F or Cl.

A heteroatom is any atom that differs from carbon. Examples include, but are not limited to N, O, P, S, Si and Se. Where several heteroatoms are present within a moiety of a reactant or product of the process of the invention, they are independently selected.

The term "aliphatic" means, unless otherwise stated, a straight or branched hydrocarbon chain, which may be saturated or mono- or polyunsaturated. An unsaturated aliphatic group contains one or more double and/or triple bonds. The branches of the hydrocarbon chain may include linear chains as well as non-aromatic cyclic elements. The hydrocarbon chain, which may, unless otherwise stated, be of any length, and contain any number of branches. Both the main chain as well as the branches may furthermore contain heteroatoms as for instance N, O, S, Se or Si.

The term "alicyclic" means, unless otherwise stated, a nonaromatic cyclic hydrocarbon moiety, which may be saturated or mono- or polyunsaturated. The cyclic hydrocarbon moiety may be substituted with nonaromatic cyclic as well as chain elements. The main chain of the cyclic hydrocarbon moiety may, unless otherwise stated, be of any length and contain any number of non-aromatic cyclic and chain elements. Both the cyclic hydrocarbon moiety and the cyclic and chain substituents may furthermore contain heteroatoms, as for instance N, O, S, Se or Si.

The term "aromatic" means, unless otherwise stated, a planar cyclic hydrocarbon moiety of conjugated double bonds, which may be a single ring or include multiple fused or covalently linked rings. The main chain of the cyclic hydrocarbon moiety may, unless otherwise stated, be of any length and contain any number of heteroatoms, as for instance N, O and S.

By the term "arylaliphatic" is meant a hydrocarbon moiety, in which one or more aryl groups are attached to or are substituents on one or more aliphatic groups. Thus the term "arylaliphatic" includes for instance hydrocarbon moieties, in which two or more aryl groups are connected via one or more aliphatic chain or chains of any length, for instance a methylene group.

Each of the terms "aliphatic", "alicyclic", "aromatic" and "arylaliphatic" as used herein is meant to include both substituted and unsubstituted forms of the respective moiety. Substituents my be any functional group, as for example, but not limited to, amino, amido, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzenesulfonyl, nitrobenzenesulfonyl, and methanesulfonyl.

Typical compounds of formula (I) can be addressed as analogues (including carbocyclic analogues) of adenosine. Illustrative examples of a suitable compound are 3-deazaneplanocin A (5-(4-amino-1H-imidazo[4,5-c]pyridin-1-yl)-3-(hydroxymethyl)-3-cyclopentene-1,2-diol, Chemical Abstracts No. 102052-95-9), 5-(4-amino-1H-imidazo[4,5-c]pyridin-1-yl)-3-(1-hydroxyethyl)-3-cyclopentene-1,2-diol, Chemical Abstracts No. 146424-81-9, 5-(4-amino-1H-imidazo[4,5-c]pyridin-1-yl)-3-(1,1-dihydroxypropyl)-3-cyclopentene-1,2-diol, CAS-No. 851071-63-1, 5-(4-amino-1H-imidazo[4,5-c]pyridin-1-yl)-3-[1-hydroxy-2-propenyl]-3-cyclopentene-1,2-diol, CAS-No. 851071-61-9, 5-(4-amino-1H-imidazo[4,5-c]pyridin-1-yl)-4-fluoro-3-(hydroxymethyl)-3-cyclopentene-1,2-diol, CAS-No. 127828-67-5, 5-(4-amino-1H-imidazo[4,5-c]pyridin-1-yl)-3-(2-propenyl)-3-cyclopentene-1,2-diol, CAS-No. 851071-58-4, 5-(4-amino-1H-imidazo[4,5-c]pyridin-1-yl)-3-methyl-3-cyclopentene-1,2-diol, CAS-No. 224 453-13-8, 5-(4-amino-1H-imidazo[4,5-c]pyridin-1-yl)-3-cyclopentene-1,2-diol, CAS-No. 111 005-71-1, 5-(4-amino-1H-imidazo[4,5-c]pyridin-1-yl)-4-chloro-3-cyclopentene-1,2-diol, CAS-No. 127828-64-2, 5-(6-amino-9H-purin-9-yl)-3-(hydroxymethyl)-3-cyclopentene-1,2-diol, CAS-No. 88824-06-0, 4-(6-amino-9H-purin-9-yl)-3a,6a-dihydro-2,2-dimethyl-4H-cyclopenta-1,3-dioxole-6-methanol, CAS-No. 88824-08-2, N-[9-[5-(acetyloxy)-4-hydroxy-3-(hydroxymethyl)-2-cyclopenten-1-yl]-9H-purin-6-yl]-benzamide, CAS-No. 83844-33-1, 5-(6-amino-9H-purin-9-yl)-3-(methoxymethyl)-3-cyclopentene-1,2-diol, CAS-No. 138571-48-9, 4-methyl-benzoic acid [3-(6-amino-9H-purin-9-yl)-4-hydroxy-5-[(4-methylbenzoyl)oxy]-1-cyclopenten-1-yl]methyl ester, CAS-No. 142888-07-1, 5-(6-amino-2-fluoro-9H-purin-9-yl)-3-(hydroxymethyl)-3-cyclopentene-1,2-diol, CAS-No. (hydrochloride) 138660-07-8, 5-(6-amino-8-chloro-9H-purin-9-yl)-4-chloro-3-cyclopentene-1,2-diol, CAS-No. 127828-72-2, 3-(6-amino-9H-purin-9-yl)-4,5-dihydroxy-1-cyclopentene-1-carboxylic acid, CAS-No. 179929-29-4, 5-(6-amino-9H-purin-9-yl)-3-propyl-3-cyclopentene-1,2-diol, CAS-No. 851071-49-3, 5-(6-amino-9H-purin-9-yl)-3-(fluoromethyl)-3-cyclopentene-1,2-diol, CAS-No. 303964-14-9, 5-(6-amino-9H-purin-9-yl)-4-fluoro-3-(fluoromethyl)-3-cyclopentene-1,2-diol, CAS-No. 805245-51-6, 5-(6-amino-9H-purin-9-yl)-4-fluoro-3-(mercaptomethyl)-3-cyclopentene-1,2-diol, CAS-No. 805245-54-9, 5-(6-amino-9H-purin-9-yl)-3-(1-hydroxy-2-propynyl)-3-cyclopentene-1,2-diol, CAS-No. 141794-36-7, 9-[(3aS,4R,6aR)-6-[[[(1,1-dimethylethyl)diphenylsilyl]oxy]methyl]-3a,6a-dihydro-2,2-dimethyl-4H-cyclopenta-1,3-dioxol-4-yl]-9H-purin-6-amine, CAS-No. 952418-12-1, 9-[(3aS,4R,6aR)-3a,6a-dihydro-2,2-dimethyl-6a-[2-(triphenylmethoxy)ethyl]-4H-cyclopenta-1,3-dioxol-4-yl]-9H-purin-6-amine, CAS-No. 902455-29-2, 9-[(3'aS,6'aR)-3'a,6'a-dihydrospiro[cyclohexane-1,2'-[4H]cyclopenta[1,3]dioxol]-4'-yl]-9H-purin-6-amine, CAS-No. 874443-97-7, 9-[(3aS,4R,6aR)-3a,6a-dihydro-2,2-dimethyl-6-(trifluoromethyl)-4H-cyclopenta-1,3-dioxol-4-yl]-9H-purin-6-amine, CAS-No. 872624-41-4, (1S,2R,5R)-5-(6-amino-9H-purin-9-yl)-3-(trifluoromethyl)-3-cyclopentene-1,2-diol, CAS-No. 872624-35-6, (1S,2R,5R)-5-(6-amino-9H-purin-9-yl)-3-(1,1-dihydroxy-2-propenyl)-3-cyclopentene-1,2-diol, CAS-No. 851071-54-0, (1S,2R,5R)-5-(6-amino-9H-purin-9-yl)-3-(2-propenyl)-3-cyclopentene-1,2-diol, CAS-No 851071-50-6, 1-[(3'aS,6'aR)-3'a,6'a-dihydrospiro[cyclohexane-1,2'-[4H]cyclopenta[1,3]dioxol]-4'-yl]-1H-imidazo[4,5-c]pyridin-4-amine, CAS-No. 874443-98-8, (1R,2S,5S)-5-(4-amino-1H-imidazo-[4,5-c]pyridin-1-yl)-3-(hydroxymethyl)-3-cyclopentene-1,2-diol, CAS-No. 948306-87-4, (1S,2R,5S)-5-(6-amino-9H-purin-9-yl)-4-fluoro-3-(fluoromethyl)-3-cyclopentene-1,2-diol, CAS-No. 805245-51-6, the compound of CAS-No. 1062238-89-4, the compound of CAS-No. 1062238-85-0, the compound of CAS-No. 1062238-82-7, the compound of CAS-No. 1062238-79-2, the compound of CAS-No. 1062238-77-0, and the compound of CAS-No. 1062238-66-7.

Figure 5C:
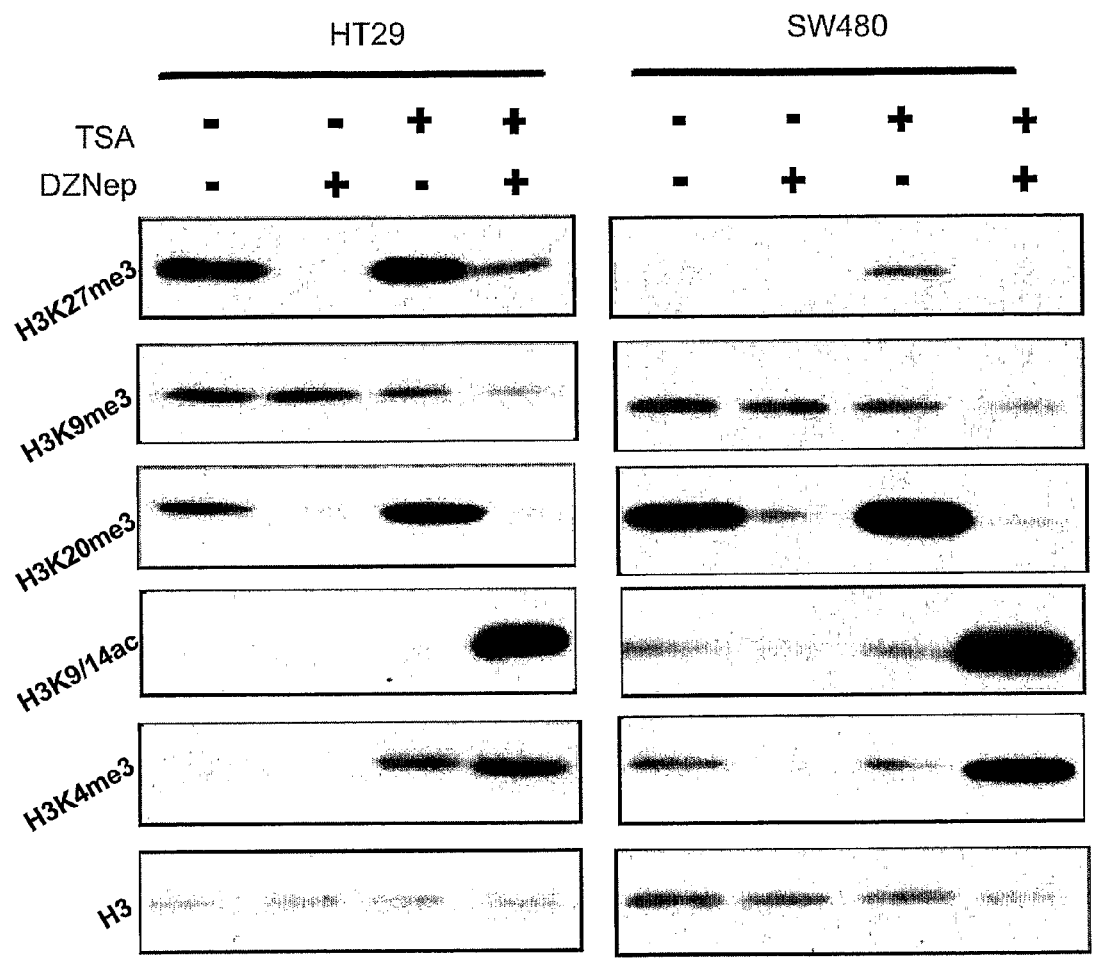
FIG. 5 illustrates the effects of a DZNep/TSA combination on DACT3 expression (A, B) and histone modifications (C, D) in cancer cells.

Compounds of general formula (I) are for example typically able to effect or prevent an alteration of the pattern of a posttranslational histone modification, in particular of one or more histone methylations or histone acetylations. Such compounds are typically able to effect a demethylation of lysine 27 on histone 3 or a demethylation of lysine 20 on histone 4 and/or to prevent a methylation of these lysine residues—in particular at the gene locus of a DACT protein—as illustrated in FIG. 5C.

In some embodiments the compound of general formula (I) is used in combination with a histone deacetylase inhibitor. Any histone deacetylase inhibitor may be used in the context of the present invention. Histone deacetylase inhibitors from various chemical classes have been described, with four most important classes, namely (i) hydroxamic acid analogs, (ii) benzamide analogs, (iii) cyclic peptides (generally tetrapeptides)/peptolides and (iv) fatty acid analogs. Histone deacetylase inhibitors differ in their specificities towards the various histone deacetylases. These enzymes are being divided into four main classes according to their sequence homology and expression patterns. Histone deacetylase inhibitors differ in their specificities towards the four main classes of histone deacetylases. These enzymes are being divided into four classes according to their sequence homology and expression patterns. Generally hydroxamic acid analogs are effective on classes I, II, IV enzymes, benzamide analogs on class I and some also on classes II, III and/or IV, cyclic peptides/peptolides on class I and fatty acid analogs on classes I and II. Brief overviews on histone deacetylase inhibitors have recently been given by Smith and Workman (*International Journal of Biochemistry & Cell Biology* (2008) doi:10.1016/j.biocel.2008.09.008) and, in a broader context, by Szyf (*Annu. Rev. Pharmacol. Toxicol.* (2009) 49, 243-263).

Suitable examples of a histone deacetylase inhibitor include, but are not limited to, N'-hydroxy-N-phenyl-octanediamide (suberoylanilide hydroxamic acid, SAHA), pyroxamide, M-carboxycinnamic acid bishydroxamide (CBHA), trichostatin A (TSA), trichostatin C, salicylihydroxamic acid (SBHA), azelaic bishydroxamic acid (ABHA), azelaic-1-hydroxamate-9-anilide (AAHA), 6-(3-chlorophenylureido) carpoic hydroxamic acid (3C1-UCHA), oxamflatin, A-161906, scriptaid, PXD-101, LAQ-824, cyclic hydroxamic acid-containing peptide (CHAP), ITF-2357, MW2796, MW2996, trapoxin A, FR901228 (FK 228 or Depsipeptide), FR225497, apicidin, CHAP, HC-toxin, WF27082, chlamydocin, sodium butyrate, isovalerate, valerate, 4-phenylbutyrate (4-PBA), 4-phenylbutyrate sodium (PBS), arginine butyrate, propionate, butyramide, isobutyramide, phenylacetate, 3-bromopropionate, tributyrin, valproic acid, valproate, CI-994, MS-27-275 (MS-275 or SNDX-275), 3'-amino derivative of MS-27-275, MGCD0103 or Depudecin, and SNDX-275. A number of histone deacetylase inhibitors are currently being clinically tested and SAHA (Vorinostat®) has recently been approved by the FDA for treatment of cutaneous T cell lymphoma.

In some embodiments the histone deacetylase inhibitor is a compound of the general formula (II) or of the general formula (III):

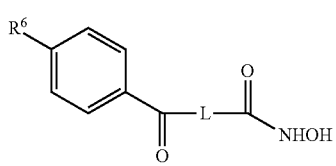

(II)

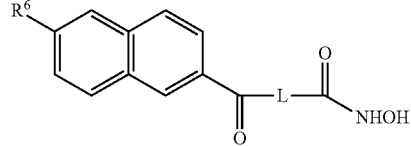

(III)

In these general formulas (II) and (III), L is a bridge that includes an aliphatic or arylaliphatic group, which includes 1 to about 8 main chain carbon atoms and 0 to about 3 heteroatoms such as N, O or Si. $R^6$ is H, an amino group, an ether group, an aliphatic group or an arylaliphatic group. Where $R^6$ is an amino group, this amino group may be substituted independently with two moieties. These may for instance be H, an aliphatic group, an alicyclic group, an aromatic group, an arylaliphatic group, or an arylalicyclic group. Such a group may independently include 0 to about 3 heteroatoms such as N, O, S or Si. Where $R^6$ is an ether group, the oxygen atom of the ether group may be substituted with an aliphatic, alicyclic, aromatic, arylaliphatic, or an arylalicyclic group, that may include 0 to about 3 heteroatoms such as N, O, S or Si.

Examples of a compound of general formula (II) include, but are not limited to, 7-[R-(E,E)]-[4-(dimethylamino)phenyl]-N-hydroxy-4,6-dimethyl-7-oxo-2,4-heptadienamide (Trichostatin A, Chemical abstracts No. 58880-19-6), 7-[4-(dimethylamino)phenyl]-N-hydroxy-4,6,6-trimethyl-7-oxo-2,4-heptadienamide (CAS No. 1051944-84-3), 4-(dimethylamino)-N-hydroxy-δ-oxo-benzenepentanamide (CAS No. 139675-90-4), N-hydroxy-6-(benzoyl)hexanamide (CAS No. 91489-63-3), 3-p-toluoyl-acrylohydroxamic acid (CAS No. 96985-88-5), (2E,4E,6R)-7-[4-(cyclohexylamino)phenyl]-N-hydroxy-4,6-dimethyl-7-oxo-2,4-heptadienamide (CAS No. 1051944-79-6), N-hydroxy-6,6-dimethyl-7-(4-methoxybenzoyl)heptanamide (CAS No. 362669-76-9), (2E,4E,6R)-6-[4-(dimethylamino)benzoyl]-N-hydroxy-4-methyl-2,4-octadienamide (CAS No. 1051944-83-2), (2E,4E,6R)—N-hydroxy-4,6-dimethyl-7-oxo-7-[4-(1-piperidinyl)phenyl]-2,4-heptadienamide (CAS No. 1051944-81-0), (2E,4E,6R)—N-hydroxy-4,6-dimethyl-7-oxo-7-[4-(1-pyrrolidinyl)phenyl]-2,4-heptadienamide (CAS No. 1051944-80-9), (2E,4E,6R)—N-hydroxy-7-[4-[[(4-methoxyphenyl)methyl]amino]phenyl]-4,6-dimethyl-7-oxo-2,4-heptadienamide (CAS No. 1051944-77-4), (2E,4E,6R)-7-[4-(cyclopentylamino)phenyl]-N-hydroxy-4,6-dimethyl-7-oxo-2,4-heptadienamide (CAS No. 1051944-78-5), (2E,4E,6R)—N-hydroxy-4,6-dimethyl-7-oxo-7-[4-[(phenylmethyl)amino]phenyl]-2,4-heptadienamide (CAS No. 1051944-76-3), (2E,4E,6R)—N-hydroxy-4,6-dimethyl-7-[4-[(1-methylethyl)amino]-phenyl]-7-oxo-2,4-heptadienamide (CAS No. 1051944-74-1), (2E,4E,6R)-7-[4-(dibutylamino)phenyl]-N-hydroxy-4,6-dimethyl-7-oxo-2,4-heptadienamide (CAS No. 1051944-72-9), (2E,4E,6R)-7-[4-(diethylamino)phenyl]-N-hydroxy-4,6-dimethyl-7-oxo-2,4-heptadienamide (CAS No. 1051944-70-7), (2E,4E,6R)-7-[4-(dipropylamino)phenyl]-N-hydroxy-4,6-dimethyl-7-oxo-2,4-heptadienamide (CAS No. 1051944-71-8), (2E,4E,6R)—N-hydroxy-4,6-dimethyl-7-[4-[(2-methylpropyl)amino]phenyl]-7-oxo-2,4-heptadienamide (CAS No. 1051944-75-2), (2E,4E,6R)-7-[4-[bis[(4-methoxyphenyl)methyl]amino]phenyl]-N-hydroxy-4,6-dimethyl-7-oxo-2,4-heptadienamide (CAS No. 1051944-73-0), N-hydroxy-4-methoxy-ε,ε-dimethyl-ζ-oxo-benzeneheptanamide (CAS No. 1044238-80-3), 9-[1,1'-biphenyl]-4-yl-N-hydroxy-9-oxo-2,4-nonadienamide (CAS No. 1025304-96-4), 6-[[4-[3-

(hydroxyamino)-1,3-dioxopropyl]phenyl]amino]-3-pyridinecarboxylic acid (CAS No. 867336-59-2), N-hydroxy-β,4-dimethyl-γ-oxo-benzenebutanamide (CAS No. 861777-21-1), 7-[4-(dimethylamino)phenyl]-N-hydroxy-4,6-dimethyl-7-oxo-2,4-heptadienamide (CAS No. 503610-77-3), (2E,4E,6R)-7-[4-(dimethylamino)phenyl]-N-hydroxy-6-methyl-7-oxo-2,4-heptadienamide (CAS No. 674767-32-9), (2E,4E,6R)-7-(4-aminophenyl)-N-hydroxy-4,6-dimethyl-7-oxo-2,4-heptadienamide (CAS No. 528854-93-5), N-hydroxy-ε-oxo-4-phenoxy-benzenehexanamide (CAS No. 461404-99-9), (E,E)-N-hydroxy-7-[(4-biphenyl)carbonyl]-2,4-heptadienamide (CAS No. 362671-60-1), (2E,4E,6R)—N-hydroxy-4,6-dimethyl-7-[4-(methylamino)phenyl]-7-oxo-2,4-heptadienamide (CAS No. 528854-92-4), 4'-chloro-N-hydroxy-η-oxo-[1,1'-biphenyl]-4-octanamide (CAS No. 461404-93-3), 4'-chloro-N-hydroxy-ζ-oxo-[1,1'-biphenyl]-4-heptanamide (CAS No. 461404-92-2), N-hydroxy-7-[4-(4-morpholinyl)benzoyl]heptanamide (CAS No. 362670-88-0), N-hydroxy-7-[4-(1-piperidinyl)benzoyl]heptanamide (CAS No. 362670-85-7), N-hydroxy-η-oxo-4-(4-phenyl-1-piperazinyl)-benzeneoctanamide (CAS No. 362670-82-4), N-hydroxy-η-oxo-4-[(3-pyridinylmethyl)-amino]-benzeneoctanamide (CAS No. 362670-79-9), N-hydroxy-η-oxo-4-(1-piperazinyl)-benzeneoctanamide (CAS No. 362670-72-2), N-hydroxy-η-oxo-4-(2-pyridinylamino)-benzeneoctanamide (CAS No. 362670-73-3), 4-[4-[8-(hydroxyamino)-1,8-dioxooctyl]phenyl]-1-piperazinecarboxylic acid 1,1-dimethylethyl ester (CAS No. 362670-69-7), N-hydroxy-4-(methylphenylamino)-η-oxo-benzeneoctanamide (CAS No. 362670-66-4), N-hydroxy-7-[4-(4-methoxyphenyl)benzoyl]heptanamide (CAS No. 362670-48-2), N-hydroxy-6-(4-methoxybenzoyl)-hexanamide (CAS No. 362670-37-9), N-hydroxy-8-(benzoyl)octanamide (CAS No. 362670-36-8), N-hydroxy-5-(benzoyl)pentanamide (CAS No. 362670-35-7), N-hydroxy-7-(4-phenoxybenzoyl)heptanamide (CAS No. 362670-31-3), N-hydroxy-7-[(4-biphenyl)carbonyl]heptanamide (CAS No. 362670-01-7) and 4-(dimethylamino)-N-hydroxy-ε,γ-dimethyl-ζ-oxo-benzeneheptanamide (CAS No. 362669-82-7).

Illustrative examples of a compound of general formula (III) include, but are not limited to, N-hydroxy-6-methoxy-ε-oxo-2-naphthalenehexanamide (CAS No. 110842-40-5), N-hydroxy-ζ-oxo-2-naphthaleneheptanamide (CAS No. 362670-38-0), N-hydroxy-η-oxo-2-naphthaleneoctanamide (CAS No. 362669-68-9), N-hydroxy-α-methyl-η-oxo-2-naphthaleneoctanamide (CAS No. 362671-29-2), N-hydroxy-6-methoxy-η-oxo-2-naphthaleneoctanamide (CAS No. 362670-32-4), N-hydroxy-ε-oxo-2-naphthalenehexanamide (CAS No. 461404-94-4) and N-hydroxy-β-methyl-η-oxo-2-naphthaleneoctanamide (CAS No. 362671-55-4).

A combination of a histone deacetylase inhibitor, such as a compound of general formula (II), and a compound of general formula (I) is generally able to effect, e.g. cause or induce, or to prevent an alteration of the pattern of a posttranslational histone modification, such as histone methylation and histone acetylation. The pattern of a posttranslational histone modification may also be at the gene locus of a DACT protein. Typically a combination of a histone deacetylase inhibitor and compound of general formula (I) is able to effect the removal of a transcriptionally repressive posttranslational histone modification at an amino acid position and/or to effect the attachment of a transcriptionally activating posttranslational histone modification at an amino acid position. A combination of a histone deacetylase inhibitor and compound of general formula (I) may also be able to prevent the attachment of a transcriptionally repressive posttranslational histone modification at an amino acid position and/or the removal of a transcriptionally activating posttranslational histone modification at an amino acid position. A respective combination is usually also capable of effecting a combination of the removal of a transcriptionally repressive posttranslational histone modification and the attachment of a transcriptionally activating posttranslational histone modification. It may also be capable of preventing a combination of the attachment of a transcriptionally repressive posttranslational histone modification and the removal of a transcriptionally activating posttranslational histone modification.

Examples of an activating posttranslational histone modification that a combination of a histone deacetylase inhibitor and a compound of general formula (I) is generally able to effect, and/or the removal of which it is typically able to prevent, include, but are not limited to, the methylation of lysine 4 on histone 3, the acetylation of lysine 9 on histone 3, and the acetylation of lysine 14 on histone 3. Examples of transcriptionally repressive posttranslational histone modification that a combination of a histone deacetylase inhibitor and a compound of general formula (I) is generally able to remove, and/or the attachment of which it is typically able to prevent, include, but are not limited to, the methylation of lysine 9 on histone 3, the methylation of lysine 27 on histone 3, and the methylation of lysine 20 on histone 4. As an illustrative example, FIG. 5C depicts that a combination of 3-deazaneplanocin A and Trichostatin A is capable of effecting increased levels of a methylation of lysine 4 on histone 3, an acetylation of lysine 9 and/or lysine 14 on histone 3. The Figure also illustrates that a combination of these two compounds is capable of effecting reduced levels of a methylation of lysine 27 on histone 3, of a methylation of lysine 9 on histone 3 and of a methylation of lysine 20 on histone 4.

In some embodiments the compound of general formula (I) (supra) and the histone deacetylase inhibitor are administered sequentially. In some embodiments the compound of general formula (I) and the histone deacetylase inhibitor are administered in an at least substantially simultaneous manner. In some embodiments the compound of general formula (I) and the histone deacetylase inhibitor are included in the same pharmaceutical composition. In some embodiments the combination is administered to the patient by one or more of the routes consisting of enteral, intravenous, intraperitoneal, inhalation, intramuscular, subcutaneous and oral. In some embodiments the compound of general formula (I) and the histone deacetylase inhibitor are administered by the same route. In other embodiments the compound of general formula (I) is administered by a different route than the histone deacetylase inhibitor.

Administration "in combination with" one or more further therapeutic agents includes simultaneous (concurrent) and consecutive administration in any order.

There have been 11 human histone deacetylases identified and they are subdivided into class I (histone deacetylases 1, 2, 3, 8, 11) and class II histone deacetylases (histone deacetylases 4, 5, 6, 7, 9, 10) based on sequence and functional homology. In addition, there are 7 co-factor dependent deacetylases that are categorized as class III histone deacetylases or sirtuins. Histone deacetylase inhibitors induce hyperacetylation of histone tails, resulting in a relaxation of the DNA chromatin structure and reactivation of suppressed genes.

Also provided are methods for treating or preventing a disease or disorder by administering to a patient in need of such treatment a substance that modulates the activity and/or the amount of a DACT protein. In some embodiments the disease or disorder to be treated or prevented involves an aberrant component of the Wnt/β-catenin signal transduction pathway, which may be due to a mutation or germline alteration. The disease or disorder to be treated or prevented with the methods of the invention may for example be cancer.

The term "preventing" refers to decreasing the probability that an organism contracts or develops an abnormal condition.

"Treating" or "treatment" or "alleviation" refers to both therapeutic treatment and prophylactic or preventative measures, wherein the object is to prevent, slow down (lessen) or at least partially alleviate or abrogate an abnormal, including pathologic, condition in the organism. Those in need of treatment include those already with the disorder as well as those prone to having the disorder or those in whom the disorder is to be prevented (prophylaxis). When the Wnt-mediated disorder is cancer, a subject or mammal is successfully "treated" or shows a reduced tumour burden if, after having undergone a treatment that includes increasing the amount and/or the activity of a DACT protein according to the present invention, the individual shows observable and/or measurable reduction in, or absence of, one or more of the following: reduction in the number of cancer cells or absence of the cancer cells; reduction in the tumour size; inhibition (i.e., slow to some extent and preferably stop) of cancer cell infiltration into peripheral organs including the spread of cancer into soft tissue and bone; inhibition (i.e., slow to some extent and preferably stop) of tumour metastasis; inhibition, to some extent, of tumour growth; and/or relief to some extent, one or more of the symptoms associated with the specific cancer; reduced morbidity and mortality, and improvement in quality of life issues. To the extent the use or method of the invention may prevent growth and/or kill existing cancer cells, it may be cytostatic and/or cytotoxic. Reduction of these signs or symptoms may also be felt by a respective patient.

The above parameters for assessing successful treatment and improvement in the disorder are readily measurable by routine procedures familiar to a physician. For cancer therapy, efficacy can be measured, for example, by assessing the time to disease progression (TDP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

The term "administering" relates to a method of incorporating a compound into one or more cells or tissues of an organism.

The term "therapeutic effect" refers to the inhibition or activation of factors causing or contributing to the abnormal condition. A therapeutic effect relieves to some extent one or more of the symptoms of the abnormal condition.

The term "aberration" or "aberrant", in conjunction with the function of a cellular signal transduction process, refers to a component of such a process, e.g. a kinase, that is over- or under-expressed in an organism, altered such that its catalytic activity is lower or higher than corresponding wild-type activity, altered such that it can no longer interact with a natural binding partner, is no longer modified by another factor, e.g. protein or protein phosphatase, or no longer interacts with a natural binding partner.

The abnormal condition caused by a reduced amount or activity of a DACT protein may be prevented or treated when the cells or tissues of the organism exist within the organism or outside of the organism. Cells existing outside the organism can be maintained or grown in cell culture dishes. For cells harboured within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques, and carrier techniques.

The abnormal condition can also be prevented or treated by administering a compound to a group of cells having an aberration in the Wnt/β-catenin signal transduction pathway, with the cells being included or part of an organism. The effect of administering a compound on organism function can then be monitored. The organism may or instance be a mammal, such as a mouse, a rat, a rabbit, a guinea pig, a goat, a dog, a monkey or an ape. In some embodiments the organism is a human.

The term "abnormal condition" refers to a function in the cells or tissues of an organism that deviates from their normal or standard functions in that organism. An abnormal condition can relate to cell proliferation, cell differentiation, or cell survival. The terms "cell proliferative disorder" and "proliferative disorder" refer to disorders that are associated with some degree of abnormal cell proliferation such as a tumour. The word "tumour", as used herein, refers to all neoplastic cell growth and proliferation, whether malignant or benign, and all pre-cancerous and cancerous cells and tissues. Accordingly, the word "tumourigenesis" refers to the generation, including the induction, of neoplastic cell growth and proliferation. An example of tumorigenesis is carcinogenesis, the generation of a cancer cell, which is typically the result of a transformation of a somatic cell into a cancer cell, including a cancer stem cell.

Abnormal cell proliferative conditions include cancer, fibrotic and mesangial disorders, abnormal angiogenesis and vasculogenesis, wound healing, psoriasis, diabetes mellitus, and inflammation. Furthermore, the proliferative disorders can relate to conditions in which programmed cell death (apoptosis) pathways are abrogated. As a number of proteins the expression of which is under control of the Wnt/β-catenin signal transduction pathway are associated with the apoptosis pathways, aberrations in the Wnt/β-catenin signal transduction pathway can lead to cell immortality.

In the methods and uses of the invention an additional compound may be employed, for example a compound that alters the activity of a dishevelled protein, e.g. an antagonist thereof. Examples of low molecular weight organic compounds that are antagonists of Dvl PDZ domain interactions are indole-2-carbinol derivatives, which have been disclosed by You et al. (*Mol Cancer Ther* (2008) 7, 6, 1633-1638). Further suitable examples of antagonists of Dvl PDZ domain interactions are indole-2-carboxylic acid amide derivatives, disclosed by Mahindroo et al. (*Bioorganic & Medicinal Chemistry Letters* (2008) 18, 946-949).

A further example of an additional compound that may be used, for example in combination with 3-Deazaneplanocin A and a histone deacetylase inhibitor or with a composition as described above, is a compound that inhibits the function of protein kinases. Examples of low molecular weight compounds that have been reported to inhibit the function of protein kinases include, but are not limited to, bismonocyclic, bicyclic or heterocyclic aryl compounds (international patent application WO 92/20642), vinylene-azaindole derivatives (international patent application WO 94/14808), 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (EP patent Application No. 0 566 266 A1), seleoindoles and selenides (international patent application WO 94/03427), tricyclic polyhydroxylic compounds (international patent application WO 92/21660), and benzylphosphonic acid compounds (international patent application WO 91/15495).

Other examples of substances capable of modulating protein kinase activity include, but are not limited to, indolinones, tyrphostins, quinazolines, quinoxolines, and quinolines. The indolinones, quinazolines, tyrphostins, quinolines, and quinoxolines referred to above include well known compounds described in the literature.

A further example of a compound which may be used in conjunction with a compound, pharmaceutical composition, method or use of the invention is an anti-hormonal agent that acts to regulate, reduce, block, or inhibit the effects of hormones that can promote the growth of cancer. Such compounds are often in the form of systemic or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY1 17018, onapristone, and FARESTON® toremifene; anti-progesterones; estrogen receptor down-regulators (ERDs); agents that function to suppress or shut down the ovaries, for example, luteinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above. The term "pharmaceutically acceptable" as used herein refers to the property of matter to be administered, e.g. compositions, carriers, diluents or active compounds, as being capable of administration to or upon a human at least essentially without giving rise to undesirable physiological effects such as nausea, dizziness or gastric upset in the dose or amount used. In particular, the used amount or dose of such matter does not cause such effects to a degree that would prohibit administration of the composition.

A "growth inhibitory agent" when used herein refers to a compound or composition which inhibits growth of a cell, especially a cancer cell having Wnt signaling activity, either in vitro or in vivo. Thus, the growth inhibitory agent may be one which significantly reduces the percentage of such cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. The taxanes (paclitaxel and docetaxel) are anticancer drugs both derived from the yew tree. Docetaxel (TAXOTERE®), derived from the European yew, is a semisynthetic analogue of paclitaxel (TAXOL®). Paclitaxel and docetaxel promote the assembly of microtubules from tubulin dimers and stabilize microtubules by preventing depolymerization, which results in the inhibition of mitosis in cells.

Examples of other active ingredients that may be included in a pharmaceutical composition include, but are not limited to, a nucleic acid alkylator, an anthracycline, an antibiotic, an aromatase inhibitor, a folate antagonist, an estrogen receptor modulator, an inorganic aresenate, a nitrosourea, an osteoclast inhibitor, a platinum containing compound, a retinoid, a topoisomerase 1 inhibitor, a topoisomerase 2 inhibitor, a thymidylate synthase inhibitor, an aromatase inhibitor, a cyclo-oxygenase inhibitor, an isoflavone, a tyrosine kinase inhibitor, a growth factor, a bisphosphonate, and a monoclonal antibody.

Alkylators that may be included in the pharmaceutical composition of the present invention include but are not limited to busulfan (Myleran®, Busilvex®), chlorambucil (Leukeran®), ifosfamide (Mitoxana®, with or without MESNA), cyclophosphamide (Cytoxan®, Neosar®), glufosfamide, melphalan/L-PAM (Alkeran®), dacarbazine (DTIC-Dome®), and temozolamide (Temodar®). As an illustrative example, the compound 2-bis[(2-chloroethyl)amino]tetrahydro-2H-1,3,2-oxazaphosphorine, 2-oxide, also commonly known as cyclophosphamide, is an alkylator used in the treatment of stages III and IV malignant lymphomas, multiple myeloma, leukemia, mycosis fungoides, neuroblastoma, ovarian adenocarcinoma, retinoblastoma, and carcinoma of the breast.

Anthracyclines that may be included in the pharmaceutical composition of the present invention include, but are not limited to, doxorubicin (Adriamycin®, Doxil®, Rubex®), mitoxantrone (Novantrone®), idarubicin (Idamycin®), valrubicin (Valstar®), and epirubicin (Ellence®). As one example the compound (8S,10S)-10-(4-amino-5-hydroxy-6-methyl-tetrahydro-2H-pyran-2-yloxy)-6,8,11-trihydroxy-8-(2-hydroxyacetyl)-1-methoxy-7,8,9,10-tetrahydrotetracene-5,12-dione, more commonly known as doxorubicin, is a cytotoxic anthracycline antibiotic isolated from cultures of *Streptomyces peucetius* var. *caesius*. Doxorubicin has been used successfully to produce regression in disseminated neoplastic conditions such as acute lymphoblasttic leukemia, acute myeloblastic leukemia, Wilm's tumour, neuroblastoma, soft tissue and bone sarcomas, breast carcinoma, ovarian carcinoma, transitional cell bladder carcinoma, thyroid carcinoma, lymphomas of both Hodgkin and non-Hodgkin types, bronchogenic carcinoma, and gastric carcinoma.

Antibiotics that may be included in the pharmaceutical composition of the present invention include but are not limited to dactinomycin, actinomycin D (Cosmegen®), daunorubicin/daunomycin (Cerubidine®, DanuoXome®), bleomycin (Blenoxane®), epirubicin (Pharmorubicin®) and mitoxantrone (Novantrone®). Aromatase inhibitors useful in the practice of the present invention include but are not limited to anastrozole (Arimidex®) and letrozole (Femara®). Bisphosphonate inhibitors that may be included in the pharmaceutical composition of the present invention include but are not limited to zoledronate (Zometa®).

Cyclooxygenase inhibitors that may be included in the composition of the present invention include but are not limited to acetylsalicylic acid (Aspirin®), celecoxib (Celebrex®) and rofecoxib (Vioxx®, Ceoxx®, Ceeoxx®). Estrogen receptor modulators that may be included in the composition of the present invention include but are not limited to tamoxifen (Nolvadex®) and fulvestrant (Faslodex®). Folate antagonists that may be included in the composition of the present invention include but are not limited to methotrexate (Trexall®, Rheumatrex®) and trimetrexate (Neutrexin®). As an illustrative example, the compound (S)-2-(4-(((2,4-diaminopteridin-6-yl)methyl)methylamino)benzamido)pentanedioic acid, commonly known as methotrexate, is an antifolate drug that has been used in the treatment of gestational choriocarcinoma and in the treatment of patients with chorioadenoma destruens and hydatiform mole. It is also useful in the treatment of advanced stages of malignant lymphoma and in the treatment of advanced cases of mycosis fungoides.

As noted above, the present invention also relates to methods of identifying a cell that is at risk of becoming tumourigenic, including cancerogenic, and/or a cell that has a predisposition to turn tumourigenic. The present invention further relates to methods of prognosis, assessing the disease state, predicting the responsiveness of an individual, including a tumor of an individual, to a therapy, assessing the likelihood of a response to a therapy, predicting the course of disease, and monitoring a therapy of a cancer disease of an individual known to have or suspected to develop a tumour such as cancer. In some embodiments a respective method is a method of predicting whether a neoplasm is sensitive to a combination of a compound of the general formula (I) and a histone deacetylase inhibitor. The neoplasm, for example a tumor such as cancer, may in some embodiments be included in a mammal.

These methods include assessing one or more of three parameters. The first of these parameters is the amount of a DACT protein in the respective cell or in a cell of the respective individual. Such a cell may also have been isolated from the corresponding individual or be a cell of a tissue sample taken from the corresponding individual.

The second of the aforementioned three parameters is the activity of the DACT protein in the cell, and the third parameter is the pattern of histone modification, generally histone methylation and/or histone acetylation. Where the amount or the activity of the DACT protein in the cell or in the tissue sample is assessed, a reduced amount or activity of the DACT protein is an indication of an increased risk that the cell will become tumourigenic. In the context of diagnosis such a reduced activity and/or cellular amount of the DACT protein indicates an elevated risk of the individual to develop cancer. When predicting the sensitivity of a neoplasm, a reduced amount or activity of the DACT protein may be an indication that a neoplasm is sensitive to a combination of a compound of the general formula (I) and a histone deacetylase inhibitor.

The pattern of histone methylation and/or histone acetylation may for instance be assessed at the gene locus of a DACT protein. The gene locus of a DACT protein is understood to refer to the region that includes the sequence, which encodes the DACT protein. It may in some embodiments refer to the region from about 900 bp downstream of the transcription start of the respective gene, including from about 600 bp downstream thereof, up to the end of the sequence encoding the DACT protein. In some embodiments it may refer to the region from about 600 bp downstream of the transcription start of the gene of the DACT protein up to the transcription start of the gene and may include the coding region of the gene. A reduced acetylation of lysine 9 and/or lysine 14 on histone 3 is an indication that a cell has a predisposition to turn tumourigenic. In the context of diagnosis a reduced acetylation of lysine 9 and/or lysine 14 on histone 3 is an indication of an increased risk that the individual will develop cancer. An increased methylation of lysines 4 and 27 on histone 3 is also an indication that a cell has a predisposition to turn tumourigenic. An additionally increased methylation of lysine 20 on histone 4 and of lysine 9 on histone 3 is typically a further indication that a cell has a predisposition to turn tumourigenic. Likewise, in the context of diagnosis an elevated value of methylation of lysines 4 and 27 on histone 3 is an indication of an increased risk that the individual will develop cancer. An additionally increased methylation of lysine 20 on histone 4 and of lysine 9 on histone 3 is typically a further indication that the individual has an increased risk to develop cancer.

In some embodiments such a method is a method of assessing the chances that an individual will respond to a therapy that includes a combined administration of a compound of the general formula (I) (supra) and a histone deacetylase inhibitor. A reduced acetylation of lysine 9 and/or lysine 14 on histone 3 is an indication that the respective individual will respond to a therapy that includes a combined administration of a compound of the general formula (I) and a histone deacetylase inhibitor. Further, an increased methylation of lysines 4 and 27 on histone 3 is an indication that the respective individual will respond to such a therapy. An additionally increased methylation of lysine 20 on histone 4 and of lysine 9 on histone 3 is typically a further indication that the individual will respond to such a therapy.

In some embodiments the present methods of the invention include detecting the expression, the subcellular localisation and/or the activity of the DACT protein, for example in an organism or in a tissue or a cell thereof. As an illustrative example, the cellular amount, the expression, the subcellular localisation and/or the activity of the DACT protein may be monitored over a period of time.

The present methods of the invention may furthermore include comparing the results of measuring the cellular amount, the expression, the subcellular localisation and/or the activity of the DACT protein with results of a control measurement (or "reference" measurement). In such a control measurement one or more of the above named parameters, i.e. the amount of a DACT protein, the activity of a DACT protein, and the pattern of histone modification are assessed in control tissue or a control cell. Such control tissue or control cell is generally of at least essentially no risk of becoming tumorigenic In some embodiments the one or more parameters are compared to average values, possibly statistically analysed, that have been obtained in a number of previous control measurements. In some embodiments of diagnostic background, for instance where in doubt in view of a potentially small difference to pre-existing average data, one or more tissue samples from the same individual may be used for carrying out one or more control measurements. A respective sample is typically taken from tissue that is expected to have a comparably low risk of turning tumourigenic or that is known to be healthy tissue without a potential risk of becoming tumourigenic.

In the context of a method of identifying a compound that is suitable for arresting, inhibiting or preventing tumourigenesis (see below) a control measurement may include the use of conditions that do not modulate the cellular amount, the expression, the subcellular localisation and/or the activity of a DACT protein. In comparing cellular amount, expression, and/or activity, detected levels may for example be compared to a control level. The term "control level" as used herein refers to the number of molecules of the respective protein, e.g. in a cell, a mRNA or protein expression level of a DACT protein, as well as to an activity level of a DACT protein in a control sample. The term thus includes both a normal control level and a cancer control level (see also below). The term can refer to a single reference measurement or to a plurality of reference measurements. In some embodiments the control level may be a database of expression or activity values from previously conducted measurements. The term "customary level" refers to a level of expression of a DACT protein or an activity level of a DACT protein detected in a normal, healthy individual or in a population of individuals known not to be suffering from a neoplasm, including cancer. A normal individual is one with no clinical symptoms of a respective neoplasm.

According to the present invention, a gene expression level or an activity level or an amount of a protein, e.g. in a cell, is deemed to be "altered" or to "differ" when gene expression/activity/amount is increased or decreased by about 10%, about 25%, about 50%, about 75%, about 100%, or higher, as compared to the control level. Alternatively, an expression level or an activity level is deemed "increased" or "decreased" when gene expression/or an activity is increased or decreased by at least about 0.1, at least about 0.2, at least about 1, at least about 2, at least about 5, or at least about 10 or more fold as compared to a control level.

The present method of the invention may include altering the amount of a Dishevelled protein, such as Dishevelled-1, Dishevelled-2 or Dishevelled-3, in the cell. In some embodiments the method includes preventing, inhibiting, arresting or reversing activation of the Dishevelled protein. In typical embodiments, modulating the amount or the activity of a DACT protein may result in modulating the activity of the Dishevelled protein and in degradation of the Dishevelled protein in the cell.

The compound of general formula (I) and the histone deacetylase inhibitor may also be used in the form of a metabolite or a prodrug.

As used herein, the term "prodrug" means a compound which is converted or released within the human or animal body, e.g. enzymatically, mechanically or electromagnetically, into its active form that has medical effects. A "prodrug" is accordingly a pharmacologically inactive derivative of a parent "drug" molecule. It requires spontaneous or enzymatic biotransformation within the physiological system of the human or animal to which it is administered. "Prodrugs" are commonly used in the art to overcome problems associated with stability, toxicity, lack of specificity, or limited bioavailability. They often offer advantages of solubility, tissue compatibility, or delayed release in the mammalian organism. As an illustrative example, a "prodrug" may be a metal triangulo compound with a protective group shielding a moiety or functional group thereof and thereby reversibly suppressing the activity of the metal triangulo compound. A respective "prodrug" may become pharmaceutically active in vivo or in vitro when the protective group undergoes solvolysis or enzymatic removal. As a further illustrative example, a functional group may only be introduced into a compound of general formula (I) upon biochemical transformation such as oxidation, phosphorylation, or glycosylation. Thus a respective "prodrug" may only be converted into a compound of general formula (I) by an enzyme, gastric acid, etc. in the human or animal body. The "prodrug" of a compound of general formula (I) may be a hydrate or a non-hydrate. Common "prodrugs" include acid derivatives such as esters prepared by reaction of parent acids with a suitable alcohol (e.g., a lower alkanol), amides prepared by reaction of the parent acid compound with an amine (e.g., as described above), or basic groups reacted to form an acylated base derivative (e.g., a lower alkylamide).

The compounds described herein, as well as compounds identified by a method of the invention, can be administered to a cell, an animal or a human patient per se, or in pharmaceutical compositions where they are mixed with other active ingredients, as in combination therapy, or suitable carriers or excipient(s), including stabilizers, solubilizers and emulsifiers. Such carriers, excipients or stabilizers are usually pharmaceutically acceptable in that they are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®. Exemplary routes include, but are not limited to, oral, transdermal, and parenteral delivery.

Suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. Suitable routes of administration may, for example, include depot, oral, rectal, transmucosal, or intestinal administration, parenteral delivery, including intramuscular, subcutaneous, intravenous, intramedullary injections, as well as intrathecal, direct intraventricular, intraperitoneal, intranasal, or intraocular injections. One may also administer the compound or pharmaceutical composition in a local rather than systemic manner, for example, via injection of the compound directly into a solid tumour, such as in a depot or sustained release formulation. Furthermore, a respective compound or pharmaceutical composition may be used in a targeted drug delivery system, for example, in a liposome coated with a tumour-specific antibody. Such liposomes may for example be targeted to and taken up selectively by a tumour.

Furthermore, one may administer the drug in a targeted drug delivery system, for example, in a liposome coated with a tumour-specific antibody. The liposomes will be targeted to and taken up selectively by the tumour.

Pharmaceutical compositions according to the present invention may be manufactured in a manner that is itself known, e. g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers including excipients and auxiliaries that facilitate processing of the active compounds into preparations that can be used pharmaceutically. Proper formulation is dependent upon the route of administration chosen.

For injection, a compound according to the invention may be formulated in aqueous solutions, for instance in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated.

Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatine, as well as soft, sealed capsules made of gelatine and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e. g. gelatine for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e. g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

A pharmaceutical carrier for the hydrophobic compounds of the invention is a co-solvent system including benzyl alcohol, a non-polar surfactant, a water-miscible organic polymer, and an aqueous phase. The co-solvent system may be the VPD co-solvent system. VPD is a solution of 3% w/v benzyl alcohol, 8% w/v of the non-polar surfactant polysorbate 80, and 65% w/v polyethylene glycol 300, made up to volume in absolute ethanol. The VPD co-solvent system (VPD: D5W) consists of VPD diluted 1:1 with a 5% dextrose in water solution.

This co-solvent system dissolves hydrophobic compounds well, and itself produces low toxicity upon systemic administration. Naturally, the proportions of a co-solvent system may be varied considerably without destroying its solubility and toxicity characteristics.

Furthermore, the identity of the co-solvent components may be varied: for example, other low-toxicity non-polar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Other delivery systems for hydrophobic pharmaceutical compounds may also be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may include suitable solid or gel phase carriers or excipients. Examples of such carriers or excipients include but are not limited to calcium carbonate, calcium phosphate, various sugars, starches, cellulose derivatives, gelatine, and polymers such as polyethylene glycols.

Many of the compounds that may be used in the invention may be provided as salts with pharmaceutically compatible counter-ions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

For any compound used in the methods of the invention, the therapeutically effective dose can be estimated initially from cell culture assays. For example, a dose can be formulated in animal models to achieve a circulating concentration range that includes the IC50 as determined in cell culture (i.e., the concentration of the test compound which achieves a half-maximal inhibition of the DACT activity or reduction of the amount of the DACT protein in the cell). Such information can be used to more accurately determine useful doses in humans.

Toxicity and therapeutic efficacy of the compounds described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. It may be desired to use compounds that exhibit high therapeutic indices. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition.

Dosage amount and interval may be adjusted individually to provide plasma levels of the active moiety which are sufficient to maintain the DACT, modulating effects, or minimal effective concentration (MEC). The MEC will vary for each compound but can be estimated from in vitro data; e.g., the concentration necessary to achieve 50-90% inhibition of the DACT protein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen that maintains plasma levels above the MEC for 10-90% of the time, for example from about 30 to about 90%, such as from about 50 to about 90%. In cases of local administration or selective uptake, the effective local concentration of the drug may not be related to plasma concentration. The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for instance include metal or plastic foil, such as a blister pack. The pack or dispenser device may be accompanied by instructions for administration. The pack or dispenser may also be accompanied with a notice associated with the container in a form prescribed by a governmental agency regulating the manufacture, use, or sale of pharmaceuticals, which notice is reflective of approval by the agency of the form of the compound for human or veterinary administration. Such notice, for example, may be the labeling approved by the U.S. Food and Drug Administration or other government agency for prescription drugs, or the approved product insert.

Compositions according to the invention formulated in a compatible pharmaceutical carrier may also be prepared, placed in an appropriate container, and labeled for treatment of an indicated condition. Suitable conditions indicated on the label may include, for example, treatment of cancer.

According to this invention, the method, compound and pharmaceutical composition can be used in the treatment of a cell proliferative disorder, such as a tumour or cancer. Any tumour or cancer may be selected for treatment, including for instance a benign tumour and a metastatic malignant tumour. Examples include, but are not limited to, haematological malignancies and solid tumours. Solid tumours include for instance a sarcoma, arising from connective or supporting tissues, a carcinoma, arising from the body's glandular cells and epithelial cells or a lymphoma, a cancer of lymphatic tissue, such as the lymph nodes, spleen, and thymus. Examples of a solid tumour include, but are not limited to, breast cancer, lung cancer, a brain tumour, a neuroblastoma, colon cancer, rectal cancer, bladder cancer, a liver tumour, a pancreatic tumour, ovarian cancer, prostate cancer and a melanoma.

As explained above, the present invention encompasses the diagnostic, prognostic, and therapeutic use of a DACT protein in a cell, including its amount or activity. In particular based on the amount or activity methods and uses are provided inter alia of monitoring a therapy, predicting a response to therapy, detecting minimal residual disease and/or prognosis of disease. Based on the inventors' findings the invention also provides methods of identifying a compound that is capable of preventing, inhibiting, arresting or reversing tumourigenesis, including carcinogenesis, in a cell and/or of inducing apoptosis in a tumour cell. Some of these methods are in vivo or ex vivo methods. Some of the methods are in-vitro methods of identifying a respective compound. The compound may be capable of forming a complex with a DACT protein, or a functional fragment thereof. Some methods according to the invention include exposing the components of this complex to each other, whether in-vitro or in-vivo. One such method is an in-vitro method, which includes contacting the components that form, or are suspected to form, a complex with each other. For example a DACT protein and a drug candidate molecule, which is suspected to form a complex with the DACT protein, may be contacted with each other. The compound may be capable of altering the complex formation between the DACT protein and a dishevelled protein. In some embodiments a respective method includes contacting the compound, a DACT protein, or a functional fragment thereof, and a dishevelled protein. In such embodiments the formation of a complex between the DACT protein and the dishevelled protein is detected.

In some embodiments the method further includes detecting the formation of the complex. Any suitable method of detecting a complex formation may be used. A detection method may, for instance, include electrophoresis, HPLC, flow cytometry, fluorescence correlation spectroscopy or a modified form of these techniques (see also above). Other techniques involve a measurement of the biomolecular binding itself. Such measurements may for instance rely on spectroscopic, photochemical, photometric, fluorometric, radiological, enzymatic or thermodynamic means (supra). An enhancement of the formation of a complex between the DACT protein and the dishevelled protein indicates that the compound is capable of preventing, inhibiting, arresting or reversing tumourigenesis in a cell and/or of inducing apoptosis in a tumour cell.

Where the method is an in-vivo or an ex vivo method it may include providing a microorganism. The microorganism expresses the DACT binding protein, with which the compound is suspected to be capable of forming a complex, the formation of a complex of which with a dishevelled protein the compound is suspected to increase or the expression of which the compound is suspected to be capable of increasing. The microorganism may in some embodiments endogenously express the DACT binding protein. In some embodiments the microorganism is a recombinant cell or a transgenic microorganism (see also above).

The present methods of the invention include adding the respective compound to the microorganism. In some embodiments of a respective method, the expression of the DACT protein is monitored. In some embodiments of a respective method the activity of the DACT protein is monitored. In some embodiments a change in cell phenotype is monitored. In some embodiments such a method includes a control measurement (see also above). The results of the control measurement are compared to the results obtained using the compound. A control measurement may for example include the use of a compound that is known not to affect the expression or the activity of the DACT binding protein, or that is known not to affect the formation between the DACT protein and the dishevelled protein.

In some embodiments a method according to the present invention includes contacting a respective microorganism, for instance a cell such as a tumour cell, with a predetermined quantity of a compound of the general formula (I) (see above) and a predetermined quantity of a histone deacetylase inhibitor. In some embodiments at least two different predetermined quantities of a compound of the general formula (I) are used. In some embodiments at least two different predetermined quantities of a combination of a compound of the general formula (I) and a histone deacetylase inhibitor are used. In some of these embodiments at least a first and a second cell are used. The first cell is contacted with the lower of the two predetermined quantities and the second cell is contacted with the higher of the two predetermined quantities. Respective embodiments may for example be a screening assay, a cytotoxity test or the determination of a dose/response curve.

In some embodiments the first cell (e.g. tumour cell) and the second cell (e.g. tumour cell) are obtained from the same patient. Such a method may for instance be a method of predicting a patient's or an animal's individual response to a combination of a compound of the general formula (I) and a histone deacetylase inhibitor. Single nucleotide polymorphisms and individual differences in gene expression usually cause individual differences between patients in responding to compounds that are administered. In some embodiments a respective method of the invention may also be a method of identifying genetic variants that influence a patient's response to a combination of a compound of the general formula (I) and a histone deacetylase inhibitor. Typically the effect of a compound applied to an animal or a patient as a drug is determined by many proteins, so that composite genetic polymorphisms in multiple genes coupled with non-genetic factors determine a response to a compound. A respective method of the invention may thus be a method of determining a patient's genotype, for example to ensure maximum efficacy with minimal adverse effects.

For some embodiments of the invention, compounds may be used in form of a library. Examples of such libraries are collections of various small organic molecules, chemically synthesized as model compounds, or nucleic acid molecules containing a large number of sequence variants.

In embodiments where a plurality of candidate compounds are analysed according to a method of the present invention in order to identify a compound capable of preventing, inhibiting, arresting or reversing tumourigenesis, such an embodiment may typically called a screening process. These candidate compounds may be analysed independent from each other, e.g. concurrently, consecutively or in any way out of phase. In in vivo or ex vivo embodiments the candidate inhibitors may for example be added to a cell culture medium or be administered to an organism, for example a mouse or a fruit fly. In some in vitro embodiments any number of steps of analysing a plurality of candidate compounds may for example be carried out automatically—also repeatedly, using for instance commercially available robots. For such purposes any number of automation devices may be employed, for instance an automated read-out system, a pipetting robot, a rinsing robot, or a fully automated screening system. As an illustrative example, the process may be an in-vitro screening process, for example carried out in multiple-well microplates (e.g. conventional 48-, 96-, 384- or 1536 well plates) using one or more automated work stations. Hence, in some embodiments the invention provides a process of high-throughput screening. The method may also be carried out using a kit of parts, for instance designed for performing the present method.

Yet other related methods are in-vivo methods that include providing a host organism. Any desired host organism may be provided as long as it is capable of accommodating and growing a tumour cell, e.g. a cancer cell. Examples of a host organism include, but are not limited to, a mammal, a fish, an amphibian and a bird. For examples of a suitable mammal see above. Any desired cancer cell may be used for this purpose (see above for examples). The method further includes introducing a cancer cell into the host organism. Furthermore the method includes the use of a compound as described above, i.e. a compound that is suspected to be capable of forming a complex with a DACT protein, to be capable of modulating the amount of a DACT binding protein, to be capable of modulating the activity of a DACT binding protein or to be capable or enhancing the formation of a complex between a DACT protein and a dishevelled protein. In some embodiments the cancer cell includes the compound. Accordingly the compound may be introduced into the cancer cell before introducing the same into the host organism. In some embodiments the compound is administered to the host organism, before, after or concurrently with introducing the cancer cell therein. Typically the compound is introduced into the cancer cell at a certain stage of the method. The method further includes monitoring the growth of tumours in the host organism.

The invention is further illustrated by the following non limiting examples and the appended figures. As one of ordinary skill in the art will readily appreciate from the disclosure of the present invention, other compositions of matter, means, uses, methods, or steps, presently existing or later to be developed that perform substantially the same function or achieve substantially the same result as the corresponding exemplary embodiments described herein may likewise be utilized according to the present invention.

EXEMPLARY EMBODIMENTS OF THE INVENTION

FIG. 1. Simplified schematic of important features of the Wnt/β-catenin pathway: (A) In the absence of Wnt signal β-catenin levels are regulated by the formation of a multiprotein complex, defining a cytosolic destruction complex. The complex includes the tumour suppressor adenomatous polyposis coli (APC), a scaffold protein axin, casein kinase 1 (CKI)) and glycogen synthase kinase 3β (GSK3β). It causes β-catenin phosphorylation, thereby marking it for ubiquitinylation and consequently degradation via the proteasome. (B) Upon binding of Wnt to the Frizzled (Fz) receptor and a low-density-lipoprotein (LDL) receptor related protein such as the LDL receptor related protein 6 (LRP6), Dvl is recruited to this receptor, leading to its activation, whereupon a cascade of events is triggered. As a result the destruction complex is inhibited, hypophosphorylated β-catenin is stabilized, accumulates and translocates to the nucleus. There it forms a complex with a T cell factor (TCF) and/or a lymphoid enhancer-binding factor (LEF), thereby activating transcription of numerous genes, including c-MYC, cyclin D1, gastrin or matrilysin. (C) It is contemplated that increasing the amount and/or the activity of a DACT according to the invention may lead to its complex formation with Dvl, thereby blocking the signal transduction pathway depicted in FIG. 1B. As a result the multiprotein complex denoted in FIG. 1A forms, β-catenin is phosphorylated and degraded.

Figure 2:
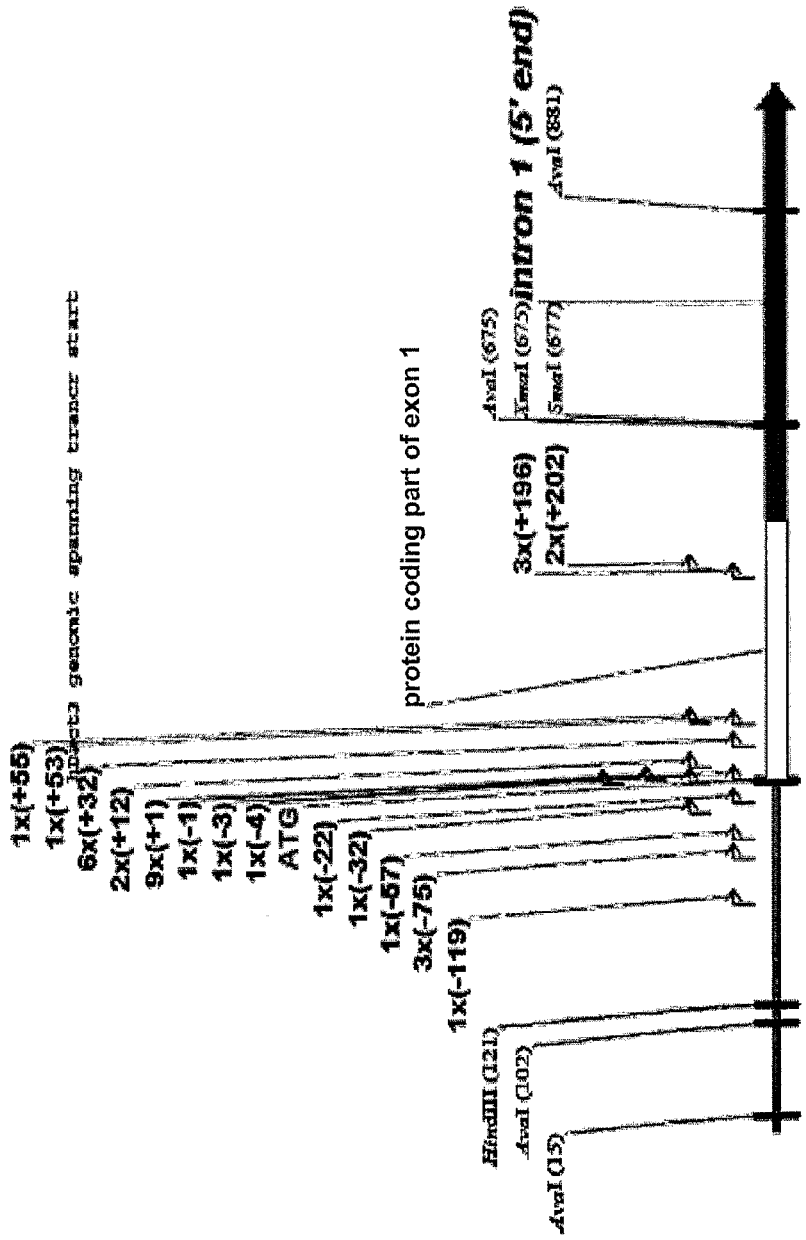
FIG. 2 depicts the mapping of the transcription start site of human DACT3.

FIG. 2 depicts the mapping of the genomic region spanning the transcription start site of human DACT3. 5'RACE was used to determine the transcription start site of DACT3 as described in the Experimental Procedures. Transcription start sites are shown in back "number of clones X (relative to ORF start codon)". The DNA sequence in the promoter region and Exon 1 is shown. The italic sequence (white box) indicates the coding region in Exon 1.

FIG. 3 shows a loss of DACT3 expression in colon cancer independently of DNA methylation. A: Hierarchical clustering of Wnt inhibitors (upper) and Wnt/β-catenin target genes (lower) in human colorectal tumors (T) and matched normal mucosa (N). White signals in the upper panel indicate above-mean expression; white signals in the lower panel indicate below-mean expression. B: RT-PCR analysis of SFRP1 and DACT1, 2 and 3 from random-selected 8 pairs of human colorectal tumor and matched mucosa. C: Methylation status of SFRP1 and DACT3 in 8 tumors determined by methylation specific PCR (MSP) assay. M1, M2, M3 and M4 represent the examined PCR regions covering the entire CpG island of DACT3 promoter. D: RT-PCR analysis of SFRP1 and DACT1, 2 and 3 in a panel of colorectal cancer cell lines compared to the normal tissue. E: Methylation status of SFRP1 and DACT1, 2 and 3 in colorectal cancer cell lines. F: Determination of methylation status of CpG sites by sequencing of bisulphite-modified DNA from normal and colorectal cancer cell lines. Arrows indicate the transcription start sites. Open cycles represent unmethylated CpGs; closed cycles denote methylated CpGs. G: MSP analysis of DACT1, 2 and 3 promoters in HCT116 cells untreated or treated with 5-AzaC and in HCT116-DNMT1/DNMT3b−/− (DKO) cells. H: RT-PCR analysis of SFRP1 and DACT1, 2 and 3 in HCT116 and DLD1 cells treated with 5-AzaC (5 µM) for 3 days and in DKO cells.

FIG. 4. Histone modifications at DACT1, 2 and 3 in colon cancer cells. ChIP assays were performed using antibodies against the indicated histone modifications and analyzed by quantitative PCR. Genomic DNA fragments covering the −3.5 kb to +3.5 kb region with respect to the transcription start site of DACT1, 2 and 3 for PCR analysis were indicated with numbers. The relative enrichments (bound/input) (Mean±SD of triplicate measurement) encompassing the indicated regions is shown for each histone marks at each gene locus. A: Histone marks at the DACT1-3 loci in HT-29 cells. B: Enrichments of H3K27me3 and H3K4me3 at the DACT3 locus in SW480 and RKO cells. C: Enrichments of H3K27me3 and H3K4me3 at the DACT3 locus in normal human intestinal epithelial cells (FHs 74 Int), non-cancerous breast epithelial MCF10A cells and lung fibroblast MRC5 cells.

FIG. 5. Effects of combination of DZNep and TSA on DACT3 and histone modifications. A: DACT3 mRNA expression analysis using Illumina Beadarray in DLD1 cells treated with 5 µM DZNep, 5 µM 5-AzaC, 200 nM TSA or their combinations. The data shown represents Mean±SD of three independent experiments. B: Indicated colorectal cancer cell lines were treated with DZNep, TSA or both. RNA was harvested and subjected to array analysis (1: DCAT2, 2: DACT2, 3: DCAT3, 4: DKK4, 5: DKK3, 6: DKKL1, 7: DKK2, 8: DKK3, 9: DKK1, 10: SFRP4, 11: SFRP2, 12: SFRP5, 13: SFRP3, 14: SFRP1). Changes of expression of known Wnt/β-catenin antagonists are shown. C: Immunoblotting analysis of bulk histone modifications induced by DZNep, TSA or both in HT29 cells and SW480 cells. D: ChIP analysis of indicated the changes of histone marks at the DACT1 and DACT3 loci in HT29 cells untreated (white bars) or treated with DZNep and TSA (black bars). The values represent the normalized enrichments against the changes of a low background region before and after the drug treatment. The data represent Mean±SD of three independent experiments.

FIG. 6. Combination of DZNep and TSA results in blockade of Wnt/β-catenin signaling and massive apoptosis in colorectal cancer cells. A: Immunoblot analysis of DACT3, DVL2, total β-catenin, and non-phosphorylated β-catenin (Active-β-catenin) in SW480 and DLD1 cells treated with DZNep (5 µM), TSA (100 nM) or both. B: Immunofluorescent images of DLD1 and SW480 cells treated with DZNep/TSA. β-catenin staining is red, nuclear staining is green (DRAQ5). C: Indicated colorectal cancer cell lines were treated as above; RNA was harvested and subjected to array analysis. Changes of expression of known Wnt/β-catenin target genes were shown using gene clustering program. White in the upper panel indicates up-regulated genes, white in the lower panel indicates down-regulated genes. D: Numeric values of data depicted in FIG. 6C (D+T=DZNep+TSA). E: DLD1 and HT29 cells were treated as in A, and cell death was determined by PI staining and FACS analysis. The data represent Mean±SD of three independent experiments. F: HT29 cells were treated as in A, and Caspase 3 activity was measured by FACS analysis. G: HT29 cells were treated as in A, followed by JC-1 staining and FACS analysis.

Figure 7:
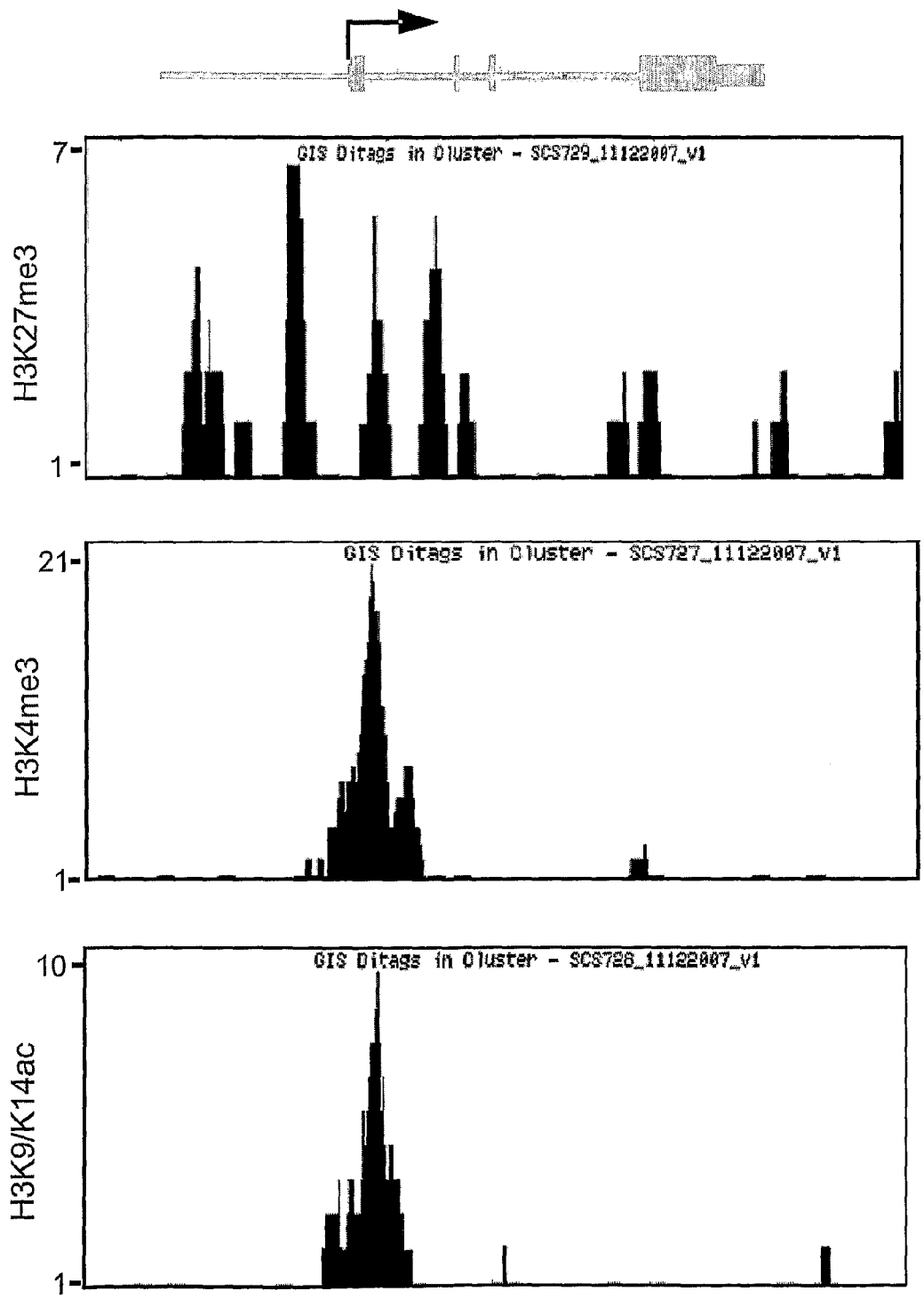
FIG. 7 depicts histone modifications at the DACT genes in cancer cells.
Figure 7:
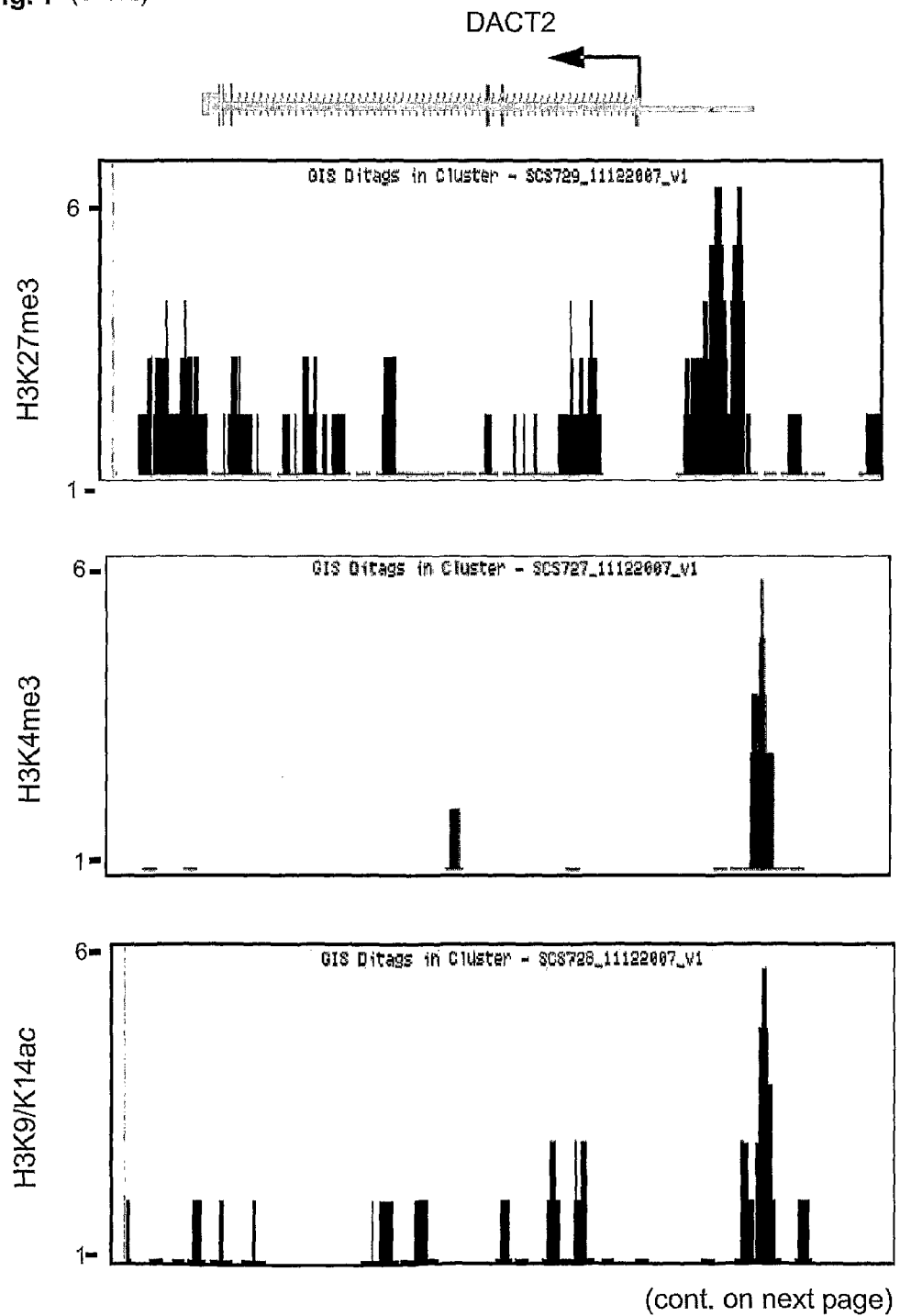
Figure 7:
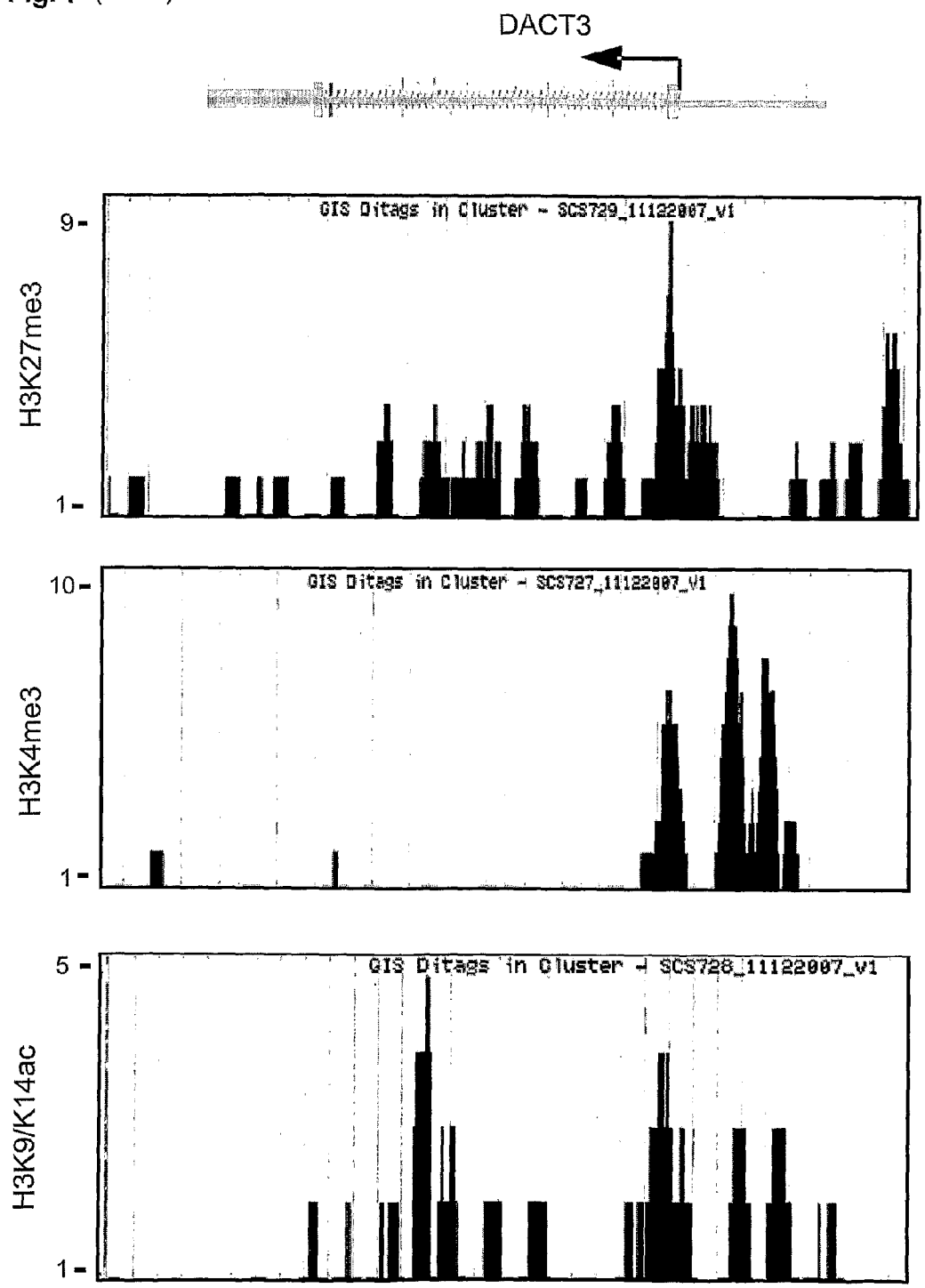

FIG. 7. Histone marks at the DACT1-DACT3 loci in SW480 cells. ChIP-sequencing of indicated histon marks of SW480 cells were performed using Solexa technology. The enrichments of H3K27me3, H3K4me3 and H3K9/14ac at the entire DACT1, 2 and 3 loci were shown.

FIG. 8. DACT3 plays a role in inhibition of Wnt/β-catenin signaling and apoptosis induction by DZNep/TSA. A: Two DLD1 stable clones expressing DACT3 shRNA (DACT3-sh1 and DACT3-sh2) or DLD1 cells expressing a non-targeting control shRNA (NC) were treated with DZNep, TSA or both. DACT3 and actin mRNA levels were determined by RT-PCR analysis; DVL2, active β-catenin and total β-actin protein levels were assessed by immunoblotting. B: NC, DACT3-sh1 and DACT3-sh2 cells were treated as above and apoptosis was determined by PI staining and FACS analysis. The data represent Mean±SD of three independent experiments. , p<0.01. C: SW480 cells transfected with DACT3 SmartPool siRNA (DACT3-SP) and an independent DACT3 siRNA (DACT3-2) were treated as in A. The data represent Mean±SD of three independent experiments. , p<0.05. Apoptosis, DACT3 mRNA levels, DVL2, active β-catenin protein levels, and apoptosis were determined as previously. D: SW480 cells transfected with DACT1 siRNA were untreated or treated with DZNep/TSA, and harvested for mRNA and apoptosis analysis as above. The data represent Mean±SD of three independent experiments.

FIG. 9. Effects of DACT3 overexpression on Dvl2 and β-catenin in colorectal cancer cells. A: Exogenously expressed DACT3 associates with Dvl2. SW480 cells were transiently transfected with the indicated Flag or HA-tagged expression constructs. DACT3 was immunoprecipitated with anti-Flag and the immunoprecipitates were probed with anti-HA antibody. Reciprocal coimmunoprecipitation between DACT3 and Dvl2 is shown on the lower panel. B: Western blot analysis of HA-tagged Dvl2 protein levels in SW480 cells co-transfected with Flag-DACT3 or an empty vector. C: Immunofluorescent images of SW480 cells transfected with Myc-tagged DACT1 or DACT3 expression construct for 72 h. Myc-tagged DACT1 or DACT3 and β-catenin levels were detected by staining with anti-myc (green) and anti-β-catenin (red). Nuclei were stained by DRAQ5 (blue). Arrows indicate transfected cells expressing DACT3-myc. D: Colony formation assay showing ectopic expression of DACT3 suppresses colon cell growth. DLD1 cells were transfected with a DACT3 expression vector or the empty vector, and selected for 12 days with Zeocin. The number of colonies relative to the control in triplicates is shown on the right (error bar: Mean±SD).

FIG. 10. Low molecular weight organic compound inhibition of GSK-3 treatment rescues the downregulation of β-catenin by DZNep/TSA. DLD1 cells were treated as indicated in the presence or absence of GSK-3 inhibitor LY2119301 (5 mM). The cells were then harvested for immunoblotting with indicated antibodies.

Figure 11A:
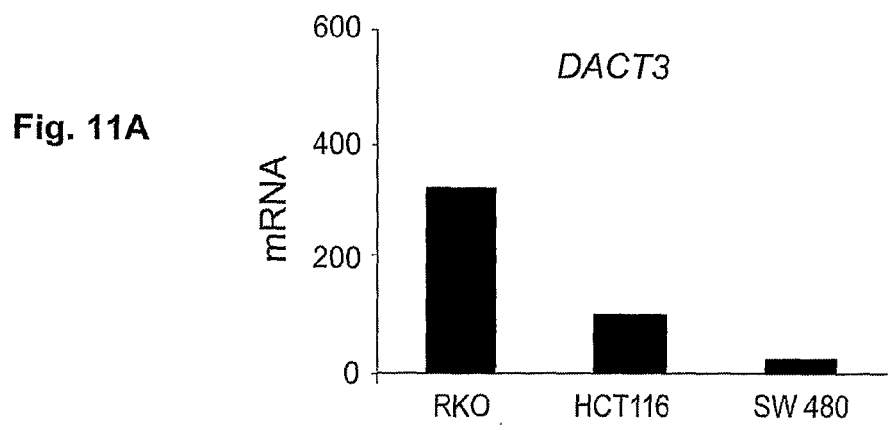
FIG. 11 depicts DACT3 mRNA (A) and protein (B) levels in cancer cell lines.
Figure 11B:
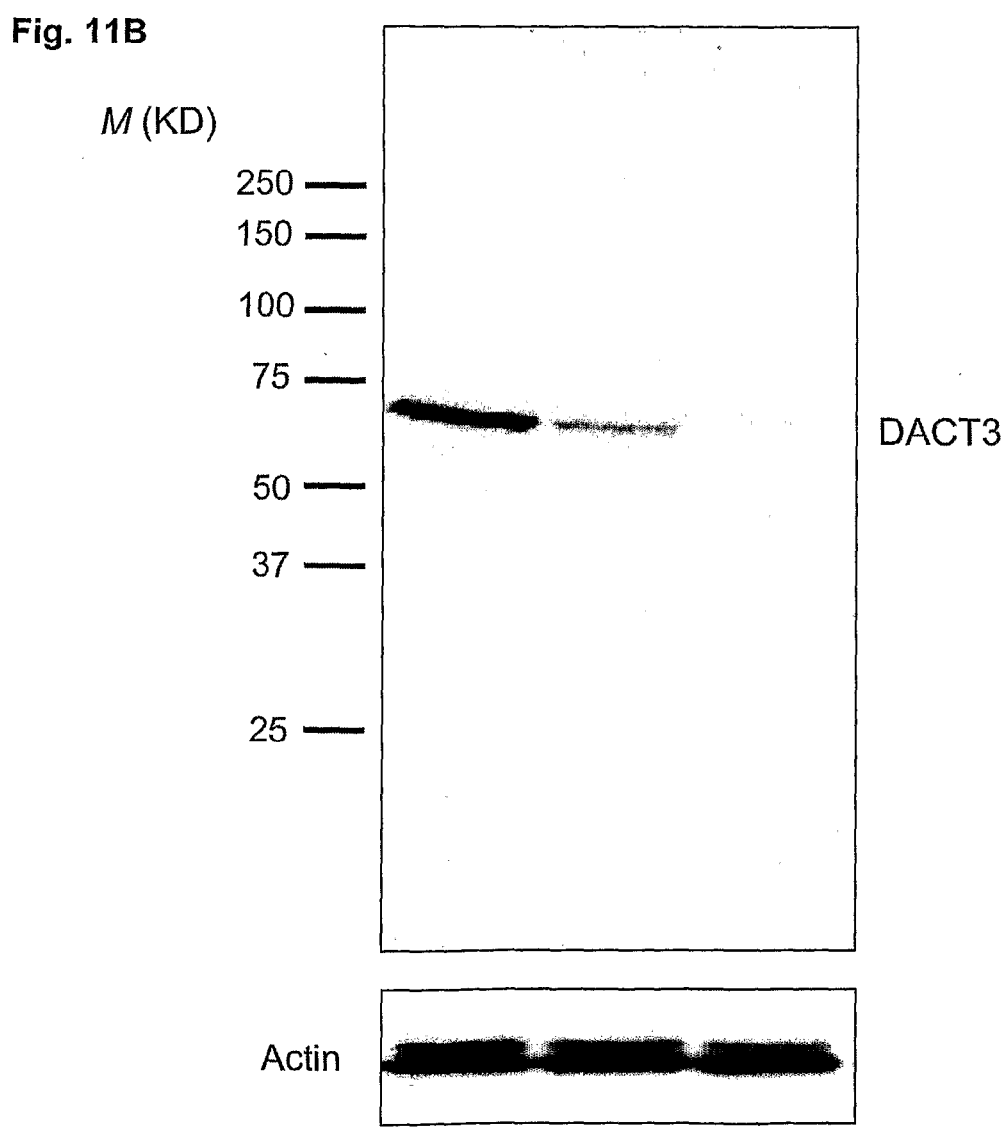

FIG. 11. DACT3 antiserum detects DACT3 of expected size (69 kD). The expression levels of DACT3 mRNA in RKO, HCT116 and SW480 cells are shown in FIG. 11A. FIG. 11B shows the corresponding DACT3 protein levels in these cells, as detected with an antibody raised against a human DACT3 peptide as described in the Examples below.

FIG. 12 lists 81 genes that were found to be reactivated by a combination treatment of DZNep and TSA in DLD1, SW480 and HT29 cells. The increase in expression of all 81 genes by in the three cancer cell lines is depicted by numerical values. Strikingly, induction of DACT3 is the highest by far.

FIG. 13. DZNep also synergies with other HDAC inhibitors to induce apoptosis (A), and induction of DACT3 and inhibition of β-catenin (B). SAHA (2 μM), PXD101 (1 μM) and DZNep (5 μM).

Figure 14A:
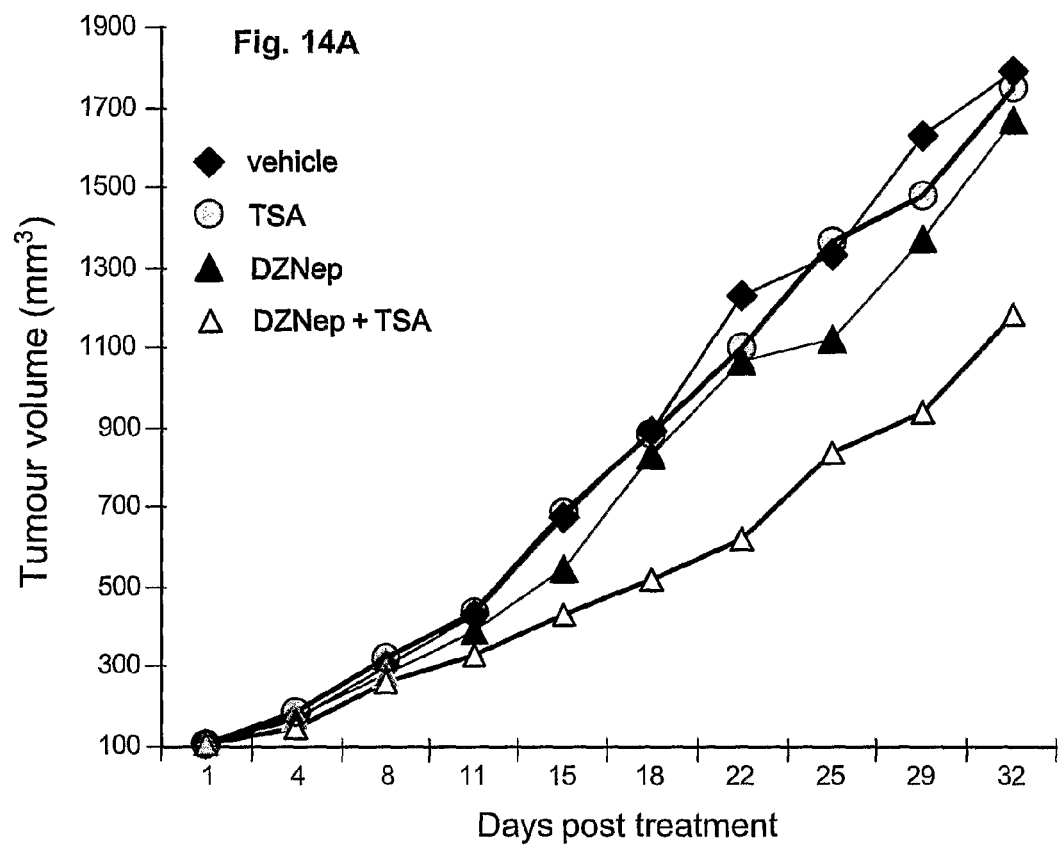
FIG. 14A shows the in vivo effect of DZNep/TSA administration on tumor volume.

FIG. 14A. Colon cancer HT-29 cells xenograft model showing the in vivo effect on animals treated with vehicle, TSA [0.5 mg/kg], DZNep [2 mg/kg] and a combination of DZNep [2 mg/kg] and TSA [0.5 mg/kg].

Figure 14B:
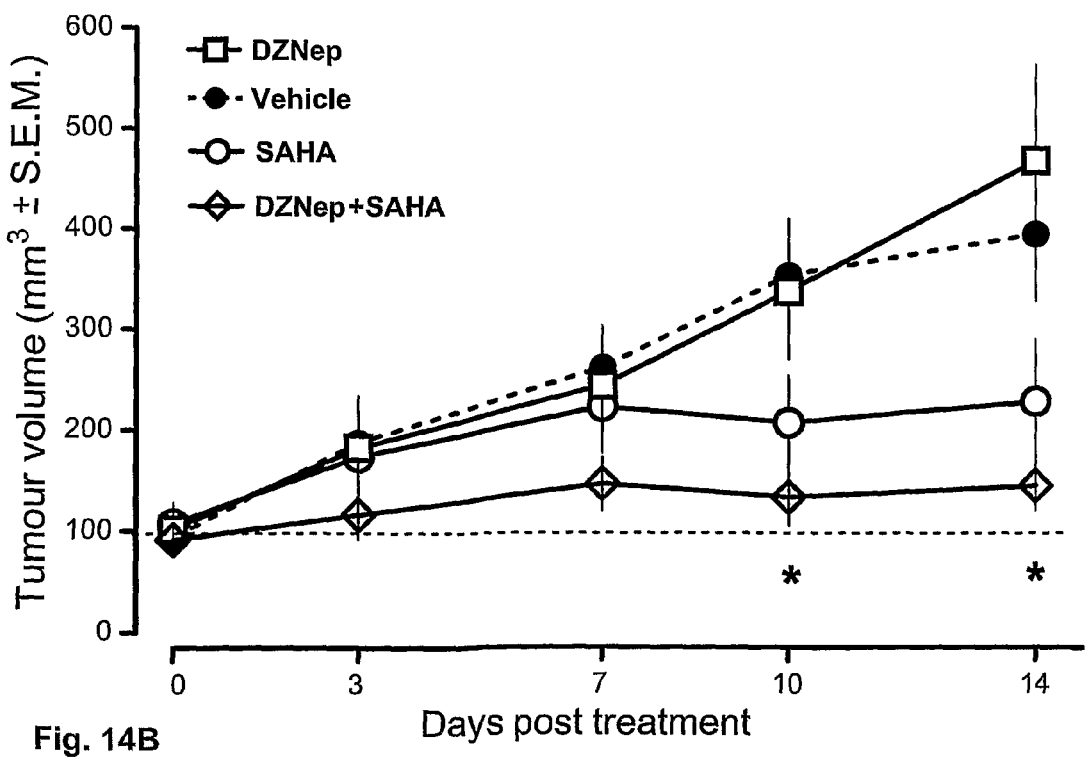
FIG. 14B shows the in vivo effect of a combination of DZNep and a further histone deacetylase inhibitor on tumor volume.

FIG. 14B. Synergistic effect of DZNep and SAHA in HCT116 xenograft tumour growth inhibition. Tumour volumes (SB-030) are depicted. * indicates p<0.05 in One-Way ANOVA/Dunnett compared to vehicle control.

Figure 15:
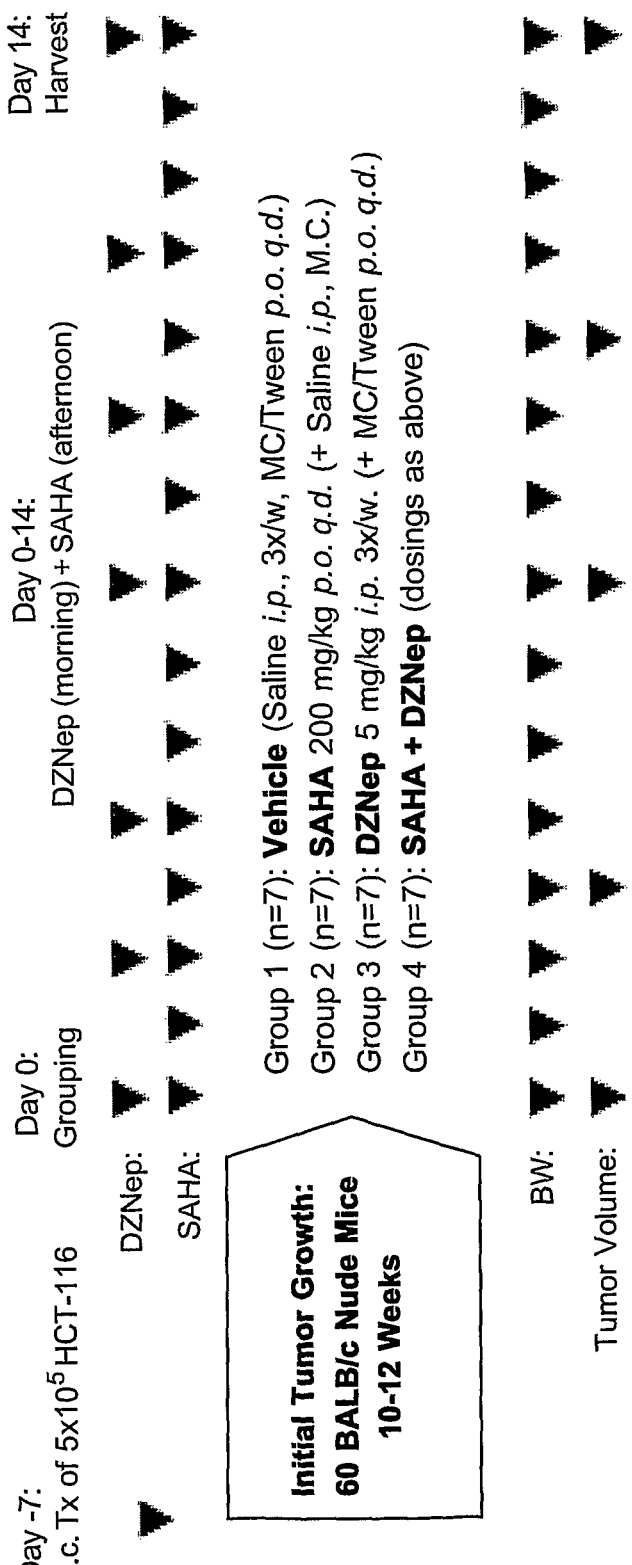
FIG. 15 depicts the protocol design used in obtaining the data of FIG. 14B.

FIG. 15. Protocol design for SB-HCT-116-030, the tumor volume data of which are depicted in FIG. 14B. Tumors were established in female BALB/c nude mice by s.c. implantation of $5 \times 10^6$ HCT-116 cells at day −7, and dosing of animals with DZNep and SAHA in the combinations indicated started at day 0, when animals were randomized according to tumor sizes to achieve homogenous groups (mean tumor volume 91-107 mm$^3$, some mice were not included in the study, as they had either developed no tumors or tumors that were too large/unevenly shaped). Dosing of the four groups with DZNep, SAHA and respective vehicles started at day 0 as indicated (red and blue arrows), and body weights (BW) and tumor volumes were assessed at the days indicated by grey arrows. All treatments were terminated at day 14.

Figure 16:
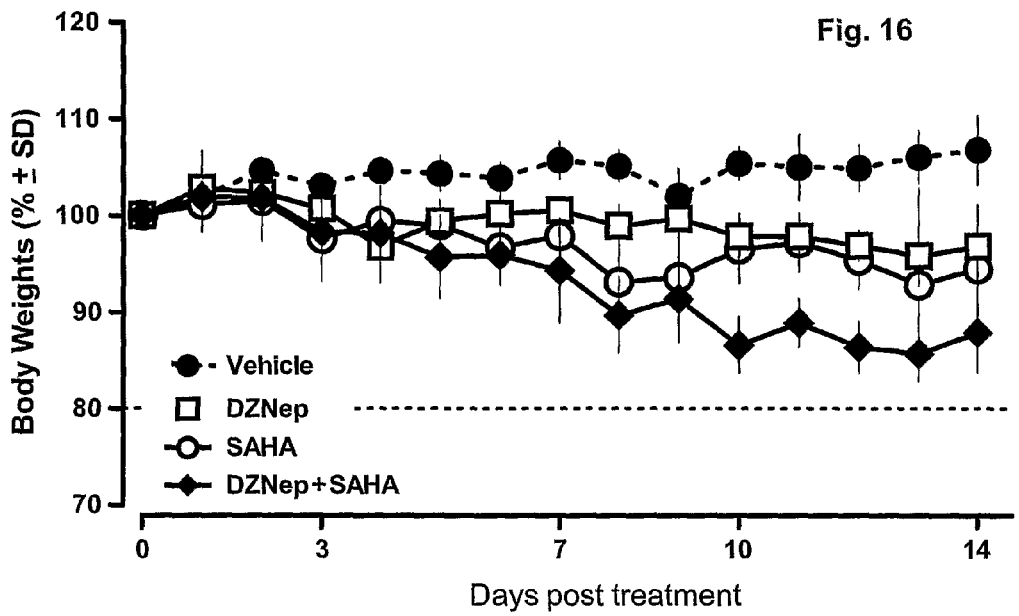
FIG. 16 depicts the body weight changes during HCT116 xenograft tumour growth inhibition with DZNep and SAHA.

FIG. 16. Body Weight Changes during HCT116 xenograft tumour growth inhibition with DZNep and SAHA. Tumors were established in female BALB/c nude mice by s.c. implantation of $5 \times 10^6$ HCT-116 cells at day −7, and dosing of animals with DZNep and SAHA in the combinations indicated started at day 0, when the mean tumor volume was 91-107 mm$^3$. The body weight was maintained at >80% in all groups. There were 1 NTRD (day 4) and 1 TRD (day 10, body weight 82%) recorded in the SAHA group. n=7/group.

Figure 17:
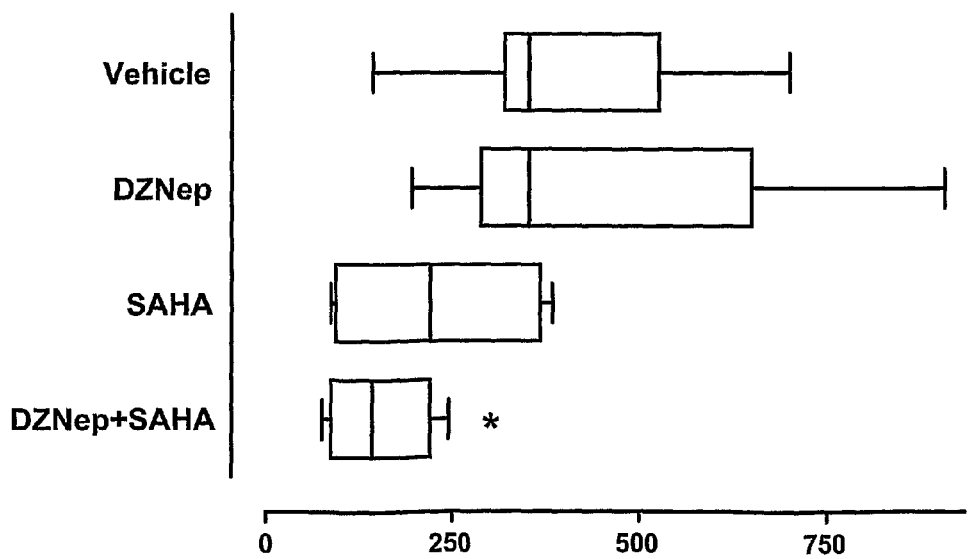
FIG. 17 depicts the tumor volumes during HCT116 xenograft tumour growth inhibition with DZNep and SAHA.

FIG. 17. Tumor Volumes during HCT116 xenograft tumour growth inhibition with DZNep and SAHA. Tumors were established in female BALB/c nude mice by s.c. implantation of $5 \times 10^6$ HCT-116 cells at day −7, and dosing of animals with DZNep and SAHA in the combinations indicated started at day 0, when the mean tumor volume was 91-107 mm$^3$. The tumor burden (volume in mm$^3$) was assessed at day 14 and is shown as median/distribution of tumor volume (Box & Whiskers Diagram). Only the tumor volumes of animals treated with DZNep+SAHA were significantly different compared to the vehicle control group (p<0.01 by one-way ANOVA followed by Dunnett's post test).

FIG. 18. Tumor Growth Inhibition in SB-HCT-116-030 (cf. FIG. 14B to FIG. 17) in percent. Tumors were established in female BALB/c nude mice by s.c. implantation of $5 \times 10^6$ HCT-116 cells at day −7, and dosing of animals with DZNep and SAHA in the combinations indicated started at day 0, when the mean tumor volume was 91-107 mm$^3$. The tumor burden (volume in mm$^3$) was assessed at days 3, 7, 10 and 14, and tumor growth inhibition (TGI) was calculated as outlined below. Shown are both data sets for mean-based as well as median-based calculations. One animal in the SAHA group was lost due to a gavage error at day 4 (NTRD), and a second mouse died with a body weight of 82% in the SAHA group as well (TRD).

EXAMPLES

1. Experimental Procedures 1.1 Samples, Cell Lines and Drug Treatment

Human tissue samples were obtained from Singapore Tissue Network using protocols approved by institutional Review Board of National University of Singapore; informed consent was obtained from each individual who provided the tissues. The colorectal cancer cell lines and non-transformed cell lines used in this study were purchased from the American Type Culture Collection (Manassas, Va.). HCT116 cells with genetic disruption of DNMT1 (DNA methyltransferase 1) and DNMT3B (DNA methyltransferase 3B) (HCT116 DKO) were kindly provided by Dr. Bert Vogelstein (Johns Hopkins University, MD). For drug treatment, cells were seeded the day before the drug treatment. Cells were treated with 5 µM 3-Deazaneplanocin A (DZNep) (obtained from Dr. Victor E. Marquez at National Cancer Institute, USA) or 5 µM 5-aza-2'-deoxycytidine (5-AzaC; Sigma) for 72 hours and Trichostatin A (TSA; Cell Signaling) at 100-200 nM for 24 hours. For 5-AzaC treatment, the medium was replaced with freshly added 5-AzaC for every 24 h. For co-treatment of cells with DZNep and TSA, DZNep was added for 24 hours followed by TSA for additional 24 hours for gene expression analysis and 48 hours for FACS analysis.

1.2 Mice and Husbandry

Female athymic BALB/c nude mice (Harlan, UK, 10-12 weeks of age) were housed in the Biological Resource Centre, Biopolis (BRC) in individual ventilated cages under controlled conditions (12-hour light cycle, 21-22° C., 40-60% humidity, ad libitum access to sterilized tap water and irradiated standard rodent diet consisting of 19% protein/5% fat/5% fiber) in compliance with the National Institutes of Health (NIH) and National Advisory Committee for Laboratory Animal Research (NACLAR) guidelines. Animal care approval was obtained from the Biopolis Institutional Animal Care and Use Committee (Biopolis IACUC approval #050076).

1.3 Mapping of DACT3 Transcription Start Sites and Cloning of Full-Length DACT3 cDNA 10 µg of total RNA was isolated from HEK293 cells with RNeasy Mini Kit (Qiagen). DACT3 transcription start sites were mapped by RNA ligation mediated 5'RACE using FirstChoice RLM-RACE kit (Ambion) according to the manufacturer's protocol with the exception of reverse transcription and PCR steps. Reverse transcription after linker ligation was carried out at 64° C. for 1 h using Thermo-X polymerase (Invitrogen) and a gene specific oligo: 5-GAC-CCAGGCGACCATAGGAGCTGGATC-3' (SEQ ID NO: 1). Nested PCR was carried out using PfuUltraPhusion polymerase (Stratagene) with forward primers provided by the FirstChoice RLM-RACE kit and gene specific reverse primers: 5'-GCTGGATCCAGAGA AGCCACTGTCCCCA-3' (SEQ ID NO: 2) and 5'-CACAGAAGGTTGAGGGTGGT-GAAT CTGGACCT-3' (SEQ ID NO: 3). PCR products were cloned into pCR-BluntII-TOPO vector (Invitrogen) and sequenced with M13 primers. A tagged DACT3 expression construct containing the longest open reading frame, based on mRNA start site mapping was generated for overexpression studies. Full-length DACT3 coding region was amplified by RT-PCR using 5 µg of total mRNA from HEK293 cells and following primers: 5'-ATTGAATTCAATGATC CGGGC-CTTCTCGTTCCCGGT-3' (SEQ ID NO: 4) and 5'-ATTA-GATCTTCACACTGTA GTCATGACCTTGAGAGAAC-CCGA-3' (SEQ ID NO: 5). The PCR product was cloned into p3×FLAG-CMV10 between EcoRI and BglII sites and sequenced.

1.4 RNA Interference

The SMARTpool® siRNA targeting DACT3 and the non-targeting control were purchased from Dharmacon (Lafayett, Colo.). A separate DACT3 siRNA targeting the following sequence: 5'-GGUUCUCUCAAGGUCAUGA-3' (SEQ ID NO: 6) was obtained from Sigma-Proligo. To generate DACT3 small hairpin RNA (shRNA) stable cells, a DACT3 siRNA sequence (GGAGAAUCGCCUGCCUUCA) (SEQ ID NO: 7) was cloned into the pSIREN-RetroQ retroviral expression vector. The pSIREN-RetroQ-Neg Vector was used as negative control shRNA (BD Bioscience) and cells were selected and expanded as described (Tan, J., et al., *Genes Dev* (2007) 21, 1050-1063).

1.5 Immunoblot Analysis

Immunoblotting was performed as described previously (Tan et al., 2007, supra). The blots were probed with the following antibodies: anti-H3K27me3 (07-449), anti-H3K9me3 (07-442), anti-H3K9/K14 ac (06-599), anti-H3K4me3 (07-473) and anti-active β-catenin(05-665), were purchased from Upstate. Anti-H4K20me3 (ab9053) was from Abcam. Anti-β-catenin (6B3) and anti-H3 (3H1) were from Cell Signaling and anti-DVL2 (sc-8026) was from Santa Cruz. The rabbit polyclonal antibody to DACT3 was raised against a 14 amino acid peptide from human DACT3 (LSLESGGLEQESGR, (SEQ ID NO: 8) and was purified through affinity column.

1.6 Transfection and Immunoprecipitation

SW480 cells were transiently transfected using Fugen 6.0 (Roche). At 48 h post-transfection, the cells were lysed with 1 ml of lysis buffer (20 mM Tris-HCl, pH 7.4, 2 mM EDTA, 25 mM NaF, 1% Triton X-100) plus protease inhibitors (Roche) for 30 min at 4° C. After 12,000 g centrifugation for 30 min, the lysates were immunoprecipitated with anti-FLAG M2 agarose affinity gel (Sigma) or anti-HA affinity matrix (Roche) for overnight at 4° C. The precipitants were washed three times with washing buffer (50 mM Tris-HCl, pH 8.0, 150 mM NaCl, 1% Nonidet P-40, 0.5% sodium deoxycholate, and 0.1% SDS) and the immune complexes eluted with sample buffer containing 1 SDS for 5 min at 95° C. and analyzed by SDS-PAGE. Immunoblotting was performed with primary antibodies against HA tag (sc-805, Santa Cruz) or FLAG tag (F1804, Sigma).

1.7 Apoptosis and Flow Cytometric Analysis

Cells were harvested and fixed in 70% ethanol. Fixed cells were stained with propidium iodide (50 µg/mL) after treatment with RNase (100 µg/mL). The stained cells were analyzed for DNA content by fluorescence-activated cell sorting (FACS) in a FACSCalibur (Becton Dickinson Instrument, San Jose, Calif.). Apoptotic sub-G1 fraction was quantified using the CellQuest software (Becton Dickinson). To measure the mitochondrial transmembrane potential (MTP), cells were stained with JC-1, according to the manufacturer's instructions (BD Bioscience), and cells positive for JC-1 detection were measured using CellQuest software (BD Bioscience). To measure caspase-3 activity, cells were fixed with Cytofix/Cytoperm solution (BD Biosciences) as instructed and then stained with fluorescein isothiocyanate-conjugated rabbit anti-active caspase-3 monoclonal antibody (BD Biosciences). Quantification of cells positive for the caspase-3 detection was performed by flow cytometry.

1.8 Microarray Gene Expression Analysis and Semi-Quantitative RT-PCR

Total RNA was isolated using Trizol (Invitrogen) and purified with the RNeasy Mini Kit (Qiagen). Reverse transcription was performed using an RNA Amplification kit (Ambion). The microarray hybridization was performed using the Illumina Gene Expression Sentrix®BeadChip HumanRef-8_V2 and data analysis was performed using GeneSpring software from Agilent Technologies as described (Tan et al., 2007, supra). For RT-PCR, total RNA was reverse-transcribed using oligo(dT)12-18 primer with Superscript II reverse transcriptase (Invitrogen). 100 ng of cDNA was used for PCR and the Primer sequences were as follows:

```
DACT3 forward:
5'-CTCCCCAGCGTCGTCTGCTTTA-3'      (SEQ ID NO: 9)

DACT3 reverse:
5'-ATTCGCTCTCCCCGTAACCC-3'        (SEQ ID NO: 10)

DACT2 forward:
5'-CCTGCACGCCGTGGCTCTAC-3'        (SEQ ID NO: 11)

DACT2 reverse:
5'-CCCTGTTCTCCCTCGCTACCCTT-3'     (SEQ ID NO: 12)

DACT1 forward:
5'-CAGTCGCCTGGAGGAGAAGT-3'        (SEQ ID NO: 13)

DACT1 reverse:
5'-CTGCTTGTCAAGCTCTTGCA-3'        (SEQ ID NO: 14)

DKK1 forward:
5'-AGGCGTGCAAATCTGTCTCG-3'        (SEQ ID NO: 15)

DKK1 reverse:
5'-TGCATTTGGATAGCTGGTTTAGTG-3'    (SEQ ID NO: 16)

DKK2 forward1:
5'-CGCGTTGATGCGGAGCAAGGAT-3'      (SEQ ID NO: 17)

DKK2 reverse:
5'-TTATTGCAGCGGGTACTGGGGCAG-3'    (SEQ ID NO: 18)

DKK3 forward:
5'-AGGAGGCCACCCTCAATGAG-3'        (SEQ ID NO: 19)

DKK3 reverse:
5'-CAGCTTCTTCTGCCTCCATC-3'        (SEQ ID NO: 20)

SFRP1 forward:
5'-TCGGCCGCGAGTACGACTA-3'         (SEQ ID NO: 21)

SFRP1 reverse:
5'-TCTTGTAGCCCACGTTGTGG-3'        (SEQ ID NO: 22)

MYC forward:
5'-CTGGATTTTTTTCGGGTAGTGG-3'      (SEQ ID NO: 23)

MYC reverse:
5'-TCGCAGTAGAAATACGGCTG-3'        (SEQ ID NO: 24)

CCND1 forward:
5'-ATGGAACACCAGCTCCTGTG-3'        (SEQ ID NO: 25)

CCND1 reverse:
5'-TTGAAGTAGGACACCGAGGG-3'        (SEQ ID NO: 26)

GAPDH forward:
5'-CAAAGTTGTCATGGATGACC-3'        (SEQ ID NO: 27)

GAPDH reverse:
5'-CCATGGAGAAGGCTGGGG-3'          (SEQ ID NO: 28)

Actin forward:
5'-GTGGGGCGCCCCAGGCACCA-3'        (SEQ ID NO: 29)

Actin reverse:
5'-CTCCTTAATGTCACGCACGATTTC-3'    (SEQ ID NO: 30)
```

1.9 DNA Methylation Analysis

The CpG island DNA methylation status was determined by PCR analysis after bisulfited modification and followed by methylation-specific PCR (MSP) and bisulfite genomic sequencing (BGS) (Yoshikawa, H., et al., *Nat Genet* (2001) 28, 29-35). All bisulfite genomic sequencing and methylation-specific PCR primers were designed to be close transcription start sites and in the CpG islands of the genes investigated. Primer sequences were as follows:

```
MSP:
DACT1 M forward:
5'-TAGTTTTAGCGTTTTGTTTTTTCGT-3'   (SEQ ID NO: 31)

DACT1 M reverse:
5'-TACCGCTCGATATCTACCTCG-3'       (SEQ ID NO: 32)

DACT1 U forward:
5'-TAGTTTTAGTGTTTTGTTTTTTGT-3'    (SEQ ID NO: 33)

DACT1 U reverse:
5'-CTACCACTCAATATCTACCTCACC-3'    (SEQ ID NO: 34)

DACT2 M forward:
5'-TAGGAGGATTCGCGATATAGTTC-3'     (SEQ ID NO: 35)

DACT2 M reverse:
5'-TACAACTCCTACAACCCCGC-3'        (SEQ ID NO: 36)

DACT2 U forward:
5'-TAGGAGGATTTGTGATATAGTTTGG-3'   (SEQ ID NO: 37)

DACT2 U reverse:
5'-CCTACAACTCCTACAACCCCAC-3'      (SEQ ID NO: 38)

DACT3-1 M forward:
5'-AATTTTATCGGAGGACGTTC-3'        (SEQ ID NO: 39)

DACT3-1 M reverse:
5'-CTTACGAACGAACGCTAACTAC-3'      (SEQ ID NO: 40)

DACT3-1 U forward:
5'-AATAATTTTATTGGAGGATGTTT-3'     (SEQ ID NO: 41)

DACT3-1 U reverse:
5'-CTTACAAACAAACACTAACTACCAT-3'   (SEQ ID NO: 42)

DACT3-2 M forward:
5'-AGTTTTCGTTAGGAAGTTTATTCGT-3'   (SEQ ID NO: 43)

DACT3-2 M reverse:
5'-TATCACCGTCTCATCTACATAAACG-3'   (SEQ ID NO: 44)

DACT3-2 U forward:
5'-AGTTTTTGTTAGGAAGTTTATTTGT-3'   (SEQ ID NO: 45)

DACT3-2 U reverse:
5'-ATCACCATCTCATCTACATAAACACC-3'  (SEQ ID NO: 46)

DACT3-3 M forward:
5'-GATAGTTCGGTTAGCGGGC-3'         (SEQ ID NO: 47)

DACT3-3 M reverse:
5'-AACGCCTACTACACGCGATA-3'        (SEQ ID NO: 48)

DACT3-3 U forward:
5'-GGTGATAGTTTGGTTAGTGGGT-3'      (SEQ ID NO: 49)

DACT3-3 U reverse:
5'-AACACCTACTACACACAATACTC-3'     (SEQ ID NO: 50)

DACT3-4 M forward:
5'-TTCGTTTGTGTTTGTTTGTTTC-3'      (SEQ ID NO: 51)

DACT3-4 M reverse:
5'-ACCCGATCTCGAATTTAACA-3'        (SEQ ID NO: 52)
```

```
DACT3-4 U forward:
5'-ATTTTTGTTTGTGTTTGTTTGTTTT-3'    (SEQ ID NO: 53)

DACT3-4 U reverse:
5'-TACCCAATCTCAAATTTAACACA-3'      (SEQ ID NO: 54)

SFRP1 M forward:
5'-CGCGTTTGGTTTTAGTAAATC -3'       (SEQ ID NO: 55)

SFRP1 M reverse:
5'-CCGAAAATACGACGAACA-3'           (SEQ ID NO: 56)

SFRP1 U forward:
5'-AGTTGTGTTTGGTTTTAGTAAATT-3'     (SEQ ID NO: 57)

SFRP1 U reverse:
5'-CTCCCAAAAATACAACAAACA-3'        (SEQ ID NO: 58)

BGS:
DACT1 BGS forward:
5'-ATTGGGGGTTATGAAGTYG-3'          (SEQ ID NO: 59)

DACT1 BGS reverse:
5'-TCCAAAAACTTCTCCTCCAAAC-3'       (SEQ ID NO: 60)

DACT2 BGS forward:
5'-TGGTTATAGATTTTAGTTTATTTTGG-3'   (SEQ ID NO: 61)

DACT2 BGS reverse:
5'-CAACCCCTACAACTCCTACAAC-3'       (SEQ ID NO: 62)

DACT3 BGS forward:
5'-AAGAGGGTGGAATTTGTTGTA-3'        (SEQ ID NO: 63)

DACT3 BGS reverse:
5'-TCACCRTCTCATCTACATAAAC-3'       (SEQ ID NO: 64)
```

1.10 Chromatin Immunoprecipitation (ChIP) Assays

ChIP assays were performed as described previously (Zhao et al., 2005, supra). The immunoprecipitated DNA was quantitated by real-time quantitative PCR using the PRISM 7900 Sequence Detection System (Applied Biosystems). Primer sets were chosen to amplify approximately 100-150 bp around the indicated region. The following antibodies were used in the ChIP study: anti-H3K27me3 (Upstate), anti-H3K9me3 and anti-H3K9me2 (Abcam), anti-H3K20me3 (Upstate), anti-H3K9/K14ac and anti-H3K4me3 (Upstate). The enrichments of these histone marks at the examined regions were quantitated relative to the input amount. To compare the two pools of DNA materials, from cells untreated and from cells treated, a further normalization of the ΔCt values against a region that shows low background enrichment was performed. The sequences of the PCR primers were as follows:

```
DACT1 C forward 1:
5'-GTGCAACTGATGCCCCTTAC-3'         (SEQ ID NO: 65)

DACT1 C reverse 1:
5'-TTGTCCAGCGGTGAACATTC-3'         (SEQ ID NO: 66)

DACT1 C forward 2:
5'-GCTTGTCTGCCTGACTTAAG-3'         (SEQ ID NO: 67)

DACT1 C reverse 2:
5'-TGGCCTGTGTTATGTCACAC-3'         (SEQ ID NO: 68)

DACT1 C forward 3:
5'-TGTGCTAGCCACGTTGTAAG-3'         (SEQ ID NO: 69)

DACT1 C reverse 3:
5'-GCTATGGGAACCTGCTGTTG-3'         (SEQ ID NO: 70)

DACT1 C forward 4:
5'-GACGAGAAAGAGCCAATGAG-3'         (SEQ ID NO: 71)

DACT1 C reverse 4:
5'-CCTTTTCGGGTTTACTGCAC-3'         (SEQ ID NO: 72)

DACT1 C forward 5:
5'-CTTGGAGGAGAACATCTTGC-3'         (SEQ ID NO: 73)

DACT1 C reverse 5:
5'-TTCGGGCACGACCTACCAAT-3'         (SEQ ID NO: 74)

DACT1 C forward 6:
5'-TCGCCTAGTTCTAACGTTCG-3'         (SEQ ID NO: 75)

DACT1 C reverse 6:
5'-CGGGAGGAGATAAAGTCAAG-3'         (SEQ ID NO: 76)

DACT1 C forward 7:
5'-TCTGCCAGCTGTGATTGGTG-3'         (SEQ ID NO: 77)

DACT1 C reverse 7:
5'-ACTGAGACACTGACAGAAAC-3'         (SEQ ID NO: 78)

DACT1 C forward 8:
5'-GAGGCGTTCAAATCTCGATG-3'         (SEQ ID NO: 79)

DACT1 C reverse 8:
5'-CCAGTGCCAAGTATAATGTG-3'         (SEQ ID NO: 80)

DACT1 C forward 9:
5'-GTAAGTCAGAACTGGGCTAG-3'         (SEQ ID NO: 81)

DACT1 C reverse 9:
5'-AATCTAAGGAGCCCAAATGG-3'         (SEQ ID NO: 82)

DACT1 C forward 10:
5'-AACTCGGTGTTCAGTGAGTG-3'         (SEQ ID NO: 83)

DACT1 C reverse 10:
5'-GGCAACCATCTGAGAGACTC-3'         (SEQ ID NO: 84)

DACT2 C forward 1:
5'-GCTGACGTCATACTTAACAG-3'         (SEQ ID NO: 85)

DACT2 C reverse 1:
5'-CCAGGATGGGTACCTTTTAC-3'         (SEQ ID NO: 86)

DACT2 C forward 2:
5'-AAGATGCTCAACGTCCTTAG-3'         (SEQ ID NO: 87)

DACT2 C reverse 2:
5'-CAGATGTGAAGTGGTATCTC-3'         (SEQ ID NO: 88)

DACT2 C forward 3:
5'-GAGGTGCGGTTTCCAAACTG-3'         (SEQ ID NO: 89)

DACT2 C reverse 3:
5'-ATTGCAAGGACCGTGTTACC-3'         (SEQ ID NO: 90)

DACT2 C forward 4:
5'-CAAGCCTTTCTCCGCCTTTG-3'         (SEQ ID NO: 91)

DACT2 C reverse 4:
5'-GAGCGCCTCCGTGACTTCAG-3'         (SEQ ID NO: 92)

DACT2 C forward 5:
5'-CAGCCCACCTTGGCGACCTG-3'         (SEQ ID NO: 93)

DACT2 C reverse 5:
5'-GCGGATCCCGAGCTGTGTCG-3'         (SEQ ID NO: 94)

DACT2 C forward 6:
5'-CCGACTTGTCCTCAGGAATG-3'         (SEQ ID NO: 95)

DACT2 C reverse 6:
5'-CTCCTTACAGGTCAGGTCAC-3'         (SEQ ID NO: 96)

DACT2 C forward 7:
5'-GACTGTGTGGGATTAACCTG-3'         (SEQ ID NO: 97)
```

-continued

```
DACT2 C reverse 7:
5'-CTTTCCTCTCAGGAGGCATC-3'      (SEQ ID NO: 98)

DACT2 C forward 8:
5'-GCTGCTGAGATGCTGTTGTG-3'      (SEQ ID NO: 99)

DACT2 C reverse 8:
5'-ACAGAACAGTTGAAGCCAGC-3'      (SEQ ID NO: 100)

DACT3 C forward 1:
5'-CTCAGATGGGATGGACCCTA-3'      (SEQ ID NO: 101)

DACT3 C reverse 1:
5'-ATTCCCATTCAGCACAGGTC-3'      (SEQ ID NO: 102)

DACT3 C forward 2:
5'-CTTCACTCGCACCACCAAAG-3'      (SEQ ID NO: 103)

DACT3 C reverse 2:
5'-CCTTTGAGGAAGGCGTGTAG-3'      (SEQ ID NO: 104)

DACT3 C forward 3:
5'-GTGTCTGGGAAGGCTTCTTG-3'      (SEQ ID NO: 105)

DACT3 C reverse 3:
5'-CCCAACCTTCAGCTTCTGAG-3'      (SEQ ID NO: 106)

DACT3 C forward 4:
5'-AGGCACAGACCAATGGCATT-3'      (SEQ ID NO: 107)

DACT3 C reverse 4:
5'-CCACGCGTCACAATGAAACA-3'      (SEQ ID NO: 108)

DACT3 C forward 5:
5'-TTGCGAGCATGCGTCGTGTT-3'      (SEQ ID NO: 109)

DACT3 C reverse 5:
5'-CGAGCAACAGCCGCCTATTG-3'      (SEQ ID NO: 110)

DACT3 C forward 6:
5'-TGTCTGTCTGTCTCGGTTGG-3'      (SEQ ID NO: 111)

DACT3 C reverse 6:
5'-ACCCCTGTCCTTTCTCACT-3'       (SEQ ID NO: 112)

DACT3 C forward 7:
5'-TTCCCTAAGTCCTGGTGTGC-3'      (SEQ ID NO: 113)

DACT3 C reverse 7:
5'-TCCTCAGGGACTGTGAGCTT-3'      (SEQ ID NO: 114)

DACT3 C forward 8:
5'-CTGGACTCTGGGTGTTCTCA-3'      (SEQ ID NO: 115)

DACT3 C reverse 8:
5'-CGGGAGACTCAAGGAATGAC-3'      (SEQ ID NO: 116)

DACT3 C forward 9:
5'-CAGTCTCTAGGCAAAGCTTG-3'      (SEQ ID NO: 117)

DACT3 C reverse 9:
5'-GCCCTAATCCACTCTTCAGA-3'      (SEQ ID NO: 118)

DACT3 C forward 10:
5'-GGAATTAGACTTGGCAGAAC-3'      (SEQ ID NO: 119)

DACT3 C reverse 10:
5'-CTTCAGCCTGAGAGACTTTG-3'      (SEQ ID NO: 120)

DACT3 C forward 11:
5'-GTGAGGTCCCAGAGACTATG-3'      (SEQ ID NO: 121)

DACT3 C reverse 11:
5'-TGATTACAGCCTGCAGTCAC-3'      (SEQ ID NO: 122)
```

1.11 Immunofluorescence Staining and Confocal Microscopy

The cells were seeded in 4-well or 8-well culture chamber slides. After treatment or transfection for 72 h, cells were fixed with 3.7% paraformaldehyde in PBS and permeabilized with 0.2% Triton-X100. Cells were sequentially incubated with primary antibodies (anti-Myc or anti-β-catenin) and Alexa Fluor 488 or Alexa Fluor 546-conjugated secondary antibodies (Invitrogen) for 1 hour each and mounted in Fluorsave (Merck) mounting medium. DRAQ5 (Biostats, UK) was diluted in mounting medium for nuclear staining. The stained cells were examined by Zeiss LSM510 confocal microscopy.

1.12 Colony Formation Assay

Colony formation assays were performed as described previously to evaluate tumor cell growth in vitro (Yoshikawa et al., 2001, supra). DLD1 cells were plated at a density of $30 \times 10^4$ per well using 6-well plates, and transfected with either pcDNA4.0-DACT3 or backbone pcDNA4.0 (2.0 µg) using Fugen 6 (Roche) according to the manufacturer's protocol. The cells were replated in triplicates and cultured for 10-15 days in complete DMEM medium containing Zeocin (100 µg/ml). The surviving colonies were stained with Gentian Violet after methanol fixation and visible colonies (×50 cells) were counted.

1.13 Tumor Implantation in Mice

Mice were implanted subcutaneously in the right flank with $5 \times 10^6$ HCT-116 human colon carcinoma cells in a volume of 50 µl using a G23 needle. Tumor growth was monitored twice per week. After 7 days, animals were distributed into various treatment groups such that a mean tumor volume of 91-107 mm³ was achieved in each of the three groups. The tumor volumes were calculated using the formula: Tumor volume $(mm^3)=(w^2 \times l)/2$ (w=width and l=length in mm of the HCT-116 carcinoma).

1.14 Drugs Used in Mice

DZNep was provided by Genome Institute Singapore (GIS, vial #11), and dissolved in saline. For DZNep dosing, every mouse received a volume of 10 ml per kilogram body weight of DZNep appropriately dissolved in Saline (concentration of 0.5 mg/ml for the 5 mg/kg dose etc.). SAHA lot 8 was used, manufactured at S*BIO, and dissolved it in MC/Tween (concentration of 20 mg/ml for 200 mg/kg dosing).

1.15 Treatment Schedules

For the initial MTD study, BALB/c nude mice were randomly assigned into 4 groups of 3 animals each. DZNep was administered on day 0 i.p. at doses of 2.5, 5, 10, and 15 mg/kg, 3× per week. This MTD study was terminated on Day 5.

For the HCT-116 study, nude mice that had received HCT-116 xenografts at day −7 were assigned into 4 groups of 7 animals each, and drug treatment was initiated on day 0 (see FIG. 1 for protocol outline): Group 1—vehicle control for both used compounds (Saline i.p. 3×/week in the morning, MC/Tween p.o. q.d. in the afternoon); Group 2—SAHA (200 mg/kg q.d. p.o. in the afternoon, plus the DZNep vehicle Saline 3/week i.p. in the morning); Group 3—DZNep (5 mg/kg i.p. in the morning, plus the SAHA vehicle MC/Tween p.o. q.d. in the afternoon): Group 4—DZNep plus SAHA (5 mg/kg DZNep i.p. in the morning, plus 200 mg/kg q.d. p.o. in the afternoon). The study was terminated on Day +14.

1.16 Efficacy Evaluation

The efficacy of DZNep treatment was assessed by the tumor growth inhibition (TGI) method, in which treatment-effected decreases in tumor volume of various treatment groups were compared to the vehicle group. The tumor growth inhibition was calculated using the formula:

$$\% \text{TGI} = (V Con_{day\,x} - VTr_{day\,x})/(V Con_{day\,x} - V Con_{day\,0}) \times 100$$

(% TGI=percent tumor growth inhibition, $VCon_{day\,x}$=median or mean tumor volume for the control/vehicle group on day x, $VTr_{day\,x}$=median or mean tumor volume for a treatment group on day x, $VCon_{day\,0}$=median or mean tumor volume for the control/vehicle group on day 0=beginning of the study).

1.17 Toxicity

Animals were weighed daily, and examined frequently for clinical signs of any adverse, drug-related side effects, including activity (inactivity/hyperactivity), skin hydration/dehydration, posture (for example hunched), gait, seizure when put on weighing scale, body temperature (for example, cool to touch) and vocalization. Acceptable toxicity for cancer drugs in mice is defined by the NCI as mean group body weight loss less than 20% during the test, and no more than one toxic death among ten treated animals. Treatment of a group was stopped if more than 1 animal treatment-related death (TRD) was found in the group, or when the body weight of the treatment group dropped below 80% of the day 0 body weight.

1.18 Statistics on In Vivo Data

One-way ANOVA (analysis of variance) followed by the Dunnett's post test was used to determine statistical significances of median tumor volumes. A p value of <0.05 is indicated by *. The software GraphPad Prism (version 4) was used for all statistical analyses and graphic presentations.

2. Results

2.1 DACT3 Expression is Repressed in Colorectal Cancer Independently of Promoter Methylation As noted above, an almost ideal model for studying the Wnt/β-catenin signaling pathway, pathogenic alterations thereof and for intervention therein is colorectal cancer. Those skilled in the art will thus appreciate that results obtained with this model can easily be transferred to any other disorder related to aberrant Wnt/β-catenin signalling. Accordingly, the present examples are based on this model.

Figure 3B:
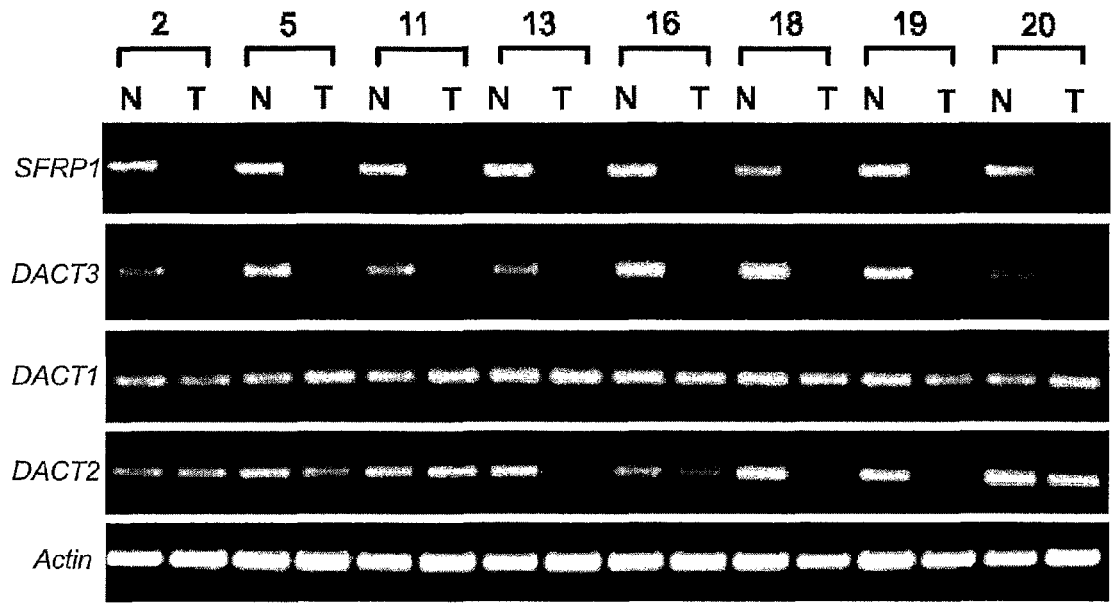
FIG. 3 compares DACT3 expression and DNA methylation in colon cancer. A: Hierarchical clustering of Wnt inhibitors (upper) and Wnt/β-catenin target genes (lower) in tumors (T) vs. normal mucosa (N). B: RT-PCR analysis of SFRP1 and DACT genes from tumor and mucosa samples. C: Methylation status of SFRP1 and DACT3 in tumors. D: RT-PCR analysis of SFRP1 and DACT genes in cancer cell lines vs. normal tissue. E: Methylation status of SFRP1 and DACT genes in cancer cell lines. F: Methylation status of CpG sites in DNA of non-cancerous and cancer cell lines. G: Methylation specific PCR of DACT gene promoters in cancer cells without and with 5-AzaC and in cells deficient of DNA methyltransferases 1 and 3b. H: RT-PCR analysis of SFRP1 and DACT genes in cancer cells treated with 5-AzaC.

To characterize epigenetic effectors of Wnt/β-catenin signaling in colorectal cancer, the inventors initially focused on 14 representative Wnt signaling inhibitors, including members of the SFRP, WIF1, DKK, and DACT gene families, some of which have previously been shown to be transcriptionally inactivated or repressed in various human cancers (He et al.; 2005, supra; Aguilera et al., 2006, supra; He et al., 2005, supra; Suzuki et al., 2002, supra; Suzuki et al., 2004, supra). They determined gene expression in 24 human colorectal tumours versus matched normal mucosa, using the Illumina Human Ref-8_V2 Sentrix® BeadChip (cf. FIG. 3A). It was found that expression of SFRP family members was significantly reduced in nearly all human colorectal tumour samples when compared to normal controls (p<0.001), a finding consistent with a previous report (Suzuki et al., 2004, supra). In contrast, expression of WIF-1 and DKKs in tumor samples did not significantly differ from controls, despite previously reported WIF-1 and DKK1 silencing in established colorectal cancer cell lines (Aguilera et al., 2006, supra; He et al., 2005, supra). Interestingly, expression of DACT3 was reduced in all 24 tumour samples (p<0.001), whereas expression levels of DACT1 and DACT2 did not show significant differences between tumour and control tissues (p=0.24 and p=0.64, respectively). Consistent with reduced expression of Wnt inhibitors leading to enhanced baseline Wnt/β-catenin signal activation, these tumors exhibited increased expression of established β-catenin/TCF target genes, including MYC (He, T. C., et al., *Science* (1998) 281, 1509-1512), the cyclin D1 gene CCND1 (Tetsu, O., & McCormick, F., *Nature* (1999) 398, 422-426), LEF1 (lymphoid enhancer binding factor 1; cf. Filali, M., et al., *J Biol Chem* (2002) 277, 33398-33410) and CD44 (Wielenga, V. J., et al. *Am J Pathol* (1999) 154, 515-523), compared to control tissues. RT-PCR analysis of 8 pairs of randomly-selected patient samples confirmed repression of SFRP1 and DACT3, but not of DACT1 in colorectal cancer compared to controls (FIG. 3B). Notably, reductions in DACT2 expression were also observed in 3 out of 8 tumor samples. Thus, beyond previously-identified reductions in expression of Wnt inhibitors such as the SFRPs, it was found that the expression of DACT3 is also consistently reduced in colorectal cancer. Additionally, evidence was found that in at least some colorectal tumors, DACT2 expression is also reduced.

Figure 3C:
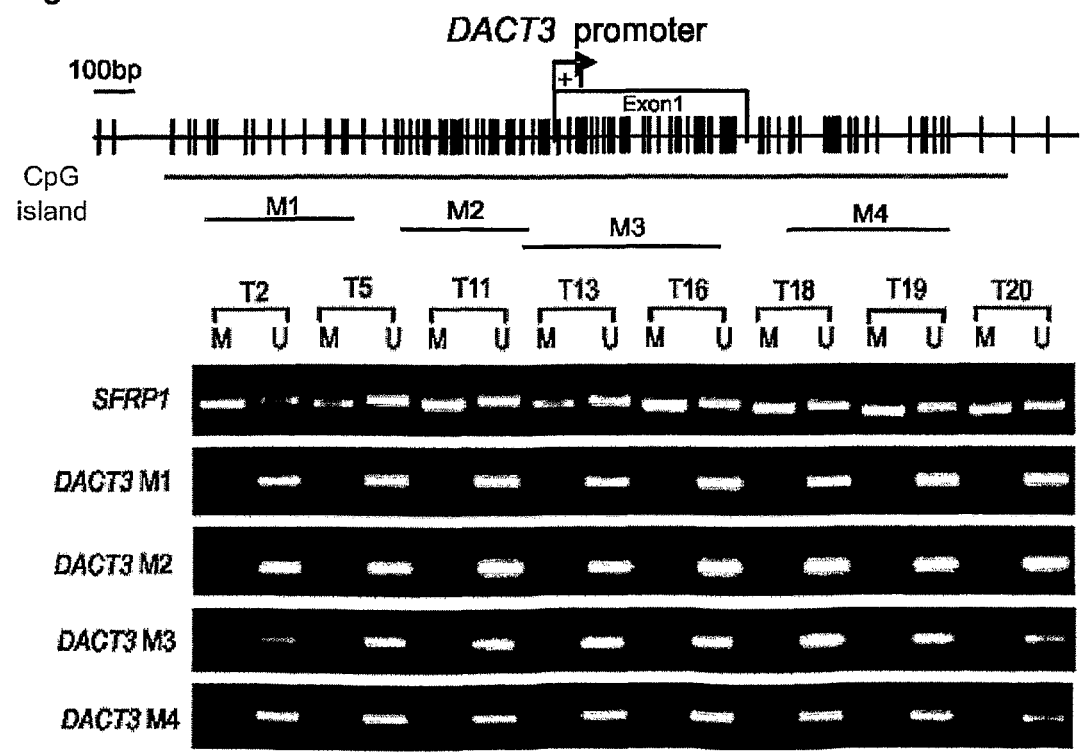

SFRPs have been shown to be transcriptionally inactivated in cancer cells through promoter methylation (Suzuki et al., 2004, supra). To determine the methylation status of the DACT3 promoter, the present inventors performed methylation-specific PCR (MSP) analysis in the 8 colorectal tumor samples around the transcription start site as determined by 5'-RACE (FIG. 2). The DACT3 promoter contains a CpG island (FIG. 3C). MSP analysis covering the entire CpG island indicates a lack of DNA methylation at the DACT3 promoter in colorectal tumor samples (FIG. 3C). As a positive control, using the same technique it was confirmed that the promoter region of SFRP1 is methylated in these same tumor samples (FIG. 3C). This finding suggests that although DACT3 expression is reduced in colorectal cancer, this occurs independently of the DNA methylation previously implicated in gene silencing in these cells.

Figure 3D:
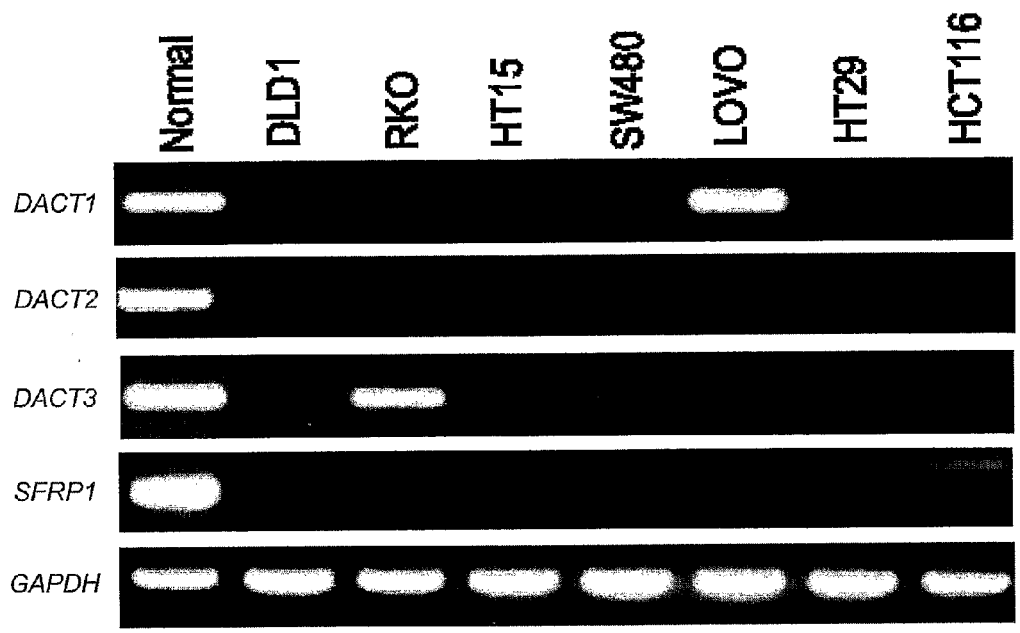
Figure 3E:
Figure 3F:
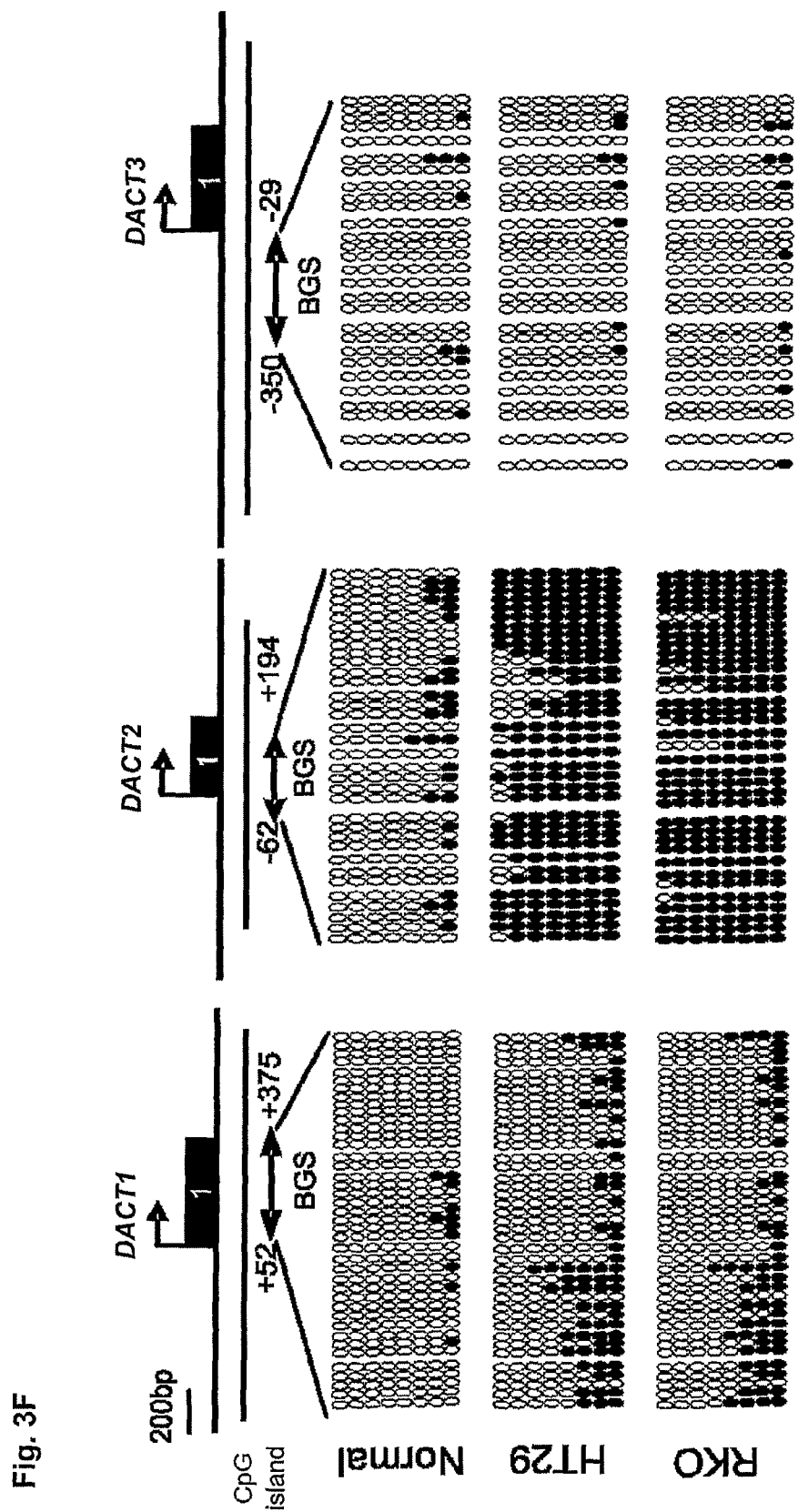
Figure 3G:

To determine whether the above observations are recapitulated in colorectal cancer cell lines, the inventors performed RT-PCR analysis of the DACT genes and of SFRP1 in 7 such lines (FIG. 3D). Unlike SFRP1, which is consistently silenced in colon cancer, DACT3 shows a basal level of expression that varies in different cell lines. Notably, expression of the other two DACT family members, DACT1 and DACT2, was also lost in several of these cell lines, though this was not observed in the primary tumor tissues examined above. Accordingly, the methylation status of all three DACT genes in these colorectal cancer cell lines was examined. As in the primary tumor samples, the DACT3 promoter is unmethylated in all the cell lines tested, whereas DACT1 and DACT2 promoters were found to be partially and fully-methylated, respectively (FIG. 3E). Bisulfite genomic sequencing in the RKO and HT29 cancer cell lines confirmed the results of this MSP analysis, showing partially and nearly completely methylated CpGs in the DACT1 and DACT2 promoters respectively, but almost no methylated cytosines in the DACT3 promoter (FIG. 3F).

The DNA methyltransferase inhibitor 5-aza-2'deoxycytidine (5-AzaC) was used to pharmacologically interfere with promoter methylation in the HCT116 colorectal cancer cell line. 5-AzaC treatment decreased methylation at the DACT1 and DACT2 promoters (FIG. 3G), leading to the increased expression of SFRP1, DACT1 and DACT2, but not DACT3

Figure 3H:
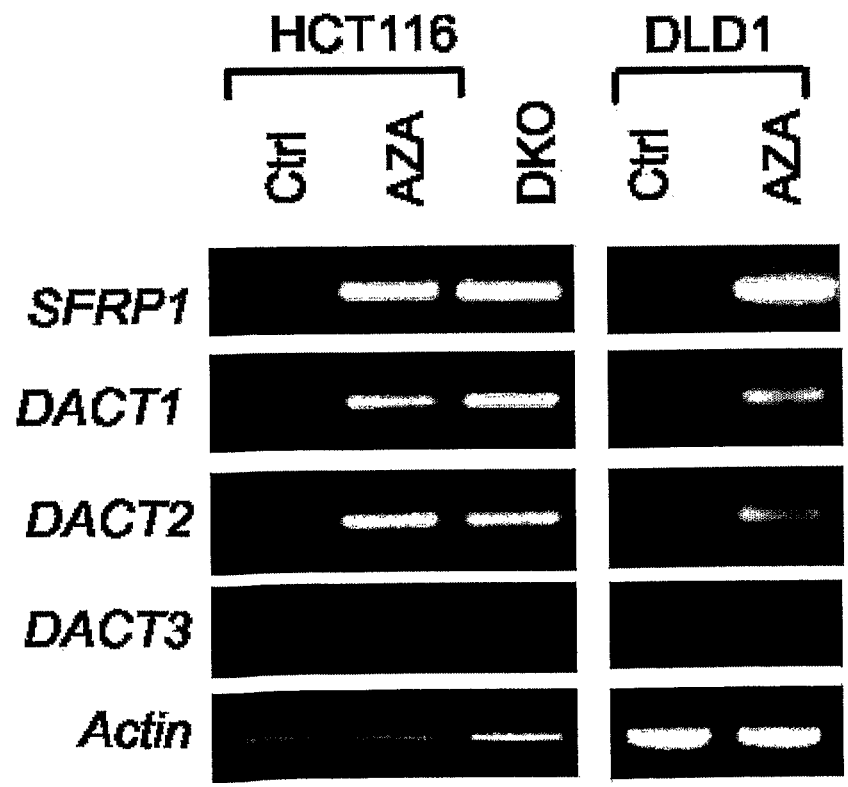

(FIG. 3H). Similarly, a HCT116 cell line in which the DNA methyltransferase genes DNMT1 and DNMT3B were genetically disrupted (Rhee, I., et al. *Nature* (2002) 416, 552-556) showed decreased promoter methylation (FIG. 3G; DKO) and increased expression (FIG. 3H) of DACT1, DACT2 and SFRP1 but no obvious change in DACT3 (FIGS. 1G and H). A similar result was also obtained in DLD1 cells (FIG. 3H). These results support the conclusion that unlike SFRP1 and the DACT1 and DACT2 genes, promoter methylation does not contribute to the epigenetic repression of DACT3 in colorectal cancer cells. Furthermore, it was found that in patient tumor samples DACT1 promoter was not methylated and DACT2 promoter methylation is only detected in several tumor samples with reduced DACT2 expression (data not shown). Thus, lack of methylation of DACT1/2 in clinical tumor samples that were examined may explain why they are not downregulated in these tumors in general.

Figure 4A:
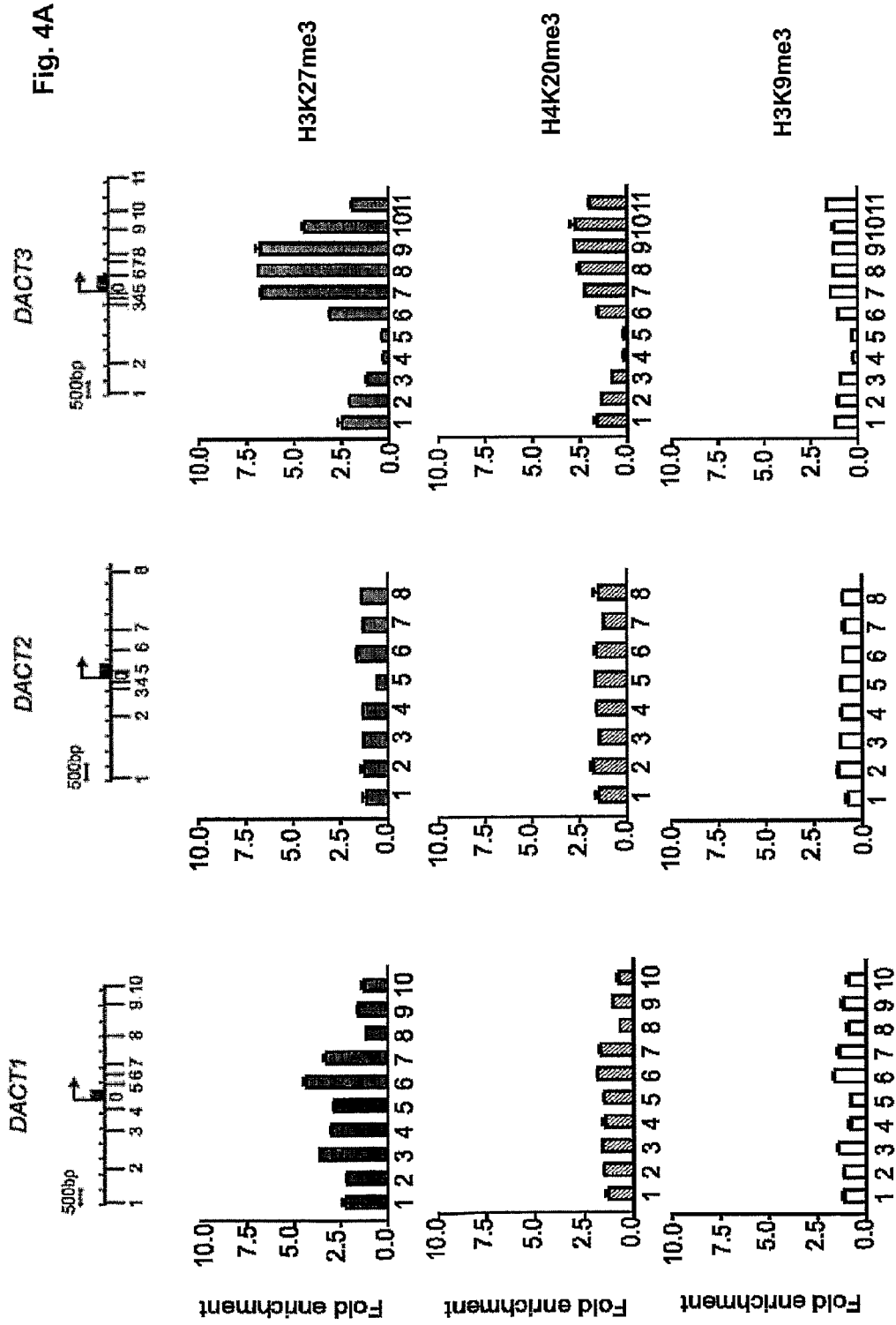
FIG. 4 depicts an analysis of histone modifications at DACT genes by means of the ChIP technique, showing Histone marks (A), H3K27me3 and H3K4me3 at DACT3 in cancer cells (B) and non-cancer cells (C).
Figure 4C:
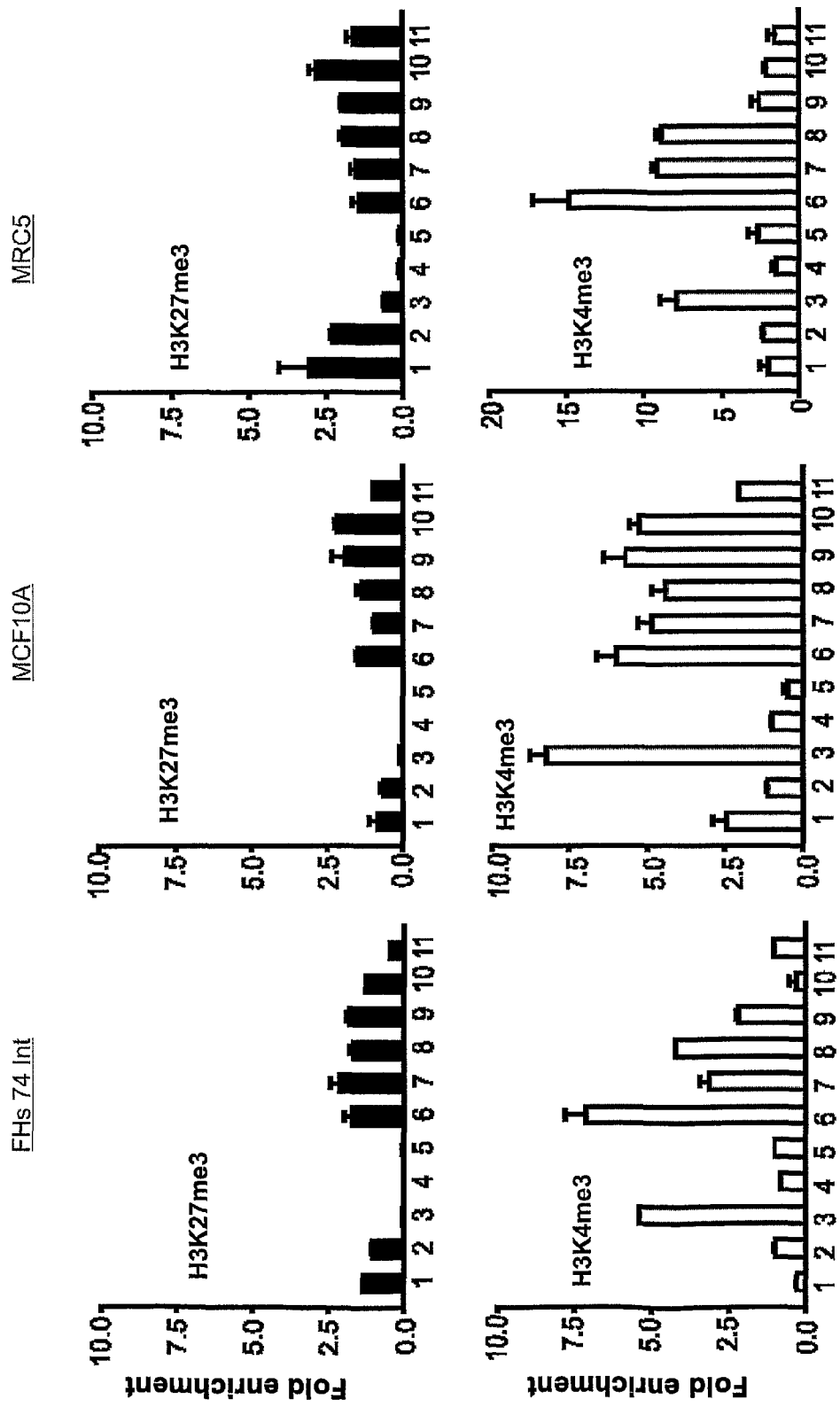

2.2 Epigenetic Repression of DACT3 is Associated with Bivalent Histone Modifications A chromatin immunoprecipitation (ChIP) assay was used to determine whether the chromatin status is associated with DACT3 repression. The assay was coupled with quantitative PCR to characterize potentially involved chromatin marks. A panel of 8-10 primer pairs was designed that covered a >7 kb region close to the transcription start site of each of the three DACT genes. The presence of histone marks was determined, including the presence of the repressive marks (cf. e.g. Szyf, 2009, supra) H3K27me3, H3K9me3, H3K9me2, and H4K20me3, as well as of the activating marks H3K4me3 (ibid.) and H3K9/14ac (FIG. 4A). Abundant enrichment of the repressive H3K27me3, and to a lesser extent repressive H4K20me3, was detected 500 bp downstream of the transcription start site of DACT3 in HT29 cells. In addition, a weaker H3K27me3 was also detected in the more upstream promoter region of DACT3. This finding is in agreement with several recent genome-wide studies showing that the majority of H3K27me3 is detected in the proximal downstream region of the transcription start site in both cancer and embryonic stem cells (Pan, G., et al., *Cell Stem Cell* (2007) 1, 299; Yu, J., et al., *Cancer Res* (2007) 67, 10657-10663; Zhao, Y., et al., *Proc Natl Acad Sci USA* (2005) 102, 16090-16095). In contrast, no repressive H3K9 methylation marks were detected in the DACT3 promoter region in HT29 cells.

The activating mark H3K4me3 was also detected at high levels near the DACT3 transcription start site in HT29 cells, suggesting that the DACT3 promoter is simultaneously modified by both repressive and activating (bivalent) histone methylation events in these cells. Such bivalent histone states have previously been correlated with genes transcribed at low levels (Azuara, V., et al., *Nat Cell Biol* (2006) 8, 532-538; Bernstein, B. E., et al., *Cell* (2006) 125, 315-326; Mikkelsen, T. S., et al., *Nature* (2007) 448, 553-560; Pan et al., 2007, supra; Zhao, X., et al., *Cell Stem Cell* (2007) 3, 286). If this is also true for the DACT3 locus, it could be predicted that the presence of repressive H3K27me3 should inversely correlate with DACT3 expression levels. Consistent with this hypothesis, high level of H3K27me3 was also detected at DACT3 in SW480 cells that express low levels of DACT3; to a lesser extent in RKO cells that have modest DACT3 expression (FIG. 4B). Moreover, only high level of H3K4me3 (but not H3K27me3) was detected at DACT3 in normal human intestinal epithelial cells (FHs 74 Int) and two other non-cancerous cell lines, breast epithelial MCF10A and lung fibroblast MRC5 (FIG. 4C), suggesting that this bivalent modification at DACT3 is cancer specific. To further confirm that the DACT3 promoter is in a bivalent histone state in cells where its expression is repressed, whole genome mapping of major histone marks in SW480 cells was conducted using ChIP-Seq Solexa technology. This high resolution mapping of histone modifications clearly demonstrates the co-modification of H3K27me3 and H3K4me3 at DACT3 (FIG. 7).

Enrichments of H3K4me3, and to a lesser degree, H3K27me3, were also detected at DACT1 but no enrichment peaks of these histone marks, including H3K4me3, were detected at the DACT2 locus (FIG. 4A). In general for the DACT gene family, these results suggest that the level of H3K4me3 is inversely correlated with the DNA methylation state: H3K4me3 is detected at the DACT1 promoter (which is partially methylated), and at the DACT3 promoter (which is not methylated), but not at the DACT2 promoter (which is fully methylated) (cf. FIG. 1F and FIG. 2). This finding agrees with recent reports that DNA methyltransferase preferentially binds to unmethylated H3K4 (Ooi, S. K., et al., *Nature* (2007) 448, 714-717) and that methylation of H3K4 tends to protect surrounding nucleotides from methylation (Weber, M., et al., *Nat Genet* (2007) 39, 457-466). Along with the earlier data showing that expression of DACT3 is insensitive to CpG island methylation, our data is consistent with the hypothesis that in colon cancer cells, DACT3 is repressed primarily through histone modifications, and specifically that the DACT3 locus in such cells exists in a bivalent chromatin state simultaneously containing both repressive and activating histone modifications.

2.3 Robust De-Repression of DACT3 by a Pharmacological Approach Inhibiting both Histone Methylation and Deacetylation It has recently been disclosed that the S-adenosylhomocysteine hydrolase inhibitor 3-Deazaneplanocin A (DZNep) depletes components of the polycomb-repressive complex 2 and inhibits histone methylation, including repressive H3K27me3 and H4K20me3 (Tan et al., 2007, supra). It was tested whether DZNep, alone or in combination with the histone deacetylase inhibitor Trichostatin A (TSA), the DNA methyltransferase inhibitor 5-AzaC, or both, could restore DACT3 expression in colorectal cancer cells. To allow most accurately measuring changes in gene expression, the Illumina beadarray was used. Using this tool it is possible to accurately measure transcript levels without intermediate nucleic acid amplification steps. It was observed that when used as single agents these drugs minimally induce expression of DACT3 in DLD1 cells (FIG. 5A). However, combined treatment with DZNep and TSA strongly induces DACT3 expression, whereas other combinations such as DZNep/Aza or TSA/Aza fail to do so (FIG. 5A). By contrast, a DZNep/TSA combination only induced a modest increase in DACT1 expression (FIG. 5B). Expression of DACT2, on the other hand, was only induced by treatments containing 5-AzaC (FIGS. 3H and 3B), consistent with its epigenetic silencing by more typical promoter methylation.

To determine the specificity of DZNep/TSA combination treatment for DACT3 de-repression versus changes in expression of other known Wnt/β-catenin pathway inhibitors, Illumina gene expression data were again analyzed using RNA from 2 colon cancer cell lines (DLD1 and HT-29); untreated or treated with DZNep, TSA or both. This analysis revealed that DACT3 is the only Wnt/β-catenin pathway inhibitor strongly induced by DZNep/TSA treatment and that this occurred in both colon cancer cell lines (FIG. 5B). Together, our findings show that DACT3 is distinguished from other Wnt pathway inhibitors in that its repression in colon cancer cells seems to be associated with the bivalent histone modifications but not DNA methylation, and accordingly it can be robustly de-repressed by a pharmacologic approach that exclusively targets histone modifications.

In order to better understand the mechanism by which the combination of the pharmaceutically active compounds DZNep and TSA reactivates DACT3 expression, histone modification profiles were examined in treated and untreated cells by Western blot (FIG. 5C). As previously reported, DZNep treatment alone results in strong reduction of H3K27me3 and H4K20me3, while having little effect on H3K9me3 (Tan et al., 2007, supra). Although the combination treatment resulted in some mild inhibition of H3K9me3, the most notable synergistic change compared to treatment with DZNep or TSA alone, was robust induction of H3K9/14 acetylation (FIG. 5C). Interestingly, H3K4me3 is also induced by this combination treatment, irrespective of a slight decrease with DZNep treatment alone. Thus, the pharmacologic combination of DZNep with TSA causes an intriguing global shift in histone modifications: it reduces certain repressive histone marks (H3K27me3, H4K20me3 and H3K9me3) while dramatically increasing some activating histone marks (H3K9/14ac and H3K4me3). Mechanistically, this suggests the existence of crosstalk between these chromatin marks, such that inhibition of repressive histone methylation by DZNep creates a favorable chromatin environment for histone acetylation induced by TSA. The magnitude of the effects observed on general histone profiles in these treated cells further suggests that this phenomenon is widespread throughout the genome. This in turn leads to increased expression of specific target genes, prominently including DACT3.

Figure 5D:
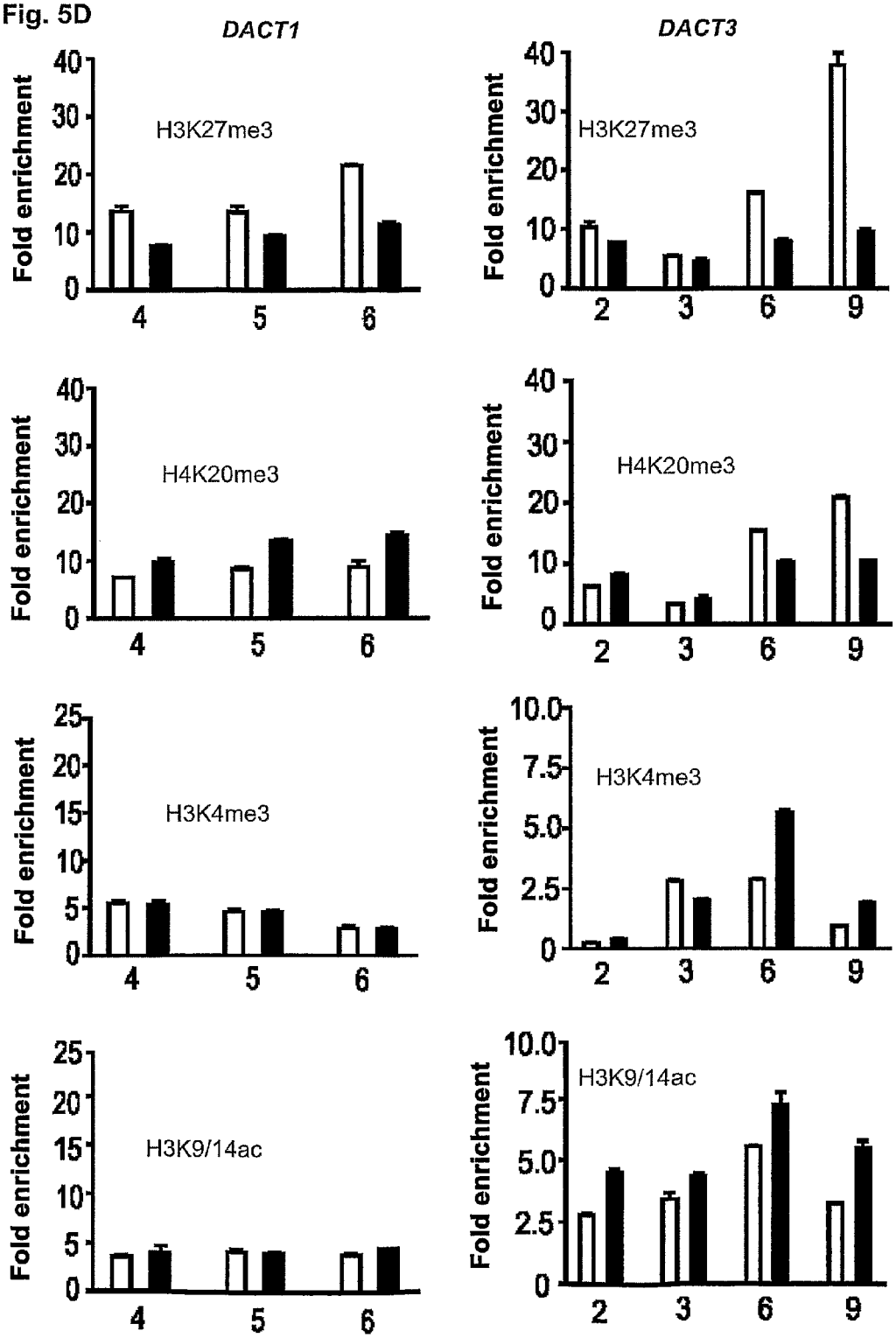

ChIP was used to further assess changes in histone modifications specifically at the DACT3 locus in response to DZNep/TSA combination treatment. Consistent with the global changes in modified histone levels found by Western blot analysis, cells treated with DZNep/TSA had a decrease in H3K27me3 and H4K20me3, and a concomitant increase in H3K4me3 and H3K9/K14ac at the DACT3 locus (FIG. 5D). Such effects were much weaker at the DACT1 locus, and thus correlate well with the relative effects of this pharmacologic treatment on DACT3 and DACT1 gene expression respectively. The striking changes in histone methylation and acetylation marks at the DACT3 locus are consistent with and help to explain the equally striking changes in DACT3 expression levels following DZNep/TSA treatment.

To summarize, the above biochemical, pharmacologic, and expression data, illustrated in the appended figures, all support a model in which repression of DACT3 expression occurs via a bivalent histone domain. Furthermore, this repression can be effectively reversed by a combined pharmacological approach that simultaneously inhibits both histone methylation and deacetylation, resulting in a major change in chromatic structure at a subset of such bivalently modified genes, prominently including the DACT3 locus.

Figure 6A:
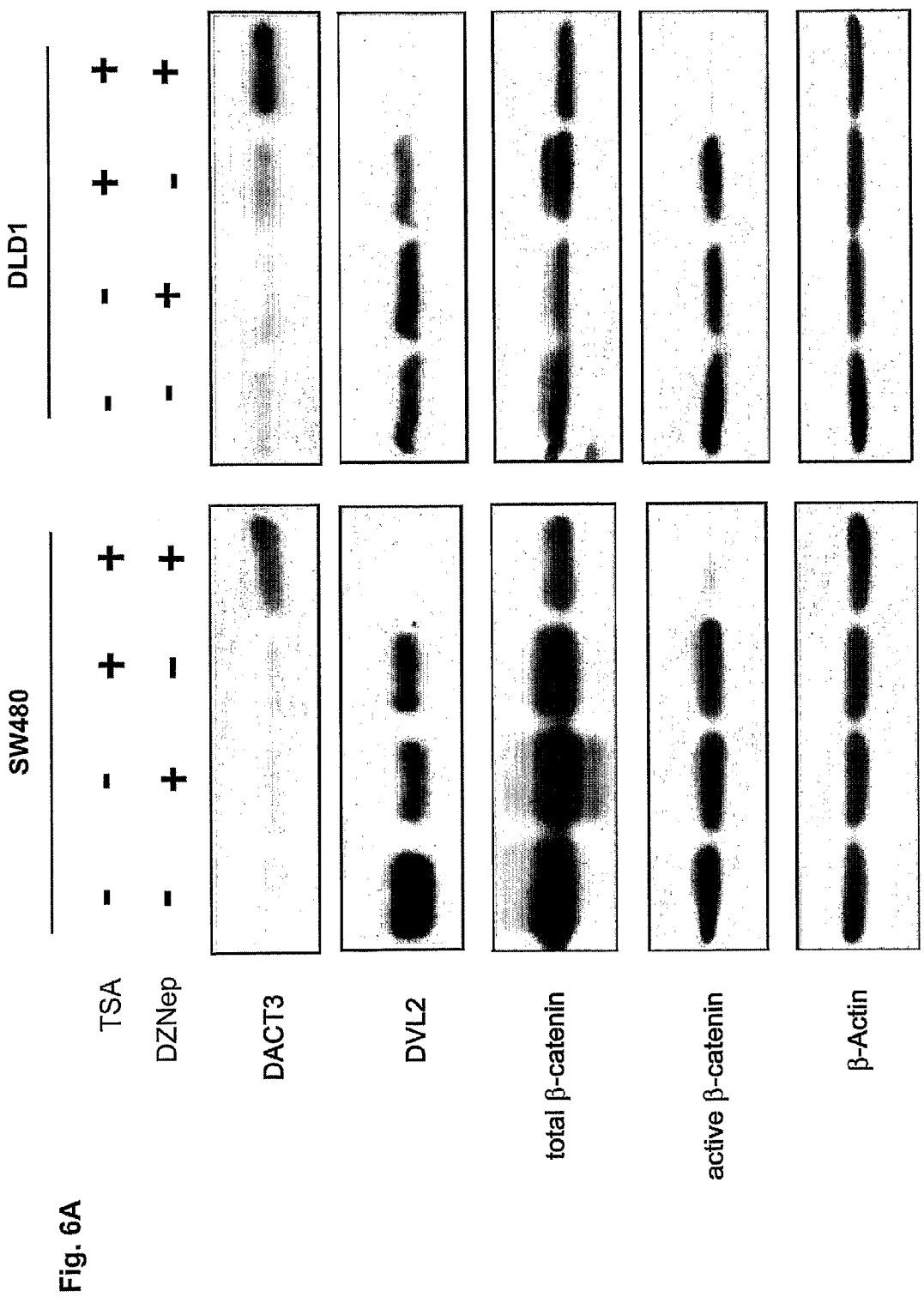
FIG. 6 illustrates the effects of a DZNep/TSA combination on β-catenin phosphorylation (A) and location (B), expression of Wnt/β-catenin signalling components (C, D), and apoptosis (E-G) in cancer cells.

2.4 De-Repression of DACT3 is Associated with Inhibition of Wnt/β-Catenin Signaling and Massive Apoptosis in Colorectal Cancer Cells The effects of the above pharmaceutically active compounds, alone and in combination, on DVL2 and β-catenin levels were examined. DVL2 was arbitrarily chosen as a representative of the DVL gene family as it is one of three functionally-redundant, conserved DVL family members expressed in all or most cell types (Hamblet, N. S., et al. *Development* (2002) 129, 5827-5838). Consistent with observed changes in transcript levels, DACT3 protein levels were markedly increased (in both SW480 and D1D1 cells) upon DZNep and TSA combination treatment as determined by Western blot analysis (FIG. 6A and FIG. 11). The combination treatment furthermore resulted in a decrease in DVL2 levels. In contrast, treatment with either DZNep or TSA alone did not cause such changes (FIG. 6A).

Figure 6B:
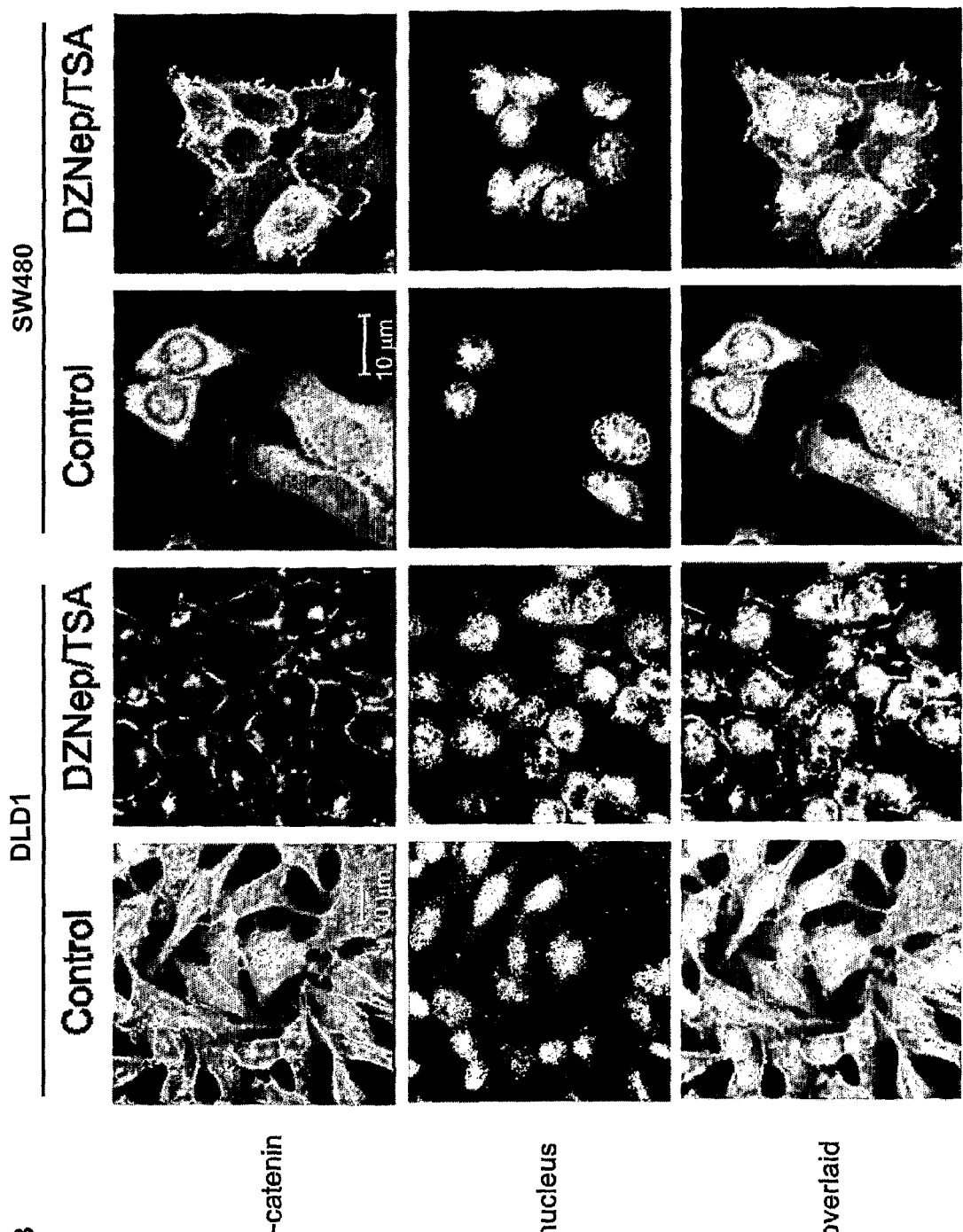
Figure 6C:
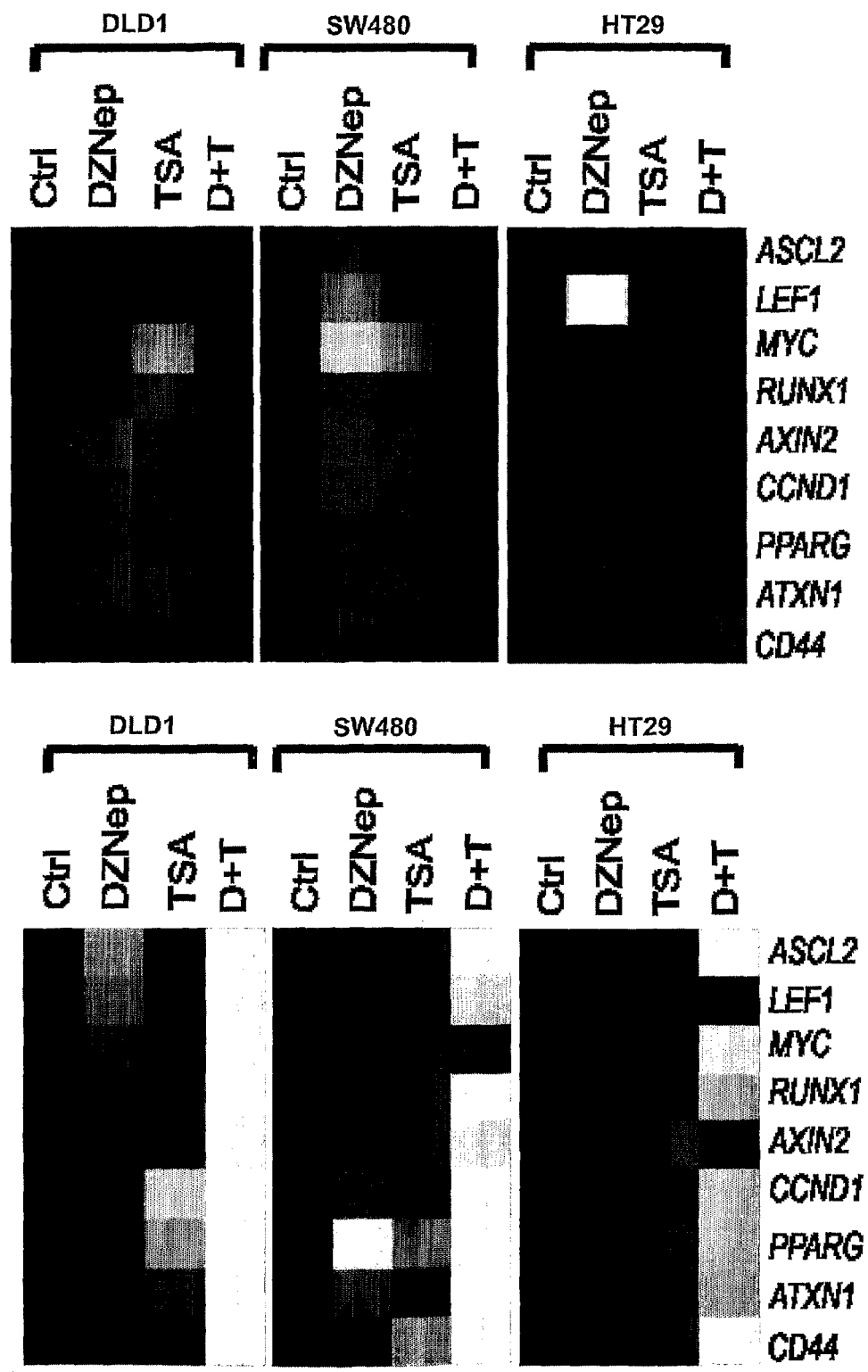

Concomitantly, levels of activated (non-phosphorylated) β-catenin dropped in DZNep/TSA-treated cells, as shown by Western blot (cf. FIG. 6A). This finding was confirmed by immunocytochemistry that showed diminished nuclear β-catenin staining upon treatment with DZNep/TSA (FIG. 6B). Finally, the expression of TCF/β-catenin target genes, including MYC, LEF, CCND1 and CD44, was markedly decreased in DZNep/TSA treated cells, but not in cells treated with either DZNep or TSA alone (FIGS. 6C and 6D). These findings uniformly indicate that Wnt/β-catenin signaling is inhibited by DZNep/TSA combination treatment. Furthermore, it was observed that the decrease of β-catenin upon DZNep/TSA can be effectively rescued by treatment of cells with a small molecule inhibitor of GSK-3, while the down-regulation of DVL2 remained unaffected (FIG. 10). This suggests that DACT3-DVL2 routes through GSK-3 to regulate β-catenin stability.

Among 81 genes the expression of which was increased by DZNep/TSA treatment in all the three cancer cell lines, DACT3 is by far the most heavily induced (cf. FIG. 12). To the best of the inventor's knowledge no other gene in this list (cf. FIG. 12) is directly relevant to Wnt/β-catenin signaling. Taken together, the results obtained here support that a DZNep/TSA combination treatment decreases Wnt/β-catenin signal transduction in colorectal cancer cell lines by increasing DACT3 gene expression and protein levels, secondarily destabilizing endogenous DVL proteins necessary for efficient Wnt signal transduction. Conversely, they suggest that repression of DACT3 is a key epigenetic event in colorectal cancer formation.

Figure 6F:
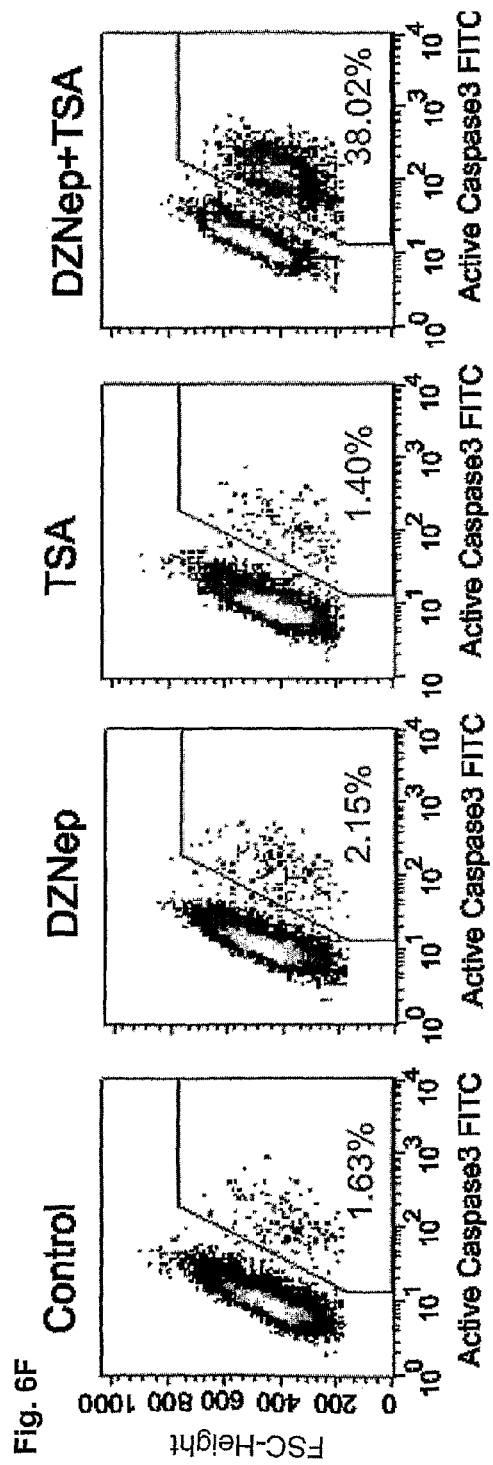
Figure 6G:
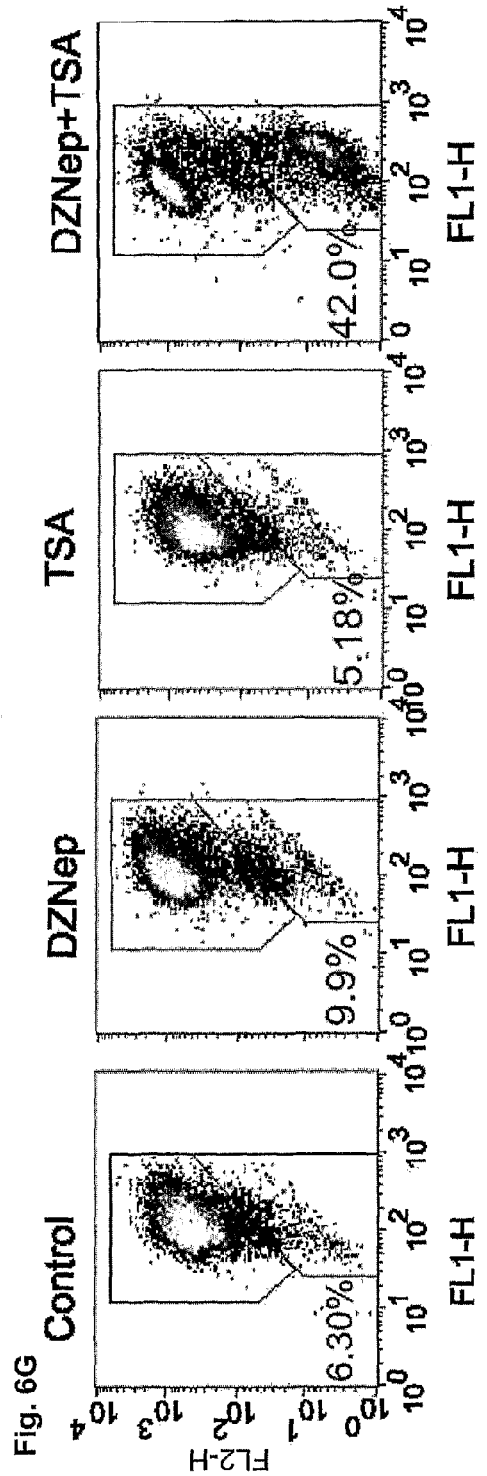

Inhibition of Wnt/β-catenin signaling is expected to block the pro-survival pathway and induce apoptosis in cancer cells that are addicted to this pathway (Fujii et al., 2007, supra; He et al., 2005, supra). Indeed, it was found that inhibition of Wnt/β-catenin signal transduction by DZNep/TSA was accompanied by a strong synergistic induction of cell death in DLD1 and HT29 cells, as assessed by propidium iodide (PI) and fluorescence-activated cell sorting (FACS) (FIG. 6E). Similar results were obtained using other colon cancer cell lines (data not shown). In contrast, cells treated with DZNep/Aza, a treatment that does not efficiently de-repress DACT3 expression, did not undergo comparable levels of cell death. Similarly, addition of 5-AzaC to the DZNep/TSA combination, which does not produce further increases in DACT3 gene expression, also does not produce additional increases in cell death. This suggests that modulation of DNA methylation by 5-AzaC and resultant effects on other potential gene targets does not contribute to further effects on Wnt/β-catenin signaling, and that induction of DACT3 alone by DZNep/TSA is associated with maximal cell death. The cell death induced by DZNep/TSA was further determined to be apoptotic. As shown in FIG. 6F, DZNep/TSA combination treatment, but not a treatment with only a single of these pharmaceutically active agents, resulted in a dramatic activation of Caspase 3 in HT29 cells (cf. FIG. 6F). Moreover, the combination treatment induced a sharp drop in mitochondrial transmembrane potential (MTP) (ΔΩm), indicative of mitochondrial dysfunction that is characteristic of apoptosis (cf. FIG. 6G).

The specific effects of DZNep/TSA treatment on histone modifications, DACT3 gene expression, activated β-catenin protein levels, and apoptosis were also seen in treatments combining DZNep with other HDAC inhibitors such as PXD101 and suberoylanilide hydroxamic acid (SAHA) (see FIG. 13). This shows that the effects of this pharmacological strategy that has been defined depend on the combined action of DZNep with an HDAC inhibitor, and are not idiosyncratic consequences of TSA administered in combination with DZNep.

Figure 8D:
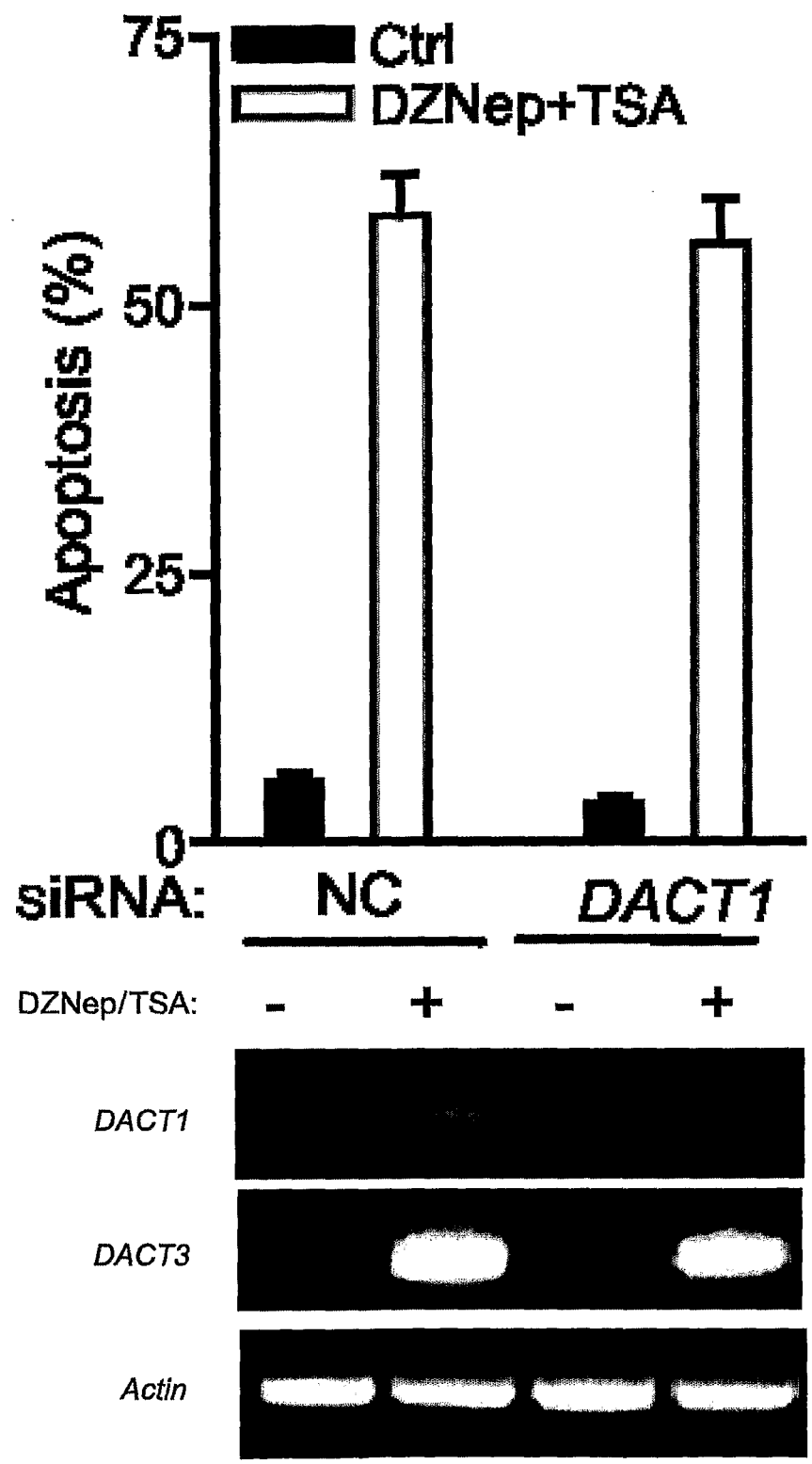
FIG. 8 shows the effects of DZNep/TSA on cancer cells depleted of DACT3 using shRNA (A, B) and siRNA (C, D) in terms of mRNA levels (A, C) and apoptosis (B, C), compared to cancer cells depleted of DACT1 using siRNA (D).

2.5 Functional Validation of DACT3 as a Critical Regulator of Wnt/β-Catenin Signaling To assess whether DACT3 transcriptional de-repression is required to decrease Wnt/β-catenin signaling in treated colorectal cancer cells, cell lines were generated derived from DLD1 that stably express a short-hairpin RNA targeting DACT3. Levels of the DACT3 mRNA following DZNep/TSA treatment were greatly diminished in two DLD1 clones expressing the DACT3 shRNA compared to control shRNA cells (FIG. 8A). Western blot analysis indicated that DZNep/TSA-induced effects on both DVL2 and unphosphorylated β-catenin levels were diminished in DACT3 shRNA cells (FIG. 8A). Moreover, when apoptosis was assayed, the induction of apoptosis by DZNep/TSA was markedly reduced in cell lines expressing DACT3 shRNA (FIG. 8B). These DACT3 knockdown effects are unlikely to be caused by off-target effects of the siRNA, because they were also observed in SW480 cells transiently transfected with two other independent DACT3 siRNAs (FIG. 8C). By contrast, knockdown of DACT1, which shows only a slight increase upon DZNep/TSA treatment, had no inhibitory effect on apoptosis (FIG. 8D). In summary, these results indicate that transcriptional de-repression of DACT3 contributes to inhibition of Wnt/β-catenin signal transduction and to apoptosis following DZNep/TSA treatment of colorectal cancer cells.

The function of DACT3 in regulating Wnt/β-catenin signal transduction was furthermore directly tested. DACT family members in various species have previously been shown to interact with DVL proteins through a highly-conserved C-terminal motif and to negatively regulate β-catenin function (Cheyette et al., 2002, supra; Zhang, L., et al., *J Biol Chem* (2006) 281, 8607-8612). To confirm that DACT3 also interacts with DVL proteins, coimmunoprecipitation experiments were performed by transfecting SW480 cells with expression vectors for Flag-tagged DACT3 and HA-tagged Dvl2. Under these conditions using either tag antibody, Dvl2 efficiently immunoprecipitates with DACT3, and conversely DACT3 efficiently immunoprecipitates with Dvl2 (FIG. 9A). Furthermore, co-transfection of Dvl2-HA with DACT3-Flag led to a marked decrease in Dvl2-HA protein expression compared to Dvl2-HA expressing cells co-transfected with an empty vector (FIG. 9B). These results demonstrate that, as predicted from homology with other DACT family members, DACT3 can indeed interact with DVL family members as exemplified by Dvl2. They further show that this interaction can reduce DVL protein stability, at least under these co-transfection conditions.

The effect of ectopic DACT3 expression on β-catenin levels in SW480 cells was similarly investigated using confocal immunochemistry. SW480 cells expressing Myc-tagged DACT3 or DACT1 had nearly undetectable levels of nuclear β-catenin, whereas untransfected cells or cells transfected with a non-relevant gene product, Myc-tagged RPS27L, retained high levels of nuclear β-catenin (FIG. 9C). Moreover, SW480 cells ectopically expressing DACT3 displayed condensed nuclei typical of apoptosis. These results demonstrate that ectopically expressed DACT3, like other Dact family members (Cheyette et al., 2002, supra; Hikasa, H., & Sokol, S. Y. *Development* (2004) 131, 4725-4734; Zhang et al., 2006, supra), can negatively regulate Wnt/β-catenin signaling, including in colorectal cancer cells.

To determine if DACT3 suppresses cell growth as a result of inhibition of oncogenic Wnt/β-catenin signaling, the colony formation assay was performed with DLD1 cells transfected with a DACT3 expressing plasmid or the control empty vector. Cells transfected with DACT3 show a dramatic decrease in colony numbers compared to control cells (FIG. 9D). This result further demonstrates that DACT3 functions as a potential tumor suppressor in colon cancer.

2.6 DZNep Toxicity in the Initial Maximum Tolerated Dose (MTD Study In Vivo

The objectives of this study were (i) to evaluate the maximum tolerated dose (MTD) for 3-Deazaneplanocin A (DZNep) in BALB/c nude mice given three times per week, and (ii) to assess the efficacy of DZNep in combination with the HDAC inhibitor SAHA in the HCT-116 human colon carcinoma xenograft model At the time of HCT-116 cell inoculation for the efficacy study, 3 mice/group were injected with 2.5, 5, 10 and 15 mg/kg DZNep i.p. at day 0, 2, and 4 to gather initial MTD data. Weight loss was very limited, and the highest weight loss was seen in the 10 mg/kg group (2.2% at day 2, raw data not shown). Two of three mice died in the absence of significant weight loss in the 15 mg/kg group at day 3 (raw data not shown). The MTD for DZNep in this regimen is therefore 10 mg/kg. For the following combination study where DZNep was used as a sensitizing agent, we decided to administer DZNep in a dose well below the MTD, i.e. 5 mg/kg.

The study was conducted as using the protocol described in FIG. 15. The combination study was started using four groups of BALB/c nude mice bearing HCT-116 tumors (n=7 mice/group, initial mean tumor volume 6 days after inoculation: 91-107 mm$^3$). We conducted this study fully vehicle-controlled, as one group of mice served as a vehicle control for both used compounds (Saline i.p. 3x/week in the morning, MC/Tween p.o. q.d. in the afternoon), a second group received SAHA (200 mg/kg q.d. p.o. in the afternoon) plus the DZNep vehicle (Saline 3/week i.p. in the morning), a third group was treated with DZNep (5 mg/kg i.p. in the morning) plus the SAHA vehicle (MC/Tween p.o. q.d. in the afternoon), and the last group was treated with DZNep plus SAHA (5 mg/kg DZNep i.p. in the morning, plus 200 mg/kg q.d. p.o. in the afternoon).

FIG. 16 shows that while the weight in the vehicle group steadily increased to 106.8% within 14 days, both DZNep and SAHA treatment alone induced a very moderate weight loss (94.5% and 96.8%, respectively). The combination treatment group displayed a significant, but still tolerable weight loss to 87.9% at day 14. One animal in the SAHA group was lost due to a gavage error at day 4, and a second mouse died with a body weight of 82% in the SAHA group as well (regarded TRD). The combination of 5 mg/kg DZNep 3x/week plus 200 mg/kg SAHA q.d. however was well-tolerated by BALB/c nude mice in this experiment.

2.7 Efficacy of DZNep in Combination with SAHA in the HCT-116 Model

All tumors in the vehicle control group grew steadily over 14 days as shown in FIG. 14B, and the mean tumor volume at day 14 post-treatment was 395.4 mm³. The MTV tumor distribution data are graphically displayed in FIG. 17, and all TGI data of days 3, 7, 10 and 14 are shown in FIG. 18. The individual tumor caliper measurements and body weights (raw data) are not shown.

After 14 days of treatment, the SAHA group had a tumor growth inhibition (TGI) of 55% (not significant), whereas DZNep-treated animals displayed no TGI at all. The combination treatment with DZNep plus SAHA induced a significant TGI of 83% (mean tumor volume of 145.1 mm³, P<0.05 ANOVA/Dunnett's).

3. Discussion

The present invention is based on the finding of an epigenetic event that contributes to the constitutive activation of Wnt/β-catenin signaling in human colorectal cancer. It is shown here that transcriptional repression of the DACT3 gene occurs frequently both in colorectal cancer cell lines and in patient-derived tumors. Data are presented that suggest that DACT3, together with SFRPs, m be a key epigenetic regulator of the Wnt/β-catenin signaling pathway in this disease process. DACT3 is thus a potentially important target for cancer therapies aimed at controlling aberrant Wnt/β-catenin signaling. The techniques illustrated above can readily be employed in the methods and uses according to the invention.

Unlike the SFRP genes, the expression of which is often completely silenced by promoter DNA methylation, DACT3 is expressed at low levels in colon cancer cell lines. The invention shows that this epigenetic event occurs through a bivalent histone modification that contains both repressive (H3K27me3) and activating (H3K4me3) histone marks at the DACT3 locus and does not involve or require methylation of the promoter DNA. As a result of this epigenetic regulation, levels of DACT3 can be strongly induced by a pharmacological treatment that targets histone modifications: specifically, combination treatment that simultaneously interferes with both histone methylation and deacetylation. By contrast, this treatment does not reactivate genes silenced predominately by DNA methylation, such as SFRP1 or DACT2, and only modestly induces DACT, the repression of which in colon cancer cells is linked to both DNA methylation and histone modifications. This data illustrates that a combined administration of DZNep and a histone deacetlyase inhibitor such as TSA preferencently reactivate genes predominately repressed by bivalent histone modifications with minimum DNA methylation.

The bivalent chromatin has been previously described in both embryonic stem (ES) cells and some differentiated cells, where they are in general associated with genes expressed at low levels (Azuara et al., 2006, supra; Barski, A., et al., *Cell* (2007) 129, 823-837; Bernstein et al., 2006, supra; Mikkelsen et al., 2007, supra; Pan et al., 2007, supra; Zhao et al., 2007, supra). Some tumor suppressor genes with bivalent histone marks in ES cells lose the H3K4me3 mark during oncogenesis, but instead become fully silenced through DNA methylation (Ohm, J. E., et al., *Nat Genet* (2007) 39, 237-242; Schlesinger, Y., et al., *Nat Genet* (2007) 39, 232-236; Widschwendter, M., et al., *Nat Genet* (2007) 39, 157-158). The data obtained by the present inventors suggest that a bivalent chromatin state occurred in cancer cells might also contribute to cancerous transformation. Importantly, this epigenetic modification at the DACT3 locus is apparently cancer specific as no such modifications were observed at the DACT3 locus in normal intestinal epithelial cells. Genes found in such a bivalent chromatin state in cancer cells (such as DACT3) therefore represent unique therapeutic targets. Unlike tumor suppressors that are silenced by DNA methylation, genes carrying a bivalent chromatin such as DACT3 may be particularly subject to manipulation by treatments such as with DZNep and a histone deacetlyase inhibitor that target both histone methylation and deacetylation. Identifying these alternately-regulated tumor suppressor genes is also important because they are likely to be insensitive to therapies that only target DNA methylation, such as Aza.

Although presently speculative, it is possible that the chromatin pattern observed in the context of the present invention at the DACT3 locus in colorectal cancer cells is part of the molecular signature of stem cell-like cancer cells. There is evidence that Wnt/β-catenin signaling plays a central role in the maintenance of epithelial stem cells and of early progenitors and that it is involved in the generation of iPS cells (see above). The combined pharmacologic approach of the invention, which targets in some embodiments an epigenetic signature characteristic of inter alia colorectal cancer cells and which is capable of abrogating Wnt/β-catenin signaling, may have the potential to target cancer stem cells that rely on this mechanism of gene silencing and that require high levels of Wnt/β-catenin signaling activity for their self-renewal and survival.

The obtained results illustrate the diversity and complexity of epigenetic mechanisms involved in gene repression in cancer cells. Use of DZNep as a histone methylation inhibitor in combination with other chromatin remodeling compounds may make it possible to discover other cancer genes regulated through various epigenetic mechanisms. The combined effects of DZNep and HDAC inhibitors such as TSA on overall histone modification profiles is provocative, because together this drug combination appears to switch a repressive chromatin state into an active one by simultaneously reducing repressive histone marks (H3K27me3) and increasing activating marks (H3K4me3 and H3K9/14ac). This pharmacologic intervention, together with a DNA methylation inhibitor, might therefore have the potential to revert a globally "malignant" chromatin state found in some cancer cells into a more normal "benign" one. Although it remains to be biochemically determined how a treatment with DZNep and a histone deacetylase inhibitor generates such strong synergy in histone acetylation this is nevertheless likely to reflect direct cross-talk between these two types of histone modification. The presented data further suggest that such pharmacologic epigenetic "reprogramming" of histone modification profiles across the genome can lead to profound changes in gene expression, affecting multiple signaling pathways simultaneously. Indeed, our microarray data shows that DACT3 is not the only gene regulated in this manner; the expression of at least 81 other genes was significantly affected by combined treatment with DZNep and a histone deacetylase inhibitor. It is possible that inhibition of Wnt/β-catenin signaling cooperates with other signaling effects to yield the maximal apoptotic response observed upon this combination treatment.

The present invention shows that increasing the levels of DACT3 protein in colorectal cancer cells, either through pharmacologic de-repression or via ectopic expression, results in robust degradation of DVL2 and to decreases in activated β-catenin. This DACT3-DVL2 signaling interaction might route through GSK-3 to regulate β-catenin stability. This notion is supported by the finding that a small molecule inhibitor of GSK-3 can rescue the decreases in activated β-catenin caused by treatment with DZNep and a histone deacetylase inhibitor. As reported here the present inventors have also found that decreases in activated β-catenin caused by increasing DACT3 can occur even in the presence of APC mutations. This finding is consistent with numerous reports suggesting that deregulated β-catenin phosphorylation and degradation still takes place in colorectal cancer cells carrying APC mutations (Calviello, G., et al., *Carcinogenesis* (2007) 28, 1202-1209; Rice, P. L., et al., *Mol Cancer Ther* (2003) 2, 885-892; Suzuki et al., 2004, supra; Yang, J., et al., *J Biol Chem* (2006) 281, 17751-17757). In particular, it has been shown that restored expression of SFRP1/2 can effectively degrade β-catenin in colorectal cancer cells carrying these downstream mutations (Calviello et al., 2007, supra; Rice et al., 2003, supra; Suzuki et al., 2004, supra). These findings, together with ongoing studies suggest that there are alternate molecular mechanisms that contribute to β-catenin regulation independently of APC in colorectal cancer cells.

The data obtained in the context of the present invention also suggest that multiple abnormal epigenetic events might contribute to aberrant activation of the Wnt/β-catenin signaling pathway in colon cancer. These multiple events might occur in the same cell, or they may be present in different cells within a tumor. By increasing heterogeneity in a tumor cell population, epigenetic events may contribute to cancer progression, and also contribute to treatment resistance and cancer recurrence.

In short, the data of this disclosure demonstrates that epigenetic repression of DACT3 leads to aberrant Wnt/β-catenin signaling in colorectal cancer cells. Our data represent an important advance toward understanding how a previously unknown epigenetic event contributes to deregulation of Wnt/β-catenin signaling in colorectal cancer. This work also provides an important proof-of-principle that such epigenetic events can be specifically targeted by pharmacologic strategies to yield robust effects on Wnt/β-catenin signaling with important consequences for cancer eradication.

The results obtained in the in vivo study indicate that a combination of the S-adenosylhomocysteine hydrolase inhibitor DZNep and SAHA can be effective against solid tumors when DZNep was given in a low, well-tolerated dose. The TGI data of 83% were significant, whereas treatment with DZNep alone was not efficacious at all (0% TGI). Since SAHA alone had a moderate TGI of around 50% as in several previous experiments, it can be concluded that a synergism exists between the effects of DZNep and SAHA.

4. List of Abbreviations Used

| Abbreviation | Description |
| --- | --- |
| b.i.d. | bis die, twice a day |
| BRC | Biological Resource Centre, Biopolis |
| BW | body weight |
| CR | complete regression |
| DZNep | 3-Deazaneplanocin A |
| HDAC | Histone deacetylase |
| IACUC | Institutional Animal Care and Use Committee |
| i.p. | Intraperitoneally |
| LTTFS | long-term tumor-free survivor |
| MC/Tween | 0.5% Methylcellulose + 0.1% Tween 80 |

-continued

| Abbreviation | Description |
| --- | --- |
| MTD | Maximum tolerated dose |
| MTV | median tumor volume |
| NTRD | non-treatment-related death |
| p.o. | per os, orally |
| PR | partial regression |
| q.d. | quaque die, once a day |
| SAHA | suberoylanilide hydroxamic acid |
| TGI | tumor growth inhibition |
| TRD | treatment-related death |
| TSA | trichostatin A |

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," "containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

What is claimed is:

1. A method of treating colon cancer, the method comprising:

increasing at least one of the amount and the activity of a DACT3 ("dapper, antagonist of beta-catenin, homolog") protein, or a functional fragment thereof, wherein the increase in the amount and the activity of the DACT3 protein, or the functional fragment thereof is achieved by administering a combination that increases the expression and/or the activity of the DACT3 protein, or a functional fragment thereof; and wherein the combination is a compound of formula I

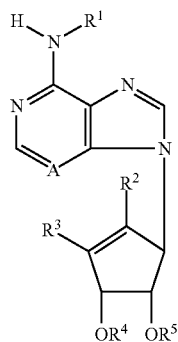

(I)

wherein in formula (I)

A is CH, $R^1$, $R^4$ and $R^5$ are independently selected from the group consisting of H and aliphatic, wherein $R^4$ and $R^5$ may optionally be linked so as to define an aliphatic hydrocarbyl bridge, $R^2$ is selected from the group consisting of H and halogen, and $R^3$ is H, or an aliphatic or arylaliphatic hydrocarbyl group comprising 1-8 main chain carbon atoms and 0-3 heteroatoms selected from the group N, O, S, Si, and halogen;

and a histone deacetylase inhibitor, wherein the histone deacetylase inhibitor is a compound of one of the general formula (II) and the general formula (III),

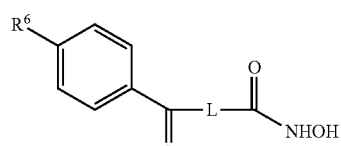

(II)

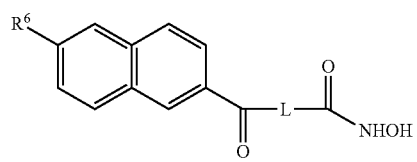

(III)

wherein $R^6$ is one of H, an amino group, an ether group, an aliphatic group and an arylaliphatic group and L is a bridge comprising an aliphatic or arylaliphatic group comprising 1-8 main chain carbon atoms and 0-3 heteroatoms selected from the group N, O and Si;

assessing at least one of the amount and the activity of the DACT3 protein, wherein assessing the amount of the DACT3 protein is achieved by measuring gene expression of the DACT3 protein; and comparing the result of the measurement of DACT3 gene expression with that of a control measurement.

2. The method of claim 1, wherein assessing the amount and/or activity of the DACT3 protein comprises assessing the amount and/or activity over a period of time before, during and/or after administering the compound.

3. The method of claim 1, wherein the control measurement comprises the use of conditions that do at least essentially do not modulate gene expression of the DACT3 protein.

4. The method of claim 1, wherein the method comprises treating colon cancer in a cell, wherein the cell is obtained from or is comprised in a host organism.

5. The method of claim 4, wherein the host organism is one of a microorganism, a fish, an amphibian, a bird and a mammal.

6. The method of claim 1, wherein increasing at least one of the amount and the activity of a DACT3 protein, or a functional fragment thereof, further comprises reducing the amount of a dishevelled protein.

7. The method of claim 6, wherein the dishevelled protein is one of Dvl1, Dvl2 and Dvl3.

* * * * *

SEQUENCE LISTING

<160> NUMBER OF SEQ ID NOS: 122

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gacccaggcg accataggag ctggatc                                           27

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctggatcca gagaagccac tgtcccca                                          28

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cacagaaggt tgagggtggt gaatctggac ct                                     32

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
attgaattca atgatccggg ccttctcgtt cccggt                                 36

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
attagatctt cacactgtag tcatgacctt gagagaaccc ga                          42

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      target oligonucleotide siRNA

<400> SEQUENCE: 6
gguucucuca aggucauga                                                    19

```
<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      SiRNA oligonucleotide

<400> SEQUENCE: 7
ggagaaucgc cugccuuca                                                    19

<210> SEQ ID NO 8
<211> LENGTH: 14
<212> TYPE: PRT
<213> ORGANISM: Homo sapiens
<220> FEATURE:
<223> OTHER INFORMATION: Antigenic peptide of DACT3

<400> SEQUENCE: 8

Leu Ser Leu Glu Ser Gly Gly Leu Glu Gln Glu Ser Gly Arg
1               5                   10

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctccccagcg tcgtctgctt ta                                                22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
attcgctctc cccgtaaccc                                                   20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cctgcacgcc gtggctctac                                                   20

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccctgttctc cctcgctacc ctt                                               23
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cagtcgcctg gaggagaagt                                            20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctgcttgtca agctcttgca                                            20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aggcgtgcaa atctgtctcg                                            20

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgcatttgga tagctggttt agtg                                       24

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgcgttgatg cggagcaagg at                                         22

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttattgcagc gggtactggg gcag                                       24

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aggaggccac cctcaatgag                                            20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cagcttcttc tgcctccatc                                            20

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcggccgcga gtacgacta                                             19

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcttgtagcc cacgttgtgg                                            20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctggattttt tcgggtagt gg                                          22

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcgcagtaga aatacggctg                                            20

<210> SEQ ID NO 25
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atggaacacc agctcctgtg                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ttgaagtagg acaccgaggg                                               20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caaagttgtc atggatgacc                                               20

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccatggagaa ggctgggg                                                 18

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtggggcgcc ccaggcacca                                               20

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctccttaatg tcacgcacga tttc                                          24

<210> SEQ ID NO 31
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tagttttagc gttttgtttt ttcgt                                         25

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
taccgctcga tatctacctc g                                             21

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tagttttagt gttttgtttt tttgt                                         25

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctaccactca atatctacct cacc                                          24

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
taggaggatt cgcgatatag ttc                                           23

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tacaactcct acaaccccgc                                               20

<210> SEQ ID NO 37
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
taggaggatt tgtgatatag tttgg                                          25

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cctacaactc ctacaacccc ac                                             22

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aattttatcg gaggacgttc                                                20

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cttacgaacg aacgctaact ac                                             22

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aataatttta ttggaggatg ttt                                            23

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cttacaaaca aacactaact accat                                          25

<210> SEQ ID NO 43
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 43
agttttcgtt aggaagttta ttcgt                                          25

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tatcaccgtc tcatctacat aaacg                                          25

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agtttttgtt aggaagttta tttgt                                          25

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atcaccatct catctacata aacacc                                         26

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gatagttcgg ttagcgggc                                                 19

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aacgcctact acacgcgata                                                20

<210> SEQ ID NO 49
<211> LENGTH: 22
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 49
ggtgatagtt tggttagtgg gt                                            22

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aacacctact acacacaata ctc                                           23

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ttcgtttgtg tttgtttgtt tc                                            22

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
acccgatctc gaatttaaca                                               20

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
atttttgttt gtgtttgttt gtttt                                         25

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tacccaatct caaatttaac aca                                           23

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 55
cgcgtttggt tttagtaaat c                                              21

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ccgaaaatac gacgaaca                                                  18

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
agttgtgttt ggttttagta aatt                                           24

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ctcccaaaaa tacaacaaac a                                              21

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59 attggggtt atgaagtyg                                                  19

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tccaaaaact tctcctccaa ac                                             22

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 61
tggttataga ttttagttta ttttgg                                          26

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
caacccctac aactcctaca ac                                              22

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aagagggtgg aatttgttgt a                                               21

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tcaccrtctc atctacataa ac                                              22

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gtgcaactga tgcccttac                                                  20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ttgtccagcg gtgaacattc                                                 20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 67
gcttgtctgc ctgacttaag                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tggcctgtgt tatgtcacac                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tgtgctagcc acgttgtaag                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gctatgggaa cctgctgttg                                              20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gacgagaaag agccaatgag                                              20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72 cctttcggg tttactgcac                                               20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
```

-continued cttggaggag aacatcttgc                          20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ttcgggcacg acctaccaat                          20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tcgcctagtt ctaacgttcg                          20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cgggaggaga taaagtcaag                          20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tctgccagct gtgattggtg                          20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
actgagacac tgacagaaac                          20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79

```
gaggcgttca aatctcgatg                                              20
```

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80

```
ccagtgccaa gtataatgtg                                              20
```

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81

```
gtaagtcaga actgggctag                                              20
```

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82

```
aatctaagga gcccaaatgg                                              20
```

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83

```
aactcggtgt tcagtgagtg                                              20
```

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84

```
ggcaaccatc tgagagactc                                              20
```

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85

```
gctgacgtca tacttaacag                                              20
```

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ccaggatggg tacctttac                                             20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
aagatgctca acgtccttag                                             20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cagatgtgaa gtggtatctc                                             20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gaggtgcggt ttccaaactg                                             20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
attgcaagga ccgtgttacc                                             20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
caagcctttc tccgcctttg                                             20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
gagcgcctcc gtgacttcag                                                  20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
cagcccacct tggcgacctg                                                  20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
gcggatcccg agctgtgtcg                                                  20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
ccgacttgtc ctcaggaatg                                                  20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 96
ctccttacag gtcaggtcac                                                  20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
gactgtgtgg gattaacctg                                                  20

```
<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ctttcctctc aggaggcatc                                               20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gctgctgaga tgctgttgtg                                               20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
acagaacagt tgaagccagc                                               20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
ctcagatggg atggaccta                                                20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
attcccattc agcacaggtc                                               20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cttcactcgc accaccaaag                                               20

<210> SEQ ID NO 104
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cctttgagga aggcgtgtag                                                     20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gtgtctggga aggcttcttg                                                     20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cccaaccttc agcttctgag                                                     20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
aggcacagac caatggcatt                                                     20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ccacgcgtca caatgaaaca                                                     20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ttgcgagcat gcgtcgtgtt                                                     20

<210> SEQ ID NO 110
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
cgagcaacag ccgcctattg                                               20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
tgtctgtctg tctcggttgg                                               20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
accccctgtc ctttctcact                                               20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ttccctaagt cctggtgtgc                                               20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
tcctcaggga ctgtgagctt                                               20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ctggactctg ggtgttctca                                               20

<210> SEQ ID NO 116
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 116
cgggagactc aaggaatgac                                                   20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
cagtctctag gcaaagcttg                                                   20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gccctaatcc actcttcaga                                                   20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
ggaattagac ttggcagaac                                                   20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
cttcagcctg agagactttg                                                   20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gtgaggtccc agagactatg                                                   20

<210> SEQ ID NO 122
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 122
tgattacagc ctgcagtcac                                              20
```